US007972849B2

(12) United States Patent
Mitalipov et al.

(10) Patent No.: US 7,972,849 B2
(45) Date of Patent: Jul. 5, 2011

(54) PRIMATE PLURIPOTENT STEM CELLS PRODUCED BY SOMATIC CELL NUCLEAR TRANSFER

(75) Inventors: Shoukhrat M. Mitalipov, Hillsboro, OR (US); Don P. Wolf, Portland, OR (US); James Byrne, Palo Alto, CA (US)

(73) Assignee: Oregon Health & Science University, Portland, OR (US)

( * ) Notice: Subject to any disclaimer, the term of this patent is extended or adjusted under 35 U.S.C. 154(b) by 302 days.

(21) Appl. No.: 12/122,557

(22) Filed: May 16, 2008

(65) Prior Publication Data

US 2009/0004740 A1   Jan. 1, 2009

Related U.S. Application Data

(60) Provisional application No. 60/938,683, filed on May 17, 2007, provisional application No. 60/940,316, filed on May 25, 2007, provisional application No. 60/942,427, filed on Jun. 6, 2007.

(51) Int. Cl.
 *C12N 5/02* (2006.01)
(52) U.S. Cl. .......................................... 435/373; 800/24
(58) Field of Classification Search ........................ None
See application file for complete search history.

(56) References Cited

U.S. PATENT DOCUMENTS 6,252,133 B1 *  6/2001  Campbell et al. ............... 800/24
6,879,713 B1     4/2005  Keefe
2005/0063962 A1  3/2005  Ng et al.

FOREIGN PATENT DOCUMENTS

WO   WO 2005/005624   1/2005

OTHER PUBLICATIONS

Nagy et al. Embryonic Stem Cells Alone are Able to Support Fetal Development in the Mouse. Development, 1990, vol. 110, 815-821.*
Nagy et al. Derivation of Completely Cell Culture-Derived Mice from Early-Passage Embryonic Stem Cells. Proc. Natl. Acad. Sci., 1993, vol. 90, pp. 8424-8428.*
Strojkovic et al, Derivation of a Human Blastocyst After Heterologous Nuclear Transfer to Donated Oocytes. RMB Online, 2005, vol. 11, pp. 226-331.*
Ahn et al., "Transgenesis and Nuclear Transfer Using Stem Cells from Cultured Porcine Primordial Germ Cells," *Reprod. Fert. Develop.* (2005) (Abstract).
Akagi et al., "In Vitro Development of Aggregated Nuclear Transferred Embryos Derived from Bovine Cumulus Cells," *Reprod. Fert. Develop.* (2005) (Abstract).
Alexander et al., "Assessment of Chromosome Abnormalities in Sheep Parthenogenetic and Nuclear Transfer Embryos: Effect of 6-DMAP and Cycloheximide on Ploidy," *Reprod. Fert. Develop.* (2005) (Abstract).
Alexopoulos et al., "Morphological and Immunohistochemical Characterization of Day 21 IVP and NT Bovine Embryos," *Reprod. Fert. Develop.* (2005) (Abstract).
Arat et al., "Cloned Embryos Can Be Produced Using Donor Cells Obtained From a 72-Hour Cooled Carcass," *Reprod. Fert. Develop.* (2005) (Abstract).
Batchelder et al., "Comparison of Term Placentas in Cloned and Control Pregnancies in Cattle," *Reprod. Fert. Develop.* (2005) (Abstract).
Bongso et al., "Isolation and culture of inner cell mass cells from human blastocysts," *Human Reproduction*, 9(11):2110-2117, (1994).
Boquest et al., "Production of Cloned Pigs from Cultured Fetal Fibroblast Cells," *Biol. Reprod*, 66:1283-1287, (2002).
Carpenter et al., Characterization of Differentiation of Human Embryonic Stem Cells, *Cloning and Stem Cells*, 5:79-88,(Nov. 1, 2003).
Chang et al., "Construction of a Targeting Vector Specific for the Bovine Beta-Casein Gene," *Reprod. Fert. Develop.* (2005) (Abstract).
Cho et al., "Efficiency of Female-Derived Donor Cells on High Postnatal Survival in Pig Cloning," *Reprod. Fert. Develop.* (2005) (Abstract).
Fujimura et al., "Production of Transgenic-Cloned Pigs Carrying HDAF, GnT-III and Heterozygously Disrupted α-1,3-Galactosyltranserase Genes," *Reprod. Fert. Develop.* (2005) (Abstract).
Giraldo et al., "Lifespan and Chromosomal Stability of Bovine and Porcine Fetal Fibroblast Cells Cultured in Vitro," *Reprod. Fert. Develop.* (2005) (Abstract).
Givens et al., "Production of Cloned Miniature Calves Using Cytoplasts from Cows of Standard Size," *Reprod. Fert. Develop.* (2005) (Abstract).
Gomez et al., "Improving the Application of Nuclear Transfer for Producing Non-Domestic Felids," *Reprod. Fert. Develop.* (2005) (Abstract).
Heyman et al., "Pregnancy-Associated Glycoprotein (PAG) Profiles During the Peri-Implantation Period in Recipients Carrying Bovine Somatic Clones: Preliminary Results," *Reprod. Fert. Develop.* (2005) (Abstract).
Im et al., "High Osmolarity at Early Culture Stage Improves in Vitro Development of Pre-Implantation Porcine Nuclear Transfer Embryos," *Reprod. Fert. Develop.* (2005) (Abstract).
International Search Report, from prior PCT Application No. PCT/US2008/064004, (mailed Nov. 14, 2008).
Jakobsen et al., "Chromosome Abnormalities in Bovine Nuclear Transfer Embryos Produced by "Handmade Cloning" ", *Reprod. Fert. Develop.* (2005) (Abstract).
Kasamatsu et al., "Characterization of Early $G_1$ Cells as Nuclear Donors for Somatic Cell Cloning in Cattle," *Reprod. Fert. Develop.* (2005) (Abstract).

(Continued)

*Primary Examiner* — Deborah Crouch
(74) *Attorney, Agent, or Firm* — Klarquist Sparkman, LLP

(57) ABSTRACT

Purified totipotent stem cells and pluripotent stems cells derived by somatic cell nuclear transfer are disclosed herein, as well as cell lines, multipotent cells and differentiated cells produced from these stem cells. The stem cells are produced from an enucleated host cell from a first donor and nuclear genetic material from a somatic cell of a second donor. Methods for making and using such compositions of such stem cells are also provided.

17 Claims, 14 Drawing Sheets

OTHER PUBLICATIONS

Kim et al., "Effect of Cell Types and Passages on Development and Apoptosis of Porcine Cloned Embryos," *Reprod. Fert. Develop.* (2005) (Abstract).

Kurome et al., "Production of Cloned Pigs from Somatic Stem Cells Derived from Salivary Gland," *Reprod. Fert. Develop.* (2005) (Abstract).

Kurosaka and McLaughlin, "DNA Synthesis, Preimplantation Development and Oct-4 Expression of Bovine Clones Reconstructed with Oocytes Preactivated or Enucleated after Spindle Disassembly," *Reprod. Fert. Develop.* (2005) (Abstract).

Lee et al., "Analysis of Differentially Expressed Proteins in the Placenta of Somatic Cell Cloned and Artificial Insemination Pig Placenta Using Proteomics," *Reprod. Fert. Develop.* (2005) (Abstract).

Lee et al., "Efficient Transfection of Plasmid DNA into Cells for Use as Nuclear Donors," *Reprod. Fert. Develop.* (2005) (Abstract).

Lee et al., "Improved Development of Bovine Nuclear Transfer Embryos by the Treatment of Nuclear Donor Cells with Apoptosis Inhibitors During Serum Starvation," *Reprod. Fert. Develop.* (2005) (Abstract).

Liu et al., "A reliable, noninvasive technique for spindle imaging and enucleation of mammalian oocytes," *Nature Biotechnology*, 18:223-225, (2000).

Liu et al., "Chromatin and Cytoskeletal Reorganization of Rabbit Oocytes After Cumulus Cell Nuclear Transfer," *Reprod. Fert. Develop.* (2005) (Abstract).

Lonergan et al., "Pregnancy and Fetal Characteristics After Transfer of Vitrified in Vivo and Cloned Bovine Embryos," *Reprod. Fert. Develop.* (2005) (Abstract).

Marfil et al., "Effect of Repeated Cell Freezings on Pregnancy Rate of Bovine Nuclear Transfer Derived Embryos," *Reprod. Fert. Develop.* (2005) (Abstract).

Marques et al., "Investigation of the Effect of Butyrolactone I and Cycloheximide Treatment During in Vitro Maturation of Swine Oocytes," *Reprod. Fert. Develop.* (2005) (Abstract).

Mir et al., "Phenotypic Variation in Cloned Swine is Corrected in the F1 Generation," *Reprod. Fert. Develop.* (2005) (Abstract).

Mitalipov et al., "Nuclear Remodeling after Somatic Cell Nuclear Transfer (SCNT) in the Rhesus Monkey," *Reprod. Fert. Develop.*, 17(2):175-176, (2005) (Abstract).

Mitalipov et al., "Reprogramming Events and Developmental Competence of Rhesus Monkey Embryos Produced by Somatic Cell Nuclear Transfer," *Reprod. Fert. Develop.*, 18(2):181, (2006).

Miyamoto et al., "Cell Cycle Synchronization of Donor Cells at G1 Phase and Developmental Ability of Nuclear Transfer Embryos in Miniature Pigs," *Reprod. Fert. Develop.* (2005) (Abstract).

Morrow et al., "Composition of Allantoic Fluid in Cattle Pregnant with AI-, IVP-, or Nuclear Transfer-Generated Embryos," *Reprod. Fert. Develop.* (2005) (Abstract).

Mtango and Kono, "Nucleus Changes and Development of Porcine Reconstructed (NT) and Parthogenetically Activated (PA) Embryos," *Reprod. Fert. Develop.* (2005) (Abstract).

Narita et al., "Investigation of Cynomolgus Monkey (*Macaca fascicularis*) Fetus Fibroblast Cell Nuclear Transfer," *Reprod. Fert. Develop.* (2005) (Abstract).

Nieminen et al., "Handmade Cloning in Trans-Species NT: Culture Medium has an Effect on the Ability of Reconstructed Bovine-Murine Embryos to Develop Beyond the 8-Cell Stage," *Reprod. Fert. Develop.* (2005) (Abstract).

Numchaisrika et al., "A Preliminary Study of the in Vitro Development of Asian Elephant, Cloned Embryos, Reconstructed Using a Rabbit Recipient Oocyte," *Reprod. Fert. Develop.* (2005) (Abstract).

Overman et al., "Histological Comparisons Between Nuclear Transfer and in Vivo Porcine Embryos," *Reprod. Fert. Develop.* (2005) (Abstract).

Reubinoff et al., "Embryonic stem cell lines from human blastocysts: somatic differentiation in vitro," *Nature Biotechnology*, 18:399-404, (2000),.

Ribas et al., "Cloned Mouse Produced Using a Zona Free Method of Nuclear Transfer," *Reprod. Fert. Develop.* (2005) (Abstract).

Saeki et al., "Relation of Intensity of Gene Expression in Bovine Reconstructed Embryos to Subsequent Development," *Reprod. Fert. Develop.* (2005) (Abstract).

Sage et al., "Improved in Vitro Development of Porcine Embryos Produced by Nuclear Transfer, IVF and Parthenogenesis," *Reprod. Fert. Develop.* (2005) (Abstract).

Sansinena et al., "Ooplasmic Transfer After Interspecies Nuclear Transfer: Presence of Foreign Mitochondria, Pattern of Migration, and Effect on Embryo Development," *Reprod. Fert. Develop.* (2005) (Abstract).

Skrzyszowska and Samiec, "Production of Porcine Nuclear Transfer Embryos Using Fetal Fibroblast Cells Analyzed on Apoptosis," *Reprod. Fert. Develop.* (2005) (Abstract).

Su et al., "In Vitro Development of Yak (*Poephagus mutus*) Cloned Embryos by Interspecies Somatic Nuclear Transfer," *Reprod. Fert. Develop.* (2005) (Abstract).

Sung et al., "Premature Chromosome Condensation Is Not Essential for Bovine Somatic Nuclear Reprogramming," *Reprod. Fert. Develop.* (2005) (Abstract).

Tecirlioglu et al., "Reproductive Performance of Cloned Bulls," *Reprod. Fert. Develop.* (2005) (Abstract).

Thomson et al., "Isolation of a primate embryonic stem cell line," *Proc. Natl. Acad. Sci.*, 92:7844-7848, (Aug. 1995).

Tomii et al., "Production of Cloned Pigs by Nuclear Transfer of Preadipocytes," *Reprod. Fert. Develop.* (2005) (Abstract).

Troskie et al., "Reconstructed Bovine Blastocysts Comprising Nuclear Transfer-Derived Inner Cell Mass and Trophectoderm from IVF Embryos Do Not Improve in Vivo Development of Clones," *Reprod. Fert. Develop.* (2005) (Abstract).

Tveden-Nyborg et al., "Developmental Delay of Pre-Implantation Ovine in Vitro Cultured and Somatic Cell Nuclear Transfer Embryos," *Reprod. Fert. Develop.* (2005) (Abstract).

Uoc et al., "Somatic Cell Nuclear Transfer in Non-Human Primates: The Possibility of Using Oocytes Matured in Vitro for up to 3 Days as Host Ooplasts," *Reprod. Fert. Develop.* (2005) (Abstract).

Urakawa et al., "Effect of Cell Cycle Phase of Gene-Manipulated Fetal Fibroblasts on the Development of Cloned Bovine Embryos," *Reprod. Fert. Develop.* (2005) (Abstract).

Wee et al., "Abnormal Reprogramming of Histone Acetylation in Cloned Bovine Embryos," *Reprod. Fert. Develop.* (2005) (Abstract).

Williamson et al., "Anatomical Abnormalities in Calves Produced by Nuclear Transfer," *Reprod. Fert. Develop.* (2005) (Abstract).

Xu et al., "Feeder-free growth of undifferentiated human embryonic stem cells," *Nature*, 19:971-974, (Oct. 2001).

Yang et al., "Rabbit Nuclear Transfer With Cultured Somatic Cells," *Reprod. Fert. Develop.* (2005) (Abstract).

Zhao et al., "Production of Cloned Bovine Transgenic Embryos With Various Types of Mono-Colony Cells and Ovum Pickup," *Reprod. Fert. Develop.* (2005) (Abstract).

Zhou et al., "A Comparative Approach to Somatic Cell Nuclear Transfer in the Rhesus Monkey," *Human Reprod.*, 21:2564-2571, (2006).

\* cited by examiner

Ec : Ectoderm represented by neuroepithelial rosettes
Me: Mesoderm represented by fibrous connective tissue, cartilage and smooth muscles cells (Sm)
En : Endoderm represented by cystic and densly packed areas lined with cuboidal and pseudo-stratified coulmnar epithelum

SEQUENCE LISTING

<160> NUMBER OF SEQ ID NOS: 106

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 1
gtggtctcct ccgacttcaa ca                                              22

<210> SEQ ID NO 2
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 2
gtctctctct tcctcttgtg ctct                                            24

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 3
gtcattgctg aaaccgagaa tg                                              22

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 4
gcaaagtact ggatgacacg ct                                              22

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 5
gaaccagagg ggagagacag ag                                              22

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 6
ccctcagctt gcttttagg ag                                               22

<210> SEQ ID NO 7
<211> LENGTH: 20
<212> TYPE: DNA

```
<213> ORGANISM: Artificial sequence
<220> FEATURE:
<223> OTHER INFORMATION: Synthetic oligonucleotide primer.

<400> SEQUENCE: 7
tggctacagc tgcactgccg                                              20

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide primer.

<400> SEQUENCE: 8
ggatccatgc agcgtggac                                               19

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 9
acagagttta ttgaggtgcc cc                                           22

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 10
aaggtgaagt gtcccagagg                                              20

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 11
ggcagcggaa gaggatgctg aa                                           22

<210> SEQ ID NO 12
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 12
gaggcaccaa gttgggcatg aacga                                        25

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 13
acccgttctc catcaacaac ctca                                         24
```

```
<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 14
aagtgtgacc ctctgtttgg gaca                                              24

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 15
tgggaaatgg ctcgtcattt                                                   20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 16
cttcatggaa gcggccactt                                                   20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 17
gccctgacca ctccagttta                                                   20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 18
ggagtcctgg atttccttcc                                                   20

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 19
accaaagctc acgcgtggaa a                                                 21

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide primer.
```

```
<400> SEQUENCE: 20
tgatgtgtct ctcggtcaag tt                                          22

<210> SEQ ID NO 21
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 21
catggcacgt cccaacaaat tcct                                        24

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 22
aaggatgctc cagctggtct ttca                                        24

<210> SEQ ID NO 23
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 23
attccaggaa atctgggaag ccgt                                        24

<210> SEQ ID NO 24
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 24
tccagcatat tctgcacttc accc                                        24

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 25
gttactgggc ggagttcgta                                             20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 26
tgaagtggct tggtgtcttg                                             20

<210> SEQ ID NO 27
<211> LENGTH: 27
<212> TYPE: DNA
```

```
<213> ORGANISM: Artificial sequence
<220> FEATURE:
<223> OTHER INFORMATION: Synthetic oligonucleotide primer.

<400> SEQUENCE: 27
atgttaggat ggatgaaact gagatta                                              27

<210> SEQ ID NO 28
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 28
ccatggaaat ttatctgtga ttctact                                              27

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 29
aagagaggct atcgagatgg a                                                    21

<210> SEQ ID NO 30
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 30
cgttcacttc cactgccact tctg                                                 24

<210> SEQ ID NO 31
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 31
taatgtgcca gataccatgc tggg                                                 24

<210> SEQ ID NO 32
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 32
acttaacctc accagtaaag tcttgat                                              27

<210> SEQ ID NO 33
<211> LENGTH: 37
<212> TYPE: DNA
<213> ORGANISM: Artificial sequence
<220> FEATURE:
<223> OTHER INFORMATION: Synthetic oligonucleotide primer.

<400> SEQUENCE: 33
ggtttttgag ggtgagggtg agggtgaggg tgagggt                                   37
```

<210> SEQ ID NO 34
<211> LENGTH: 39
<212> TYPE: DNA
<213> ORGANISM: Artificial sequence
<220> FEATURE:
<223> OTHER INFORMATION: Synthetic oligonucleotide primer.

<400> SEQUENCE: 34
tcccgactat ccctatccct atccctatcc ctatccta                     39

<210> SEQ ID NO 35
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 35
cagcaagtgg gaaggtgtaa tcc                                     23

<210> SEQ ID NO 36
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 36
cccattctat catcaacggg tacaa                                   25

<210> SEQ ID NO 37
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 37
agtacaacac catgctgggc tat                                     23

<210> SEQ ID NO 38
<211> LENGTH: 15
<212> TYPE: DNA
<213> ORGANISM: Artificial sequence
<220> FEATURE:
<223> OTHER INFORMATION: Synthetic oligonucleotide primer.

<400> SEQUENCE: 38
tgctggccgc atgga                                              15

<210> SEQ ID NO 39
<211> LENGTH: 14
<212> TYPE: DNA
<213> ORGANISM: Artificial sequence
<220> FEATURE:
<223> OTHER INFORMATION: Synthetic oligonucleotide primer.

<400> SEQUENCE: 39
agaggcacct ggcc                                               14

<210> SEQ ID NO 40
<211> LENGTH: 19
<212> TYPE: DNA
<213> ORGANISM: Artificial sequence
<220> FEATURE:
<223> OTHER INFORMATION: Synthetic oligonucleotide primer.

```
<400> SEQUENCE: 40
acccaaaacc tggcgagat                                              19

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 41
tccaggtcgg tctgggtaac                                             20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 42
agtaatgatc ccataacatt                                             20

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 43
aagcaaccag agcgtgaaga a                                           21

<210> SEQ ID NO 44
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 44
tccccacgca gcaacac                                                17

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide primer.

<400> SEQUENCE: 45
agcgggtttt gggtct                                                 16

<210> SEQ ID NO 46
<211> LENGTH: 19
<212> TYPE: DNA
<213> ORGANISM: Artificial sequence
<220> FEATURE:
<223> OTHER INFORMATION: Synthetic oligonucleotide primer.

<400> SEQUENCE: 46 cctcccccgac tctgtttcc                                             19

<210> SEQ ID NO 47
<211> LENGTH: 21
<212> TYPE: DNA
```

```
<213> ORGANISM: Artificial sequence
<220> FEATURE:
<223> OTHER INFORMATION: Synthetic oligonucleotide primer.

<400> SEQUENCE: 47
cacaactcca accagtgcaa a                                              21

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide primer.

<400> SEQUENCE: 48
ccgtcccttc tgaatt                                                    16

<210> SEQ ID NO 49
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 49
gtcggcccag ccagagt                                                   17

<210> SEQ ID NO 50
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 50
cggctaccat catctccatt g                                              21

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide primer.

<400> SEQUENCE: 51
aggaaggagt ttggcc                                                    16

<210> SEQ ID NO 52
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 52
tgtctccgag gactagccaa gt                                             22

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 53
gccctggtga ggatcagaaa                                                20
```

```
<210> SEQ ID NO 54
<211> LENGTH: 15
<212> TYPE: DNA
<213> ORGANISM: Artificial sequence
<220> FEATURE:
<223> OTHER INFORMATION: Synthetic oligonucleotide primer.

<400> SEQUENCE: 54
tggaggcaga tgaat                                                    15

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 55
gaaggagaac aaggagttga tgaag                                         25

<210> SEQ ID NO 56
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 56
cctccacaac cagctgaaaa a                                             21

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide primer.

<400> SEQUENCE: 57
aggtgtttcc aaagaa                                                   16

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 58
cccttcgaga gcaagtggaa                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 59
gcggagctcg atgtcatcat                                               20

<210> SEQ ID NO 60
<211> LENGTH: 15
<212> TYPE: DNA
<213> ORGANISM: Artificial sequence
<220> FEATURE:
<223> OTHER INFORMATION: Synthetic oligonucleotide primer.
```

<400> SEQUENCE: 60
ccacccctga ggatg                                                    15

<210> SEQ ID NO 61
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 61
gcccggccaa cgtgtac                                                  17

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide primer.

<400> SEQUENCE: 62
accgccggca cgaagt                                                   16

<210> SEQ ID NO 63
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 63
ttgtcttcat cgcgctgc                                                 18

<210> SEQ ID NO 64
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 64
catctacgat ggagcgtctt gtc                                           23

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 65
gctggtgcgc acaagtactg                                               20

<210> SEQ ID NO 66
<211> LENGTH: 13
<212> TYPE: DNA
<213> ORGANISM: Artificial sequence
<220> FEATURE:
<223> OTHER INFORMATION: Synthetic oligonucleotide primer.

<400> SEQUENCE: 66
ccgtgggacc ttc                                                      13

<210> SEQ ID NO 67
<211> LENGTH: 22
<212> TYPE: DNA

```
<213> ORGANISM: Artificial sequence
<220> FEATURE:
<223> OTHER INFORMATION: Synthetic oligonucleotide primer.

<400> SEQUENCE: 67
accaaccagc cagagaaaga ag                                              22

<210> SEQ ID NO 68
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 68
ttggtttgcc attcaccatt c                                               21

<210> SEQ ID NO 69
<211> LENGTH: 14
<212> TYPE: DNA
<213> ORGANISM: Artificial sequence
<220> FEATURE:
<223> OTHER INFORMATION: Synthetic oligonucleotide primer.

<400> SEQUENCE: 69
cacctcgggc tcgg                                                       14

<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 70
tggccagcag cagctaca                                                   18

<210> SEQ ID NO 71
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 71
tcctgcaggc ggttggt                                                    17

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide primer.

<400> SEQUENCE: 72
tcatccggga ggacaa                                                     16

<210> SEQ ID NO 73
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 73
cagggcccct tcgaaaga                                                   18
```

<210> SEQ ID NO 74
<211> LENGTH: 19
<212> TYPE: DNA
<213> ORGANISM: Artificial sequence
<220> FEATURE:
<223> OTHER INFORMATION: Synthetic oligonucleotide primer.

<400> SEQUENCE: 74
ctgccttggg agcacagaa                                            19

<210> SEQ ID NO 75
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 75
cgcatgatct ttgctgc                                              17

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 76
cctgcccttc actcatggaa                                           20

<210> SEQ ID NO 77
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 77
ggtagaagat acgcagtccc ttgt                                      24

<210> SEQ ID NO 78
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 78
tcttcaggca agttttt                                              17

<210> SEQ ID NO 79
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 79
caagcaccag tcgaggtcta aa                                        22

<210> SEQ ID NO 80
<211> LENGTH: 17
<212> TYPE: DNA
<213> ORGANISM: Artificial sequence
<220> FEATURE:
<223> OTHER INFORMATION: Synthetic oligonucleotide primer.

```
<400> SEQUENCE: 80
cgccggtggg ttgattt                                                    17

<210> SEQ ID NO 81
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 81
actatgcctg aagccaa                                                    17

<210> SEQ ID NO 82
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 82
gagcgcaccg gcaagtac                                                   18

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 83
cagcggaagt cgatctcctt                                                 20

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 84
tgtacttcac catcgtca                                                   18

<210> SEQ ID NO 85
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 85
cccggcctgg tgttcag                                                    17

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 86
ggccttggtc agcatgct                                                   18

<210> SEQ ID NO 87
<211> LENGTH: 15
<212> TYPE: DNA
```

```
<213> ORGANISM: Artificial sequence
<220> FEATURE:
<223> OTHER INFORMATION: Synthetic oligonucleotide primer.

<400> SEQUENCE: 87
tctgcacact caatg                                                    15

<210> SEQ ID NO 88
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 88
cctcactcag tccgttcttt ca                                            22

<210> SEQ ID NO 89
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 89
ggctccatgt ctctgcttct g                                             21

<210> SEQ ID NO 90
<211> LENGTH: 15
<212> TYPE: DNA
<213> ORGANISM: Artificial sequence
<220> FEATURE:
<223> OTHER INFORMATION: Synthetic oligonucleotide primer.

<400> SEQUENCE: 90
tggtgaccgg gactg                                                    15

<210> SEQ ID NO 91
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 91
ccagcacggc caagtca                                                  17

<210> SEQ ID NO 92
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 92
cttggcgatc tggcagtaga g                                             21

<210> SEQ ID NO 93
<211> LENGTH: 14
<212> TYPE: DNA
<213> ORGANISM: Artificial sequence
<220> FEATURE:
<223> OTHER INFORMATION: Synthetic oligonucleotide primer.

<400> SEQUENCE: 93
ctggacgtac tccc                                                     14
```

```
<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 94
ggtggtctcc tccgacttca                                              20

<210> SEQ ID NO 95
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 95
accaggaaat gagcttgaca aag                                          23

<210> SEQ ID NO 96
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 96
cccactcttc caccttcgac gctg                                         24

<210> SEQ ID NO 97
<211> LENGTH: 17
<212> TYPE: DNA
<213> ORGANISM: Artificial sequence
<220> FEATURE:
<223> OTHER INFORMATION: Synthetic oligonucleotide primer.

<400> SEQUENCE: 97
cccactggtg ccgtgaa                                                 17

<210> SEQ ID NO 98
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 98
ttggcaaatt gctcgagttc t                                            21

<210> SEQ ID NO 99
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 99
ggactcctcc gggttttgct ccag                                         24

<210> SEQ ID NO 100
<211> LENGTH: 21
<212> TYPE: DNA
<213> ORGANISM: Artificial sequence
<220> FEATURE:
<223> OTHER INFORMATION: Synthetic oligonucleotide primer.
```

```
<400> SEQUENCE: 100
ccatgctggg tgctagagct a                                          21

<210> SEQ ID NO 101
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 101
ccattgacat ttgtatcatg ctttagt                                    27

<210> SEQ ID NO 102
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 102
aggtgcatat taaagtgc                                              18

<210> SEQ ID NO 103
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 103
attccaggca gtaccaaaca g                                          21

<210> SEQ ID NO 104
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 104
ccatcagggc caataattat t                                          21

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 105
ctgaatgaac tgcaggacga                                            20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 106
agccaacgct atgtcctgat                                            20
```

PRIMATE PLURIPOTENT STEM CELLS PRODUCED BY SOMATIC CELL NUCLEAR TRANSFER

PRIORITY CLAIM

This claims the benefit of U.S. Provisional Application No. 60/938,683, filed May 17, 2007; U.S. Provisional Application No. 60/940,316, filed May 25, 2007; and U.S. provisional Application No. 60/942,427, filed Jun. 6, 2007. The prior provisional applications are all incorporated by reference herein in their entirety.

STATEMENT OF GOVERNMENT SUPPORT

This invention was made with United States government support pursuant to grants R01-NS044330-04, P51-RR0013-47, and P51-RR00163-47 from the National Institutes of Health; the United States government has certain rights in the invention.

FIELD OF THE INVENTION

This invention relates to primate totipotent stem cells, pluripotent stem cells and cell lines thereof, derived by somatic cell nuclear transfer, and methods of making and using thereof.

BACKGROUND

Embryonic stem cells (ESCs) have been widely described in the literature. ESC lines can proliferate indefinitely in an undifferentiated state in vitro. These cells are more accurately described as pluripotent stem cells (PSCs), meaning that they can be stimulated to generate any and all of the cell types present in an organism (e.g., bone cells, muscle cells, brain cells) under suitable differentiation conditions in vitro. PSCs have been isolated from the inner cell mass of the developing murine blastocyst (Evans et al., *Nature* 292:154-156, 1981; Martin et al., *Proc. Natl. Acad. Sci. U.S.A.* 78:7634-7636, 1981; Robertson et al., *Nature* 323:445-448, 1986; Doetschman et al., *Nature* 330:576-578, 1987; and Thomas et al., *Cell* 51:503-512, 1987; U.S. Pat. No. 5,670,372). Additionally, non-human primate and human cells with PSC properties have been isolated from the inner cell mass of blastocysts (Thomson et al., *Proc Natl Acad Sci USA.* 92(17):7844-8, 1995; Thomson et al., *Science* 282:1145-1147, 1998) and developing germ cells (Shamblott et al., *Proc. Natl. Acad. Sci. U.S.A.* 95:13726-13731, 1998) (see also U.S. Pat. No. 6,090,622, PCT Publication No. WO 00/70021 and PCT Publication No. WO 00/27995). Human ESC markers have been described, for example, Stage Specific Embryonic Antigen (SSEA)-3, SSEA-4, TRA-1-80 and Octomer-binding transcription factor (OCT)-4, a homeodomain transcription factor.

Transfer of nuclear material from a somatic cell into an enucleated host oocyte is known as somatic cell nuclear transfer (SCNT). SCNT dates back to 1962 when John Gurdon first demonstrated that a differentiated vertebrate somatic cell nucleus (from a larval stage intestinal epithelial cell) could be reprogrammed back into an undifferentiated state after being transferred into an enucleated *Xenopus laevis* egg and elicit the development of a cloned adult frog (Gurdon, *J. Embryol. Exp. Morph.* 10: 622-640, 1962).

Nuclear transfer using embryonic blastomeres (i.e., non-somatic cells) as the source of donor nuclei has been successfully used to produce primates (Meng et al., *Biol Reprod* 57(2): 454-9, 1997; Mitalipov et al., *Biol Reprod* 66, 1367-73 (2002). However, despite the remarkable progress achieved in the past decade in mammalian SCNT, to date, it has not been possible to obtain non-human primate or human totipotent stem cells (TSCs) that are capable of resulting in a viable fetus or developing into a blastocyst in vitro that subsequently acts as a source of functional PSCs using SCNT. The ability to generate primate, especially human, TSCs and PSCs progeny by SCNT would be useful for many medical purposes, such as autologous transplantation to individuals in need thereof without immunorejection. Accordingly, there remains a long and unfulfilled need to achieve the goal of obtaining pluripotent ESCs by SCNT in primates including, in particular, humans.

SUMMARY

Methods are disclosed herein for efficiently generating totipotent and pluripotent primate stem cells using SCNT. The TSCs and PSCs are produced using an enucleated host cell from a first primate donor and nuclear genetic material from a somatic cell of a second primate donor. The first primate and the second primate are different individuals from the same species. In one embodiment, a method is provided for producing a primate TSCs and PSCs, comprising the steps of: (a) enucleating a recipient primate host cell from a first primate in a manner that does not lower levels of maturation promoting factor (MPF) to form an enucleated cell; and (b) introducing a nucleus of a donor primate somatic cell from a second primate into the enucleated cell, wherein the introduction of nucleus is performed under conditions that reduce or eliminate calcium oscillations, wherein the first primate and the second primate are from the same primate species. These methods produce a primate embryonic cells that are totipotent, wherein the cells are (i) capable of 4 or more cell divisions; (ii) maintains a normal karyotype while in culture; (iii) capable of differentiating into any somatic cell lineage (endoderm, mesoderm and ectoderm cells) and germ cells; and (iv) comprises mitochondrial DNA derived from the first primate recipient and nuclear genetic material derived from the donor primate somatic cell of a second primate.

Totipotent and pluripotent primate stem cells are also disclosed herein. In one embodiment, the PSCs are capable of four or more cell divisions in vitro, and maintain a normal karyotype when propagated in vitro and/or when cultured into more differentiated cells for transfer into a primate recipient, i.e., multipotent cells. These cells include mitochondrial DNA from the recipient enucleated cell and nuclear genetic material from the donor somatic cells.

The foregoing and other features and advantages will become more apparent from the following detailed description of several embodiments, which proceeds with reference to the accompanying figures.

BRIEF DESCRIPTION OF THE DRAWINGS

FIG. 3A is a set of digital images of spindle visualization in monkey oocytes and morphology and Oct-4 protein profiles of SCNT blastocysts. a; Spindle (indicated by arrow) detection in monkey MII oocytes prior to removal using the Oosight™ imaging system. b; Morphology of day 8, hatching reconstructed blastocysts produced from donor fetal fibroblasts. c-c1; An expanded, reconstructed blastocyst displaying strong Oct-4 protein signal in the ICM but not in the trophectoderm. Oct-4 expression indicates that the donor nucleus was reprogrammed to a totipotent state. d-d1; Aberrant nuclear reprogramming in a hatching, reconstructed blastocyst with only a few ICM cells appearing Oct-4 positive. FIG. 3B is a digital image of PCR-based sexing of gDNA isolated from SCNT blastocysts based on size differences in the amplicons of the X- and Y-linked zinc finger protein genes (ZFX and ZFY. The use of male donor cells resulted in the production of male, reconstructed blastocysts eliminating the possibility of a parthenogenetic origin. Lanes 1-2 (ICSI-1 and ICSI-2) are individual male and female control blastocysts, respectively, produced by ICSI; Lane 3 (HPRT1−) represents HPRT1−, adult male fibroblasts; Lanes 4-5 (SCNT-1 and SCNT-2) are individual blastocysts reconstructed from HPRT1−, adult male fibroblasts; Lanes 6-7 (OR-6 and OR-3) are female and male rhesus monkey embryonic stem cell lines, respectively, produced from ICSI-produced blastocysts (ORMES series).

FIG. 7A is a digital image of G-banding analysis of the CRES-2 cell line demonstrating a normal euploid rhesus monkey karyotype (42, XY). FIG. 7B is a digital image of a G-banding analysis of the CRES-1 cell line with aneuploid karyotype, characterized by an isochromosome comprised of two copies of the long arm of the Y chromosome (41,X[3]/42,X,i(Y)q10)[17]). FIG. 7C is a digital image of fluorescent in situ hybridization (FISH) analysis of the Male #1 fibroblasts (used as the nuclear donor cells for CRES-1 and CRES-2) demonstrating a normal karyotype (42, XY). The arrow indicates the presence of two fluorescent red signals on the long (q) arm of the Y chromosome. FIG. 7D is a digital image of FISH analysis of CRES-1 cells. The arrow indicates the presence of four signals for the Y chromosome long (q) arm, instead of the usual two, confirming the presence of the i(Y)(q10) aneuploidy observed in the G-band study.

FIG. 11A: Ectoderm (Ec) derived neuroepithelial rosettes and neural tissues. FIG. 11B: Mesoderm (Me) originated connective tissues and cartilage. Endoderm (En) is represented by cystic areas lined with cuboidal epithelium. FIG. 11C: Ectoderm derived neuroepithelial rosettes and neural tissues. Cystic areas lined with cuboidal epithelium represents the endoderm layer. FIG. 11D: Ectoderm derived neuroepithelium-rosettes and neural tissues. FIG. 11E: Mesoderm originated connective tissues, cartilage and smooth muscle (Sm). Panel F: mesoderm originated connective tissues and endoderm (Ec) derived densely packed areas lined with pseudo-stratified columnar epithelium. All panels are stained with Haematoxylin and Eosin (H&E) and images were captured at X100 magnification.

FIG. 12a: RT-PCR analysis of EBs during culture for 3-50 days; FIG. 12b: immunostaining of CRES-3-derived differentiated cultures with VASA and OCT4 antibody after 4 weeks of differentiation. In FIG. 12b, the images labeled A, B and C represent the same image with phase contrast, DAPI staining (all cell nuclei) and VASA expression, respectively. D, E and F are phase contrast, DAPI staining and OCT4 signal.

SEQUENCE LISTING

Figure 1:
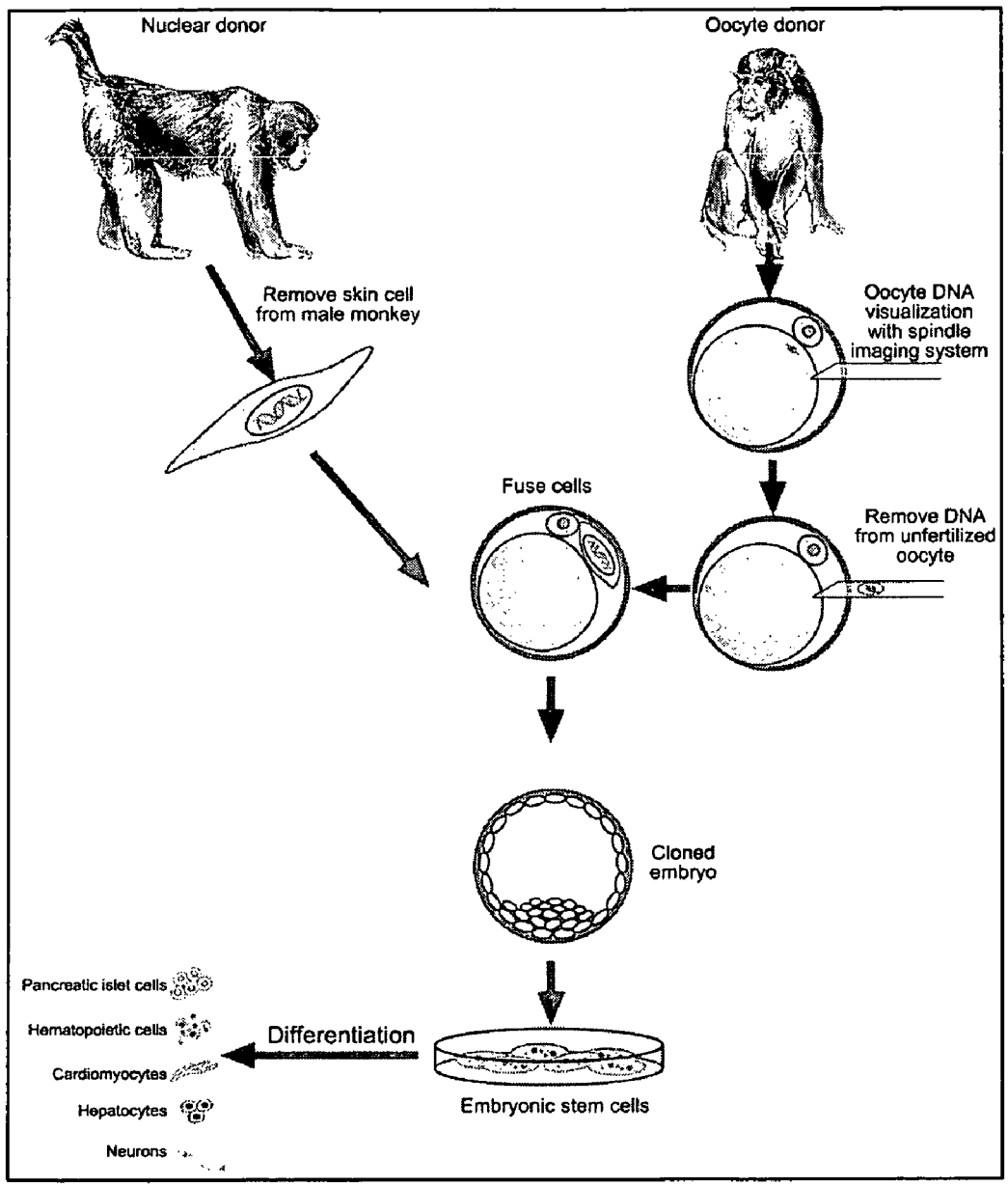
FIG. 1 is a schematic diagram showing experimental steps of reprogramming adult primate somatic cells into pluripotent embryonic stem cells. A donor nucleus from an exemplary somatic cell (skin cell) was introduced into an enucleated oocyte and the resulting embryo gave rise to embryonic stem cells. It should be noted that injection can be used instead of fusion to introduce the somatic cell nucleus. The embryonic stem cells could then be differentiated into cells of different lineages, including pancreatic islet cells, hematopoietic cells, cardiomyocytes, hepatocytes and neurons.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOS: 1-106 are the nucleic acid sequences of primers.

DETAILED DESCRIPTION

Primate TSCs produced by SCNT and PSCs produced from these TSCs are disclosed herein. Methods for generating and using these TSCs and PSCs are also disclosed herein.

Unless defined otherwise, all technical and scientific terms used herein have the same meaning as is commonly understood by one of ordinary skill in the art to which this invention belongs. All patents, published patent applications and other publications and sequences from GENBANK® and other databases referred to herein also are incorporated by reference in their entirety.

If a definition set forth in this section is contrary to or otherwise inconsistent with a definition set forth in patents, published patent applications and other publications and sequences from GENBANK® and other databases that are herein incorporated by reference, the definition set forth in this section prevails over the definition that is incorporated herein by reference.

Ng et al. reported in 2004 that the introduction of entire fibroblast cells (fetal and adult, including the cytoplasm and the nucleus of the fibroblast), from two species of macaques (long tail and lion tail) into enucleated oocytes from the long tail macaque. In some cases this cell transfer resulted in reprogramming of the somatic cell nucleus to the point that the resulting cell exhibited at least some properties of an embryo. Blastomeres resulting from 2-3 cell divisions (4-8 cells) were produced. However, Ng et al. did not culture these cells to the blastocyst stage. The blastomeres (4-8 cells) were implanted into female long tail macaques and resulting pregnancies were monitored by ultrasound observation of the gestational sac development and fetal heartbeat. However, the implanted cells were not totipotent as no pregnancy went to term (the longest was 60 days).

More recently, SCNT embryos were purportedly created in humans following the transfer of skin fibroblast nuclei, with subsequent isolation of ESCs (Hwang, Ryu et al. 2004). In 2005, Hwang and colleagues claimed the derivation of patient-specific ESC lines by SCNT (Hwang, Roh et al. 2005). However, in January 2006, the Seoul National University Investigation Committee discredited Hwang's claims and the editors of Science announced their intention to unconditionally retract both papers (Kennedy 2006).

TSCs generated using SCNT can be used to produce a blastocyst in vitro. The ICM of this blastocyst can then be used as a source of PSCs. While a blastocyst can be generated using sperm-fertilized oocytes, a major limitation for the medical use of cells subsequently derived from this blastocyst is that the cells usually are rejected in an individual to whom they are to be administered due to their allogeneic nature in the absence of immunosuppressive therapy. A major issue that must be addressed in the transplant model is the nature and degree of the immune response following the transplantation of PSC progeny (Dawson, Bateman-House et al. 2003; Ginis and Rao 2003). Differentiated PSC-derived cells express major histocompatibility complex I (MHC-I) antigens (Drukker, Katz et al. 2002) and transplantation of such cells into genetically unrelated patients (without immunosuppressive drugs) may incite an immune response and result in rejection. Even using an extensive daily cocktail of immunosuppressive drugs, the majority of heart transplant patients will undergo at least one episode of graft rejection within their first year, requiring increased amounts of immunosuppressive drugs, increasing the patient's risk of infection, cancer, or early death (Hunt 2001). U.S. Pat. No. 6,808,704 discloses methods of making immune compatible tissues and cells for purposes of transplantation and tissue engineering in cows and goats.

Therefore, it is important to have a source of PSCs and their progeny, i.e., transplantable cells, other than from blastocysts obtained by conventional in vitro fertilization because of the limitations arising from the immune response in transplantation. Autologous PSCs will not be rejected in a recipient individual. Thus the ability to produce authologous cells of any cell type provides invaluable tools with enormous promise for cell-based regenerative medicine.

The autologous TSCs, PSCs, and their progeny provided herein offer a source of transplantable cells to circumvent or reduce the likelihood of rejection.

General Techniques

The practice of the present invention will employ, unless otherwise indicated, conventional techniques of stem cell biology, cell culturing, molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Animal Cell Culture* (R. I. Freshney), ed., 1987); *Methods in Enzymology* (Academic Press, Inc.); *Handbook of Experimental Immunology* (D. M. Weir &C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) *Short Protocols in Molecular Biology* (Wiley and Sons, 1999), *Embryonic Stem Cells: A Practical Approach* (Notaranni et al. eds., Oxford University Press 2006); and *Essential of Stem Cell Biology* (R. Lanza, ed., Elsevier Academic Press 2006).

DEFINITIONS

The term "nuclear genetic material" refers to structures and/or molecules found in the nucleus which comprise polynucleotides (e.g., DNA) which encode information about the individual. Nuclear genetic material includes, but is not limited to, chromosomes and chromatin. The term includes nuclear genetic material produced by cell division such as the division or a parental cell into daughter cells. Thus, a cell includes nuclear genetic material derived from a donor somatic cell if the cell has been produced during mitosis or meiosis from an original cell, or if the nuclear genetic material has been transferred into an enucleated cytoplast via somatic cell nuclear transfer. The term "mitochondrial DNA" or "mtDNA" refers to the DNA of the mitochondrion, a structure situated in the cytoplasm of the cell rather than in the nucleus (where all the other chromosomes are located). In vivo, all mtDNA is inherited from the mother. There are 2 to 10 copies of the mtDNA genome in each mitochondrion. mtDNA is a double-stranded, circular molecule. It is very small relative to the chromosomes in the nucleus and includes only a limited number of genes, such as those encoding a number of the subunits in the mitochondrial respiratory-chain complex and the genes for some ribosomal RNAs and transfer RNAs. A cell includes mtDNA derived from the continued replication cytoplasmically based mitochondria, which in the case of SCNT are based in the recipient cytoplast.

The term "DNA methylation" refers to the postsynthetic addition of methyl groups to specific sites on DNA molecules; the reaction is catalyzed by enzymes called DNA methyltransferases that are specific for nucleotide and position of methylation. In eukaryotes, methylation is involved in gene expression, and plays a role in a variety of epigenetic mechanisms, including development, X chromosome inactivation, genomic imprinting, mutability of DNA, and uncontrolled cell growth in cancer. The term "X chromosome inactivation" refers to the inactivation of one of each pair of X chromosomes to form the Barr body in female mammalian somatic cells. Thus tissues whose original zygote carried heterozygous X borne genes should have individual cells expressing one or other but not both of the X encoded gene products. The inactivation is thought to occur early in development and leads to mosaicism of expression of such genes in the body.

The phrase "dosage compensation" refers to a mechanism that sense gene dosage and regulates expression accordingly. In mammals there is monoallelic expression of X-linked genes that differ in dose between females (XX) and males (XY). "XIST" refers to a gene encoding a large non-coding RNA which has been shown to be necessary for developmentally regulated X chromosome silencing in females. The XIST RNA is about 18 kb and is not translated, it is spliced, and polyadenylated. It is also organized into blocks of repetitive sequence. In vivo, XIST RNA is found to be stably associated with the silenced X chromosome. The expression of XIST RNA is always cis-limited, and is associated with the silenced X chromosome in females.

The term "effective amount" or "therapeutically effective amount" refers to the amount of agent or a cell that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount of a cell or an agent to sufficient reduce or eliminate a symptom of a disease. In another embodiment, a therapeutically effective amount is an amount sufficient to overcome the disease itself.

As used herein, the term "preparation," "purified preparation," "isolated preparation," "isolated poplation" or "purified population" of totipotent or pluripotent primate cells refers to a preparation of one or more cells that has been manipulated to provide a preparation of cells that is substantially free of additional components. In some embodiments, the cell preparation is at least about 60%, by weight or number, free from other components that are present when the cell is produced, such as other types of cells. In various embodiments, the cell is at least about 75%, or at least about 85%, or at least about 90%, or at least about 95%, or at least about 99%, by weight or number, pure. A purified cell preparation can be obtained, for example, by purification (e.g., extraction) from a natural source, fluorescence-activated cell-sorting, or other techniques known to the skilled artisan. Purity can be assayed by any appropriate method, such as fluorescence-activated cell-sorting (FACS) or by visual examination.

As used herein, the term "totipotent" or "totipotency" refers to a cell's ability to divide and ultimately produce an entire organism including extra embryonic tissues in vivo. In one aspect, the term "totipotent" refers to the ability of the cell to progress through a series of divisions into a blastocyst in vitro. The blastocyst comprises an inner cell mass (ICM) and a trophoblast. The cells found in the ICM give rise to PSCs that possess the ability to proliferate indefinitely, or if properly induced, differentiate in all cell types contributing to an organism. Trophoblast cells generate extra-embryonic tissues, including placenta and amnion.

TSCs are the source of PSCs. As used herein, the term "pluripotent" refers to a cell's potential to differentiate into cells of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent stem cells can give rise to any fetal or adult cell type including germ cells. However, PSCs alone cannot develop into a fetal or adult animal when transplanted in utero because they lack the potential to contribute to extra embryonic tissue (e.g., placenta in vivo or trophoblast in vitro).

PSCs are the source of multipotent stem cells (MPSCs) through spontaneous differentiation or as a result of exposure to differentiation induction conditions in vitro. The term "multipotent" refers to a cell's potential to differentiate and give rise to a limited number of related, different cell types. These cells are characterized by their multi-lineage potential and the ability for self-renewal. In vivo, the pool of MPSCs replenishes the population of mature functionally active cells in the body. Among the exemplary MPSC types are hematopoietic, mesenchymal, or neuronal stem cells.

Transplantable cells include MPSCs and more specialized cell types such as committed progenitors as well as cells further along the differentiation and/or maturation pathway that are partly or fully matured or differentiated. "Committed progenitors" give rise to a fully differentiated cell of a specific cell lineage. Exemplary transplantable cells include pancreatic cells, epithelial cells, cardiac cells, endothelial cells, liver cells, endocrine cells, and the like.

A "feeder layer" refers to non-proliferating cells (such as irradiated cells) that can be used to support proliferation of TSCs and PSCs. Protocols for the production of feeder layers are known in the art, and are available on the internet, such as at the National Stem Cell Resource website, which is maintained by the American Type Culture Collection (ATCC).

"Primate" refers to all animals in the primate order, including monkeys and humans. Exemplary non-human primates include, for example, chimpanzees, rhesus macaques, squirrel monkeys, lemurs. They include Old World, New World, and prosimian monkeys.

As used herein, the term "embryo" refers generally to a cellular mass obtained by one or more divisions of a zygote or an activated oocyte with an artificially reprogrammed nucleus without regard to whether it has been implanted into a female. A "morula" is the preimplantation embryo 3-4 days after fertilization, when it is a solid mass, generally composed of 12-32 cells (blastomeres). A "blastocyst" refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst is generally a sphere made up of a layer of cells (the trophectoderm), a fluid-filled cavity (the blastocoel or blastocyst cavity), and a cluster of cells on the interior (the ICM). The ICM, consisting of undifferentiated cells, gives rise to what will become the fetus if the blastocyst is implanted in a uterus.

"Genomic imprinting" refers to a mammalian epigenetic phenomenon whereby the parental origin of a gene determines whether or not it will be expressed. Over 75 imprinted genes have been identified, many of which are noncoding RNAs that are hypothesized to control the expression of linked protein coding genes that are also imprinted. Generally, allele-specific methylation of CpG dinucleotides is a mechanism that regulates gene expression of imprinted genes. "Maternally expressed" refers to a gene that is expressed from the copy inherited from the mother. Imprinted genes include, but are not limited to the maternally expressed imprinted genes H19, CDKNIC, PHLDA2, DLX5, ATP10A, SLC22A18 or TP73. Paternally expressed imprinted genes include but are not limited to IGF2, NDN, SNRPN, MEST, MAGEL2, and PEG3. Exemplary sequence information for these genes, including the human nucleic acid sequences, can be found at the gene imprint website (©2006), available on the internet; this information is incorporated by reference herein.

Lamin refers to the major non-collagenoous component of the basal laimina. It is a glycoprotein that has an "A" chain and two "B" chains. Lamins are fibrous proteins providing structural function and transcriptional regulation in the cell nucleus. A-type lamins are only expressed following gastrulation. Lamin A and C are the most common A-type lamins and are splice variants of the LMNA gene.

"Maturation promoting factor" (MPF) refers to a heterodimeric protein comprising cyclin B and cyclin-dependent kinase 1 (i.e., p34cdc2) that stimulates the mitotic and meiotic cell cycles. MPF promotes the entrance into mitosis from the G2 phase by phosphorylating multiple proteins needed during mitosis. MPF is activated at the end of G2 by a phosphatase which removes an inhibitory phosphate group added earlier. Targets for MPF include condensing, which enable chromatin condensation; various microtubule-associated proteins involved in mitotic spindle formation; lamins, whose interaction contribute to the degradation of the nuclear envelope as well as the histones, H1 and H3; and the Golgi matrix, to cause fragmentation (Nigg 1993; Szollosi, Czolowska et al., 1988).

Reference to "about" a value or parameter herein includes (and describes) embodiments that are directed to that value or parameter per se. For example, description referring to "about X" includes description of "X."

"Nuclear reprogramming" results in immediate inhibition of transcription in the transferred somatic cell nucleus and the subsequent establishment of temporal and spatial patterns of embryonic gene expression associated with normal development. Currently unidentified reprogramming factors present in oocytes are capable of initiating a cascade of events that can reset the epigenetic program of specialized somatic cells back to an undifferentiated, totipotent state.

"Nuclear remodeling" refers to morphological and biochemical changes in nuclear material occurring soon after introduction of somatic cell nucleus into an enucleated, non-activated, mature oocyte. Nuclear remodeling includes but is not confined to nuclear envelope breakdown (NEBD), followed by premature chromosome condensation (PCC) and spindle formation.

"Nuclear transfer" refers to the insertion of a donor nucleus into an enucleated recipient host cell.

"Telomere" refers to the sequences and the ends of a eukaryotic chromosome, consisting of many repeats of a short DNA sequence in specific orientation. Telomere functions include protecting the ends of the chromosome, so that chromosomes do not end up joined together, and allowing replication of the extreme ends of the chromosomes (by telomerase). The number of repeats of telomeric DNA at the end of a chromosome decreases with age and telomeres may play roles in aging and cancer. "Telomerase" refers to a DNA polymerase involved in the formation of telomeres and the maintenance of telomere sequences during chromosome replication.

Primate Totipotent, Pluripotent and Multipotent Stem Cells

Compositions of primate TSCs or primate PSCs are provided herein, including both monkey and human cells. The PSCs are capable of extended propagation in vitro without losing their ability to differentiate into ectoderm, mesoderm and endoderm. The TSCs and PSCs may have been generated and stored in the course of their use and/or propagation, such as by freezing. These TSCs and PSCs can be isolated, and thus can be propagated in vitro. These TSCs and PSCs can be human cells, or can be non-human primate cells. In one embodiment the TSCs and PSCs are non-human.

In one embodiment, the primate PSCs are capable of proliferating in vitro for at least 4 or more cell divisions in vitro, wherein the PSC maintains its pluripotency. In other embodiments, the PSCs are capable of proliferating at least 5, 6, 7, 8 or more cell divisions, wherein the PSCs maintain their pluripotency. In further embodiments, the TSCs are capable of proliferating at least 5, 6, 7, 8 or more cell divisions, wherein the TSCs maintain their totipotency. TSCs can be produced by transfer of a somatic cell nucleus into an enucleated host cell, such as an enucleated oocyte, zygote (fertilized 1-cell oocyte) or totipotent blastomere. The TSCs can be used to produce a viable embryo and after transfer into a recipient a live offspring. The TSCs can also be used as a source of trophoblast and PSCs which are capable of proliferating in vitro for at least 4 or more cell divisions while maintaining pluripotency.

PSCs are also disclosed herein. In one embodiment, the cells are human PSCs. In another embodiment, the PSCs are non-human primate cells. In one aspect, the PSCs are capable of proliferating in vitro for at least about 1 month or more, while maintaining pluripotency. In additional embodiments, the primate stem cells are capable of proliferating in vitro for at least about 2, 3, or 4 months or more, wherein the cell maintains its pluripotency. In other embodiments, the PSCs are capable of proliferating in vitro for at least about 5, 6, or 7 months or more, wherein the PSCs maintain their pluripotency. In another embodiment, the PSCs are capable of proliferating in vitro for at least about 8 months or more, wherein the PSCs maintains their pluripotency. In a further embodiment, the PSCs are capable of proliferating in vitro for at least about 9 months or more, wherein the PSCs maintain their pluripotency. The methods of obtaining and culturing these cells are provided in greater detail below.

In one aspect, the TSCs provided herein generate a blastocyst comprising an ICM and a trophectoderm (TE). The ICM serves as a source for the PSCs. The TE can serve as a source of trophectodermal stem cells.

In addition, the totipotent and pluripotent primate cells possess any one or more (including all) of the characteristic morphology: high nuclear/cytoplasmic ratios, prominent nucleoli, and compact colony formation. The pluripotent cell can be characterized by the presence of discrete cell surface markers or transcription factor expression that includes one or more (including all) of the following: OCT-4, SSEA-3, SSEA-4, TRA-1-60, and TRA-1-81. These cells are also characterized by mRNA expression of all or one or more (including all) of the following: POU5F1 (OCT4), NANOG, SOX-2, TDGF, THY1, FGF4, TERT and LEFTYA. The cells can also be characterized by the mRNA and/or protein expression of one or more (including all) of nuclear factor (erythroid-derived 2)-like 3 (NFE2L3), nuclear receptor subfamily 5, group A, member 2 (NR5A2), lymphocyte specific protein tyrosine kinase (LCK), V set domain containing T cell activation inhibitor 1 (VTCN1), developmental pluripotency associated 4 (DPPA4), solute carrier family 12 (SLC12A1), C14orf115, myosin VIIA and rab interacting protein (MYRIP), alcohol dehydrogenase 4 (ADH4) and PR-domain containing 14 (PRDM14) (See the GENECARD® website, GENBANK® and iHOP® websites, available on the internet. Exemplary amino acid sequences and nucleic acid sequences are provided in GENBANK® as of May 17, 2007).

In addition to marker and transcription factor expression profiles, the totipotent and pluripotent primate stem cells can also maintain a normal diploid karyotype. Both XX and XY cell lines can be derived. A normal karyotype is one where all chromosomes normally present in a species are present and have not been noticeably altered. Normal karyotype typically refers to the absence of chromosomal translocations, deletions or insertions. The normal karyotype is readily determined by any method known to one of skill in the art, such as any banding technique, such as G-banding and/or fluorescence in situ hybridization (FISH) for detecting translocation. The totipotent and pluripotent primate stem cells disclosed herein have a karyotype that is stable throughout in vitro culturing. In addition, the karyotype remains stable even when the PSCs are cultured to differentiate into organ-specific cells and used for treatment purposes, such as for transplantation.

The TSCs provided herein can be used as a source of PSCs or live offspring. The PSCs can be propagated as a self-renewing cell line as well as provide a renewable source of MPSCs and other transplantable cells. PSCs can differentiate under appropriate conditions into the germ cell lineage and viable gametes and three embryonic germ layers; mesoderm (for example, bone, cartilage, smooth muscle, striated muscle, and hematopoietic cells); endoderm (for example, liver, primitive gut and respiratory epithelium); ectoderm (for example, neurons, glial cells, hair follicles and tooth buds). The TSCs can also produce all of the above cell types but unlike PSCs, TSCs can also generate trophectodermal cells. One of skill in the art is familiar with how to assess the ability of PSCs to differentiate into cells of the three germ layers. In one example, stem cells are implanted into an animal model, such as a nude mouse, and the cells are allowed to grow and form teratomas. After a suitable amount of time, the teratomas are removed, sectioned and stained to ascertain the layers that have formed. If the cell is totipotent or pluripotent, the resulting teratoma will contain tissues from each of the three germ layers. In another example the PSCs are cultured in defined conditions in vitro to differentiate into specific cell types.

The primate totipotent and pluripotent stem cells disclosed herein are distinguished from other primate totipotent and pluripotent stem cells described previously in that they are generated by transferring nuclear genetic material from the somatic cells of one individual (such as a patient) in to recipient cells, such as an oocyte, from another individual, i.e., the stem cells derive their nuclear genetic material from the subject of interest, while the enucleated recipient (or host) cell is from a different donor which provides mitochondrial DNA. For example, the TSCs, PSCs and MPSCs generated using the methods disclosed herein will have essentially identical nuclear genetic material to the subject who is the source of the donor nuclear genetic material, and as such autologous transplantation of differentiated cells derived from the stem cells should not induce immune rejection when transplanted back into the donor. The TSCs and PSCs disclosed herein do not include primate stem cells that have been generated using solely sperm-fertilized oocytes, and thus have an equal contribution from two separate individuals (parents). Methods of determining whether a stem cell has derived its nuclear genetic material from one individual are readily known to one of skill in the art, including, but not limited to, microsatellite analysis. The primate totipotent or pluripotent (or multipotent) stem cells disclosed herein have mitochondrial DNA from one individual and the nuclear DNA from a second, different individual. In one embodiment, the cells do not include mitochondrial DNA from the first individual of interest. Thus, in one example, the mitochondrial DNA and the nuclear DNA of the primate totipotent or pluripotent stem cells (or multipotent stem cells) are from different individuals of the same species.

Disclosed herein is a purified preparation of primate PSCs which (a) is capable of being cultured for more than about one month in vitro; (b) maintains a normal karyotype; and (c) is capable of differentiating into germ cells, ectoderm, mesoderm, and endoderm layers; wherein said totipotent or pluripotent stem cells are derived from an enucleated cell from a first donor and the nuclear genetic material from a second donor. The purified preparation of primate PSCs can possess one or more (including all) of the following characteristics: (a) is capable of being cultured for more than 4 months in vitro; (b) maintains a normal karyotype; (c) is capable of differentiating into germ cells, ectoderm, mesoderm, and endoderm layers; and (d) derives its nuclear genetic material from a single individual. In one embodiment, the PSCs are human cells. In another embodiment the PSCs are non-human primate cells.

Compositions are disclosed that comprise one or more isolated pluripotent primate stem cells which possess one or more (including all) of the following characteristics: (a) are capable of being cultured for more than 1, 2, 3, 4, 5, or 6 months in vitro; (b) maintain a normal karyotype while in culture; (c) are capable of differentiating into the germ cell lineage, ectoderm, mesoderm, and endoderm layers; and (d) derive its nuclear genetic material from one individual. In one aspect, the pluripotent stem cells inherit mitochondrial DNA from an enucleated cell from a first donor and the nuclear genetic material from a second donor. In one embodiment, the PSCs are human cells. In another embodiment the PSCs are non-human primate cells.

Multipotent stem cells produced from these primate totipotent and pluripotent stem cells and stem cell lines are disclosed herein. These multipotent cells are not pluripotent or totipotent, and give rise to cells of a specific lineage. In several embodiments, the multipotent stem cells are capable of proliferating at least 5, 6, 7, 8 or more cell divisions and retaining multipotency. In additional embodiments, the multipotent stem cells are capable of being cultured for more than about 1, 2, 3, 4, 5, or 6 months in vitro. The disclosure also encompasses compositions, including, but not limited to, pharmaceutical compositions, comprising isolated multipotent cells which have been derived from one or more pluripotent primate stem cell which possess one or more (including all) of the following characteristics: (a) are capable of being cultured for more than 1, 2, 3, 4, 5, or 6 months in vitro; (b) maintains a normal karyotype while in culture; (c) are capable of differentiating into the germ cells, ectoderm, mesoderm, and endoderm layers; and (d) derive their nuclear genetic material from one individual and their mitochondrial DNA from a second individual. In one aspect, pluripotent stem cells are derived from an enucleated cell from a first recipient and the nuclear genetic material from a second donor, and multipotent stem cells are generated from these pluripotent cells. In one embodiment, the MPSCs are human cells. In another embodiment the MPSCs are non-human primate cells. Thus, the cells are MPSCs and are not TSCs or PSCs.

Also provided herein are pluripotent primate stem cell lines which possess one or more (including all) of the following characteristics: (a) are capable of 4 or more cell divisions in vitro; (b) maintain a normal karyotype while in culture; (c) are capable of differentiating into germ cells, ectoderm, mesoderm, and endoderm layers; and (d) derive its nuclear genetic material from one individual. Further provided herein are pluripotent primate stem cell lines which (a) are capable of 4 or more cell divisions in vitro; (b) maintain a normal karyotype while in culture; (c) are capable of differentiating into ectoderm, mesoderm, and endoderm layers; and (d) are derived from an enucleated host cell from a first donor and the nuclear material from a second donor.

Purified preparations of primate totipotent, pluripotent stem cells and multipotent cells are provided herein which have been generated using SCNT. The successful generation of such cells generally requires nuclear remodeling of the donor nucleus. The methods disclosed herein enable one of skill in the art to achieve success in nuclear remodeling. Generally, nuclear remodeling occurs within hours after transfer of the nucleus to the enucleated host cell (to the cytoplast). In one embodiment, the remodeling occurs within about 15 minutes after nuclear transfer. In another embodiment, the remodeling occurs within about 30 minutes after nuclear transfer. In another embodiment, the remodeling occurs within about 45 minutes after nuclear transfer. In another embodiment, the remodeling occurs within about 1 hour after nuclear transfer. In another embodiment, the remodeling occurs within about 2 hours after nuclear transfer. In other embodiments, the remodeling occurs within about 3, 4, or 5 hours after nuclear transfer. In other embodiments, the remodeling occurs within about 5, 6, or 7 hours after nuclear transfer. Thus, the remodeling can occur within 15 minutes to about 7 hours, such as within 30 minutes to about 6 hours, such as within 45 minutes to about 5 hours, such as within 1 to 4 hours of nuclear transfer. The indication that a cell is undergoing nuclear remodeling is generally known to one of skill in the art and involves events such as premature chromatin condensation and nuclear envelope breakdown. As the inventors have detailed in the Examples, monitoring of lamin A/C levels can also be used to assess the success of nuclear remodeling.

SCNT provides a means to produce isogenic cells of any cell type from a donor. Thus, provided are a preparation that comprises one or more TSCs, PSCs, or transplantable, cells that genetically match to the nuclear donor cell. By genetically match, it is understood that a 100% genetic match is not required but that that there is at least about 99.5% match. In some embodiments, the genetic match is at least about 99%, at least about 98%, at least about 97%, at least about 96%, at least about 95%, and at least about 94%. In other cases, the genetic match will be at least about 90% match. In one embodiment, the genetic match is at one major histocompatibility (MHC) locus. In other embodiments, the genetic match is at one or more MHC loci. In yet other embodiments, the genetic match is at 2, 3, 4, 5, 6 or more MHC loci. In a further embodiment, the genetic match is also at the minor histocompatibility loci.

Cell lines can also be derived from MPSCs or other transplantable cells derived from PSCs. Also provided herein are preparations of transplantable cells derived from TSCs and PSCs. These cells include, but are not limited to, neurons, cardiomyocytes, hematopoietic cells, keratinocytes, islet cells, mature gametes (sperm or oocytes) or any other cell type, including any cell type of an organism. In some embodiments, the purified preparation of transplantable cells is incorporated into a pharmaceutical composition or used in a method of treatment. The pharmaceutical composition can have additives, carriers, media components or other components in addition to the primate transplantable cells.

These cell lines encompass cells which have been frozen and thawed for subsequent culturing. Kits are also provided herein that include aliquots of cells (frozen or otherwise) with the desired properties, wherein the cells are produced by the methods disclosed herein.

Thus, compositions of non-human primate TSCs, PSCs, MPSCs or transplantable cells and cell lines derived therefrom are provided herein. In other aspects, compositions of human TSCs, PSCs, MPSCs or transplantable cells and cell lines derived therefrom are provided herein. Compositions of primate TSCs, PSCs, MPSCs or transplantable cells and cell lines derived therefrom that are obtained by using the methods disclosed herein are also provided.

Methods

Methods are provided for obtaining and culturing primate totipotent or pluripotent stem cells. In one embodiment, the TPSCs and/or PSCs are human cells. In another embodiment the TPSCs and/or PSCs are non-human primate cells.

The methods require the successful accomplishment of the following: (a) effecting complete or essentially complete removal of the nuclear genetic material from a recipient cell which can be an oocyte to provide an enucleated host cytoplast; (b) introduction of a nucleus from a somatic cell from the donor into the enucleated host cell cytoplast to form a renucleated cell; and (c) that both (a) and (b) be carried out under conditions such that, upon nuclear remodeling of the introduced somatic cell nucleus in the cytoplasm of the host cell and the induction of activation, the resulting TSCs exhibits the properties of a sperm-fertilized embryo such that subsequent mitotic cell division leads to the development of a blastocyst from which PSCs can be derived under culture conditions which typically sustain cultures of conventional embryonic stem cell (ESC) lines derived from sperm-fertilized embryos, ultimately resulting in viable cultures of pluripotent stem cells. Generally the donor and the recipient are from different individuals.

Any suitable cell can serve as a source for the enucleated host cell cytoplast provided that it permits sufficient nuclear reprogramming of the donor somatic cell nucleus. Non-limiting examples of such host cells include an unfertilized oocyte, a fertilized oocyte, a blastomere, a pluripotent ESC cytoplast, or a germ cell. In one embodiment, the cell is an oocyte. In one example, the oocyte is a human oocyte. In another embodiment, the oocyte is a non-human oocyte. In a further embodiment, the recipient cells is not from an embryo.

If oocytes are used as the donor cell to be enucleated, then one important aspect of methodology is to use high quality oocytes. High quality oocytes can be obtained by using protocols that stimulate the animal (e.g., primates) to produce a number of viable oocytes. Examples of such stimulation protocols are disclosed in the Examples and also in Zelinski-Wooten, et al. *Hum. Reprod.* 10:1658-1666 (1995). Another aspect that is important for ultimate success in getting totipotent or pluripotent stem cells is the method of harvesting. In one example, the oocytes can be harvested using methods known in the art, such as follicular aspiration, and then separated from contaminating blood cells. As an alternative, oocytes can be generated from PSCs in vitro.

In one aspect, when primates are stimulated to produce oocytes (such as hormonally) and these oocytes are harvested, the oocytes that are collected can be in different phases. Some oocytes are in metaphase I while other oocytes are in metaphase II. In such cases, the oocytes that are in metaphase I can be put into culture until they reach metaphase II and then used for enucleation to serve as the host cell. Optionally, the oocytes that have been cultured to reach metaphase II are combined with the oocytes that were already at metaphase II when harvested for a pool of potential host cells. In other cases, only the oocytes that are in metaphase II from the harvest are used for enucleation. Any of these oocytes can be frozen for further use.

In some embodiments, the enucleation of the host cell is accomplished using a technique that avoids an inhibition or down-regulation of maturation promoting factor (MPF) or its activity. The enucleation of the host cell refers to meiotic spindle removal. Maturation promoting factor or MPF is a heterodimeric protein comprising cyclin B and cyclin-dependent kinase 1 (i.e., p34cdc2) that stimulates the mitotic and meiotic cell cycles. Without being bound by theory, MPF promotes the entrance into mitosis from the G2 phase by phosphorylating multiple proteins needed during mitosis.

The technique employed to enucleate the cell can be any imaging system that avoids reducing the MPF levels or activity. MPF activity or levels can be determined by looking for biological effects that indicate activation has occurred. This would include chromatin condensation and nuclear envelope breakdown. It is further contemplated that the SCNT techniques useful in the method provided herein include not only those that directly impact MPF levels or activity, but also those that indirectly MPF levels or activity.

In some embodiments, removal of nuclear genetic material (i.e., enucleation) is accomplished without lowering the levels of maturation promoting factor (MPF) or its activity. In one embodiment, this means that the enucleation is accomplished without the use of UV-based methods, such as Hoechst 33342 staining and subsequent UV visualization. One method that can be used in lieu of Hoechst 33342 is real time spindle imaging. In one embodiment, the enucleation technique employs the real time spindle imaging system such as OOSIGHT™ Imaging System (CRI, Inc. Woburn, Mass.). This system utilizes a wavelength of 545 nm and has diffraction limited spatial resolution. The relay optics are 0.65×. Generally the system includes a circular polarized interference filter with tunable liquid crystal polarizing filters. In one example, any system is of use that utilizes a liquid crystal tunable fiberoptic, a circular polarizer/green interference fiber optic, and can include a CCD camera with software for image acquisition and analysis. Generally, the system can merge polarized light imaging with single point analysis by quantifying magnitude and orientation of birefringence at each pixel in a field, at or near to real time. The spindle and the zona pellucida of an oocyte display an intrinsic property termed "birefringence" when trans-illuminated with polarized light, a property that can be used for efficient visuzalization and thus enucleation. The use of such a real time system permits non-invasive visualization and the complete, or essentially complete, removal of nuclear material from the host cell (e.g., oocyte). In one example, the entire mitotic spindle and its associated DNA from the host cell is removed such that any potential for generating parthenotes is reduced or eliminated altogether.

In addition, exposure to caffeine, a protein phosphatase inhibitor (Kawahara et al., Reproduction 130(3): 351-7, 2005; Lee and Campbell, Biol Reprod 74(4): 691-8, 2006) or the proteasome inhibitor, MG-132 (Zhou et al., Science 302 (5648): 1179, 2003) increases the activity of MPF. MG-132 can be utilized in the methods disclosed herein at concentrations, for example, of about 0.1 to 10 μM, such as about 0.5 to about 10 μM, such as about 0.5 to about 5 μM, such as about 1 to about 3 μM, such as about 1 to about 2 μM. In some examples, 0.2, 2 or 5 μM MG-132 can be utilized. Caffeine can be used, for example at concentrations of about 0.25 mM to about 25 mM, such as about 1 mM to 10 mM, such as 1 mM to 3 mM, such as about 2.5 mM.

Any suitable somatic cell may be used as the source of the donor nucleus. It will be appreciated by those skilled in the art that the selection of the somatic cell type from the donor to be the source of the nucleus for SCNT is not critical and can be selected from cells that can be removed in appropriate quantities from the donor without significant discomfort or risk. Exemplary somatic cells include, but are not limited to keratinocytes, white blood cells, skin cells, and adipose cells. In one embodiment, electrofusion is used to introduce the somatic cell nucleus. In anther embodiment, direct injection is used to introduce the somatic cell nucleus.

In one embodiment, the donor somatic cell nucleus can include modified nucleic acids, such as nucleic acid (e.g., DNA) that includes a recombinant product. In one non-limiting example, the donor nucleus is obtained from a transgenic animal or an animal with an engineered knock-out mutation. In a further example, the donor nucleic acid includes heterologous DNA that encodes a protein product, such as a detectable marker, enzyme, or other protein. The donor nucleic acid can also include other nucleic acids, such as ribozymes or antisense nucleic acid sequences. The heterologous nucleic acid can also be a regulatory sequence, such as a promoter, enhancer, insulator or repressor. Techniques for modifying nucleic acids are well known in the art, and include inserting a DNA that is synthetic or from another organism into the donor nucleic acid, deleting one or more DNA sequences from the donor, and introducing mutations, such as point mutations into the donor nucleic acid. Methods and tools for manipulation of nucleic acids are well known in the art, see for example *Molecular Cloning: A Laboratory Manual*, second edition (Sambrook et al., 1989) Cold Spring Harbor Press; *Oligonucleotide Synthesis* (M. J. Gait, ed., 1984); *Animal Cell Culture* (R. I. Freshney), ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) *Short Protocols in Molecular Biology* (Wiley and Sons, 1999), *Embryonic Stem Cells: A Practical Approach* (Notaranni et al. eds., Oxford University Press 2006); and *Essential of Stem Cell Biology* (R. Lanza, ed., Elsevier Academic Press 2006).

In another embodiment, for either the enucleation step or the nuclear transfer step or both, the use of any suitable reagent that minimizes calcium fluxes in the donor cell immediately following nuclear transfer can be employed. Without being bound by theory, the reduction of calcium fluxes following nuclear transfer provides for more successful nuclear reprogramming. In one aspect, the avoidance of calcium fluxes or oscillation in the host cell allows for the MPF levels to be kept high and thus allow for more successful nuclear remodeling to occur.

In several examples, enucleation and/or nuclear transfer is performed in calcium ($Ca^{2+}$)-free media. In additional examples, enucleation is performed in magnesium ($Mg^{2+}$)-free media and calcium-free ions. For example, calcium-free phosphate buffered saline can be utilized. This media is substantially free of calcium ions. In one embodiment, a calcium-free medium contains less than about $10^{-6}$ M calcium cations ($Ca^{2+}$), such a media that contains less that as $10^{-7}$ M calcium cations, $10^{-8}$ M calcium cations, $10^{-9}$ M calcium cations, or is substantially free of calcium cations. Similarly, a magnesium-free medium contains less than about $10^{-6}$ M magnesium cations ($Mg^{2+}$), such a media that contains less that as $10^{-7}$ M magnesium cations, $10^{-8}$ M magnesium cations, $10^{-9}$ M magnesium cations, or is substantially free of magnesium cations. The selection of the appropriate media or other reagents that will, for example, chelate extracellular calcium and/or magnesium, such as ethylene glycol tetraacetic acid (EGTA) or ethylene diamine tetraacetic acid (EDTA), do not have added calcium and/or magnesium ions, or otherwise reduce the calcium fluxes during these manipulations are known in the art. Exemplary media are described in the examples section. These media and reagents are commercially available, and suitable media can be routinely produced in the laboratory.

The amount of time required after introduction of the donor nucleus to the recipient cell for a premature condensed chromosome and spindle to form may vary from cell type to cell type and/or from species to species. In order to allow sufficient time for the premature condensed chromosome and spindle to form, the cell may require culturing for from about 0.5 hours to about 10 hours, from about 1 hour to about 8 hours, from about 1.25 hours to about 6 hours, from about 1.5 hours to about 4 hours, from about 1.75 hours to about 3 hours, or about 2 hours after introduction of the donor nucleus to the recipient or host cell.

Following spindle formation, the cell can be contacted with a chemical activator, such as ionomycin or ethanol. In one example, ionomycin is used as the chemical activator. Concentrations of ionomycin for activation may be from about 0.5 µM to about 50 mM, from about 1 mM to about 40 mM, from about 1.5 mM to about 30 mM, from about 2 µM to about 20 mM, from about 2.5 mM to about 10 mM, from about 3 mM to about 9 µM, from about 3.5 mM to about 8 mM, from about 4 mM to about 7 mM, from about 4.5 µM to about 6 mM, or about 5 mM.

The amount of time that cells are exposed to the chemical activator can also be modified to provide additional control over the activation process. The cells can be exposed to the chemical activator, such as ionomycin for between about 1 minute and about 30 minutes, between about 1.5 minutes and about 20 minutes, between about 2 minutes and about 15 minutes, between about 2.5 minutes and about 12 minutes, between about 3 minutes and about 10 minutes, between about 3.5 minutes and about 9 minutes, between about 4 minutes and about 8 minutes, between about 4 minutes and about 7 minutes, between about 4 minutes and about 6 minutes, or for about 5 minutes.

Accordingly, methods are provided for producing a pluripotent primate stem cell comprising the steps of: (a) enucleating a primate oocyte by using a non-UV-based spindle imaging system such that a sufficient amount of the nucleus is removed such that parthenogenesis cannot occur; and (b) introducing the nucleus of a primate somatic cell into the enucleated cell, wherein the enucleation and insertion steps occur in media free of $Ca^{++}$ ions; wherein the resulting cell (i) is capable of being cultured for more than 1 month in vitro; (ii) maintains a normal karyotype while in culture; (iii) is capable of differentiating into ectoderm, mesoderm, and endoderm layers.

As detailed in the Examples, a synergistic effect was seen in the efficiency of nuclear reprogramming (i.e., successful creation of totipotent and subsequently pluripotent cells following SCNT) when using the combination of a non-UV-based enucleation techniques and introduction of donor nucleus using $C^{2+}$-free media. Thus in some embodiments, the efficiency of producing stem cells using the methods disclosed herein is at least about 10%, at least about 13%, at least about 15%, at least about 20%, at least about 25%, at least about 30% or greater. In contrast, the efficiency of either technique alone was about 1%.

Following introduction of the donor somatic cell nucleus into the enucleated recipient cell the cell is cultured in vitro. Methods of culturing primate totipotent or pluripotent stem cells are well-known in the art. Any cell culture media that can support the growth and differentiation of human embryonic stem cells can be used. In some embodiments, the pluripotent stem cells are cultured on a feeder layer, such as of murine or primate embryonic fibroblasts. However, the feeder layer can be any cells that support the growth of ESCs. This approach makes for a completely autologous culturing system, thereby eliminating the risk of cross-species contamination. For therapeutic use, the culturing methods can be xeno-free (no xenogeneic cells or components) and additionally avoid the use of serum (such as fetal bovine serum, FBS) in the culturing media.

In some embodiments, the methods encompass non-human primate totipotent or pluripotent cells made by the methods described herein. In other embodiments, the methods include the use of human totipotent or pluripotent cells made by the methods described herein.

TSC or PSC cells can be produced from human and non-human primates. In one embodiment, primate TSC or PSC cells are isolated and subsequently cultured in "ES medium," which supports the growth of embryonic stem cells. The PSCs express SSEA-3, SSEA-4, TRA-1-60, and TRA-1-81. For example, ES medium comprises 80% Dulbecco's modified Eagle's medium (DMEM; no pyruvate, high glucose formulation, Gibco BRL), with 20% fetal bovine serum (FBS; Hyclone), 0.1 mM B-mercaptoethanol (Sigma), 1% non-essential amino acid stock (Gibco BRL).

In one example, an oocyte is enucleated using the methods disclosed above, and a somatic cell nucleus is inserted into the enucleated oocyte, as described herein. The resultant cell is then cultured in medium, such as but not limited to protein-free HECM-9 medium and cultured at 37° C. in about 5-6% $CO_2$ until use. These cultures can be maintained under paraffin oil. Once the TSCs reaches about the 2 cell stage or beyond, such as the 4, 8 or 16 cell stage, the cells can be transferred for further culture. In one embodiment, these TSCs are cultured to the blastocyst stage in a culture medium, such as, but not limited to, HECM-9 medium.

In some embodiments, the zonae pellucidae of selected expanded blastocysts are be removed by brief exposure (45-60 seconds) to 0.5% pronase in TH3 medium. In some embodiments an ICM can be isolated from tropectoderm cells by immunosurgery, where zona-free blastocysts are exposed to rabbit anti-rhesus spleen serum for about 30 minutes at abut 37° C. After extensive washing (such as using TH3 medium), embryos are incubated in guinea pig complement reconstituted with HECM-9 (1:2, v/v) for about an additional 30 minutes at about 37°. Partially lysed trophectodermal cells are mechanically dispersed by gentle pipetting, such as with a small bore pipette (for example, about a 125 µm in inner diameter; Stripper pipette, Midatlantic Diagnostics Inc., Marlton, N.J.) followed by the rinsing of ICMs three times, such as with TH3 medium. Isolated ICMs are plated onto a solid substrate, such as onto Nunc 4-well dishes containing mitotically-inactivated feeder layers consisting of mouse embryonic fibroblasts (mEFs) and cultured, such as in DMEM/F12 medium (Invitrogen) with glucose and without sodium pyruvate supplemented with 1% nonessential amino acids (Invitrogen), 2 mM L-glutamine (Invitrogen), 0.1 mM β-mercaptoethanol and 15% FBS and maintained at about 37° C., about 3% $CO_2$, about 5% $O_2$ and about 92% $N_2$ gas conditions. Alternatively, whole, intact blastocysts can be directly plated onto mEFs for ESC isolation.

After about 1 to about 7 days, cells, such as blastocysts or ICMs that attached to the feeder layer and initiated outgrowth can be dissociated into small cell clumps, such as manual dissociation with a microscalpel, and re-plated onto a new substrate, such as new embryonic fibroblasts (mEFs). After the first passage, colonies with embryonic stem cell (ESC)-like morphology are selected for further propagation, characterization and low temperature storage. Generally, ESC morphology is compact colonies having a high nucleus to cytoplasm ratio, prominent nucleoli, sharp adages and flat colonies. In some examples, the medium is changed daily and ESC colonies are split about every 5-7 days manually or by disaggregation in collagenase IV, (for example, about 1 mg/ml, at about 37° C. for about 2-3 minutes; Invitrogen) and replating collected cells onto dishes with fresh feeder layers. Cultures are maintained at about 37° C., about 3% $CO_2$, about 5% $O_2$ and about 92% N2. In another alternative, serum-free media is used.

PSCs can then be isolated, and PSCs can be maintained in vitro using standard procedures. In one embodiment, primate PSCs are isolated on a confluent layer of fibroblast in the presence of ESC medium. In one example, to produce a feeder layer, xenogeneic embryonic fibroblasts are obtained from 14-16 day old fetuses from outbred mice (such as CF1, available from SASCO), but other strains may be used as an alternative. Alternatively, human fibroblasts obtained from adult skin or cells obtained from TSC-derived fibroblasts can be employed. In another embodiment, tissue culture dishes treated with about 0.1% gelatin (type I; Sigma) can be utilized. Unlike mouse PSC cells, human PSC (hPSC) cells do not express the stage-specific embryonic antigen SSEA-1, but express SSEA-4, which is another glycolipid cell surface antigen recognized by a specific monoclonal antibody (see, for example, Amit et al., *Devel. Biol.* 227:271-278, 2000).

ICM-dissociated cells can be plated on feeder layers in fresh medium, and observed for colony formation. Colonies demonstrating ESC morphology are individually selected, and split again as described above. Resulting PSCs are then routinely split by mechanical methods every six days as the cultures become dense. Early passage cells are also frozen and stored in liquid nitrogen.

PSCs as well as transplantable cells can be produced and can be karyotyped with, for example, a standard G-banding technique (such as by the Cytogenetics Laboratory of the University of Wisconsin State Hygiene Laboratory, which provides routine karyotyping services) and compared to published karyotypes for the primate species.

In other embodiments, immunosurgical isolation of the ICM is not utilized. Thus, the blastocysts are cultured directly, without the use of any immunosurgical techniques. Isolation of primate PSCs from blastocysts, including humans, would follow a similar procedure, except that the rate of development of TSCs to blastocyst can vary by a few days between species, and the rate of development of the cultured ICMs will vary between species. For example, six days after fertilization, rhesus monkey zygotes are at the expanded blastocyst stage, whereas marmoset embryos do not reach the same stage until 7-8 days after fertilization. Because other primates also vary in their developmental rate, the timing of the initial ICM split varies between primate species, but the same techniques and culture conditions will allow ESC isolation (see U.S. Pat. No. 6,200,806, which is incorporated herein by reference for a complete discussion of primate ESCs and their production). Culture conditions described above can also be used for the culture of PSCs from blastocysts. Conditions for culturing human TSCs obtained by conventional protocols from fertilized oocyte to the blastocyst have been described (see Bongso et al., *Hum Reprod.* 4:706-713, 1989). In some embodiments, co-culturing of human TSCs with human oviductal cells results in the production of high quality blastocyst. Human ICM from blastocysts grown in cellular co-culture, or in media that eliminates the feeder cell layer requirement, allows isolation of human PSCs with the same procedures described above for non-human primates.

Uses for Primate Pluripotent Stem Cells

Also provided herein are therapeutic compositions comprised of transplantable cells which have been derived (produced) from PSCs in a formulation suitable for administration to a primate. In one embodiment, the donor primate that is the source of the somatic nucleus. In a preferred embodiment, the primate is human. The therapeutic compositions include multipotent cells, lineage-specific stem cells, as well as partly or fully differentiated cells derived from the PSCs provided herein.

The preparations of cells derived from primate PSCs allows for methods for providing cells to an individual in need thereof by administering an effective amount of one or more preparations of transplantable cells to the individual in need thereof. The cells will be matched at one or more loci of the major histocompatibility complex (MHC). In one embodiment, there is a complete match at every MHC loci. In one embodiment the TSC is made by the transfer of a nucleus from a somatic cell of the individual of interest into an enucleated host cell (e.g., oocyte) from a second individual. The TSC can then be cultured as described above to produce PSCS and multipotent stem cells (MPSCs). A therapeutically effective amount of the multipotent cells can then be utilized in the subject of interest. In one embodiment, cells matched at one or more MHC loci to the treated individual are generated and cultured using the teachings provided herein, such as by SCNT. In a preferred embodiment, the cells are cultured in media free of serum. In another preferred embodiment, the cells have not been cultured with xenogeneic cells (e.g., non-human fibroblasts such as mouse embryonic fibroblasts).

Methods for treating disease are provided that comprise transplanting cells derived from PSCs in a primate afflicted with a disease characterized by damaged or degenerative somatic cells. Such cells can be multipotent cells or any other type of transplantable cells.

The primate PSCs described herein are useful for the generation of cells of desired cell types. In some embodiments, the PSCs are used to derive mesenchymal, neural, and/or hematopoietic stem cells. In other embodiments, the PSCs are used to generate cells, including but not limited to, pancreatic, liver, bone, epithelial, endothelial, tendons, cartilage, and muscle cells, and their progenitor cells. Thus, transplantable cells derived from PSCs can be administered to an individual in need of one or more cell types to treat a disease, disorder, or condition. Examples of diseases, disorders, or conditions that may be treated or prevented include neurological, endocrine, structural, skeletal, vascular, urinary, digestive, integumentary, blood, immune, auto-immune, inflammatory, kidney, bladder, cardiovascular, cancer, circulatory, hematopoietic, metabolic, reproductive and muscular diseases, disorders and conditions. In some embodiments, a hematopoietic stem cell derived from primate PSCs is used to treat cancer. In some embodiments, these cells are used for reconstructive applications, such as for repairing or replacing tissues or organs.

The TSCs and PSCs described herein can be used to generate multipotent stem cells or transplantable cells. In one example, the transplantable cells are mesenchymal stem cells. Mesenchymal stem cells give rise to a very large number of distinct tissues (Caplan, *J. Orth. Res* 641-650, 1991). Mesenchymal stem cells capable of differentiating into bone, muscles, tendons, adipose tissue, stromal cells and cartilage have also been isolated from marrow (Caplan, *J. Orth. Res.* 641-650, 1991). U.S. Pat. No. 5,226,914 describes an exemplary method for isolating mesenchymal stem cells from bone marrow. In other examples, epithelial progenitor cells or keratinocytes can be generated for use in treating conditions of the skin and the lining of the gut (Rheinwald, *Meth. Cell Bio.* 21A:229, 1980). The cells can also be used to produce liver precursor cells (see PCT Publication No. WO 94/08598) or kidney precursor cells (see Karp et al., *Dev. Biol.* 91:5286-5290, 1994). The cells can also be used to produce inner ear precursor cells (see Li et al., *TRENDS Mol. Med.* 10: 309, 2004).

The transplantable cells can also be neuronal cells. The volume of a cell suspension, such as a neuronal cell suspension, administered to a subject will vary depending on the site of implantation, treatment goal and amount of cells in solution. Typically the amount of cells administered to a subject will be a therapeutically effective amount. For example, where the treatment is for Parkinson's disease, transplantation of a therapeutically effective amount of cells will typically produce a reduction in the amount and/or severity of the symptoms associated with that disorder, e.g., rigidity, akinesia and gait disorder. In one example, a severe Parkinson's patient needs at least about 100,000 surviving dopamine cells per grafted site to have a substantial beneficial effect from the transplantation. As cell survival is low in brain tissue transplantation in general (5-10%) at least 1 million cells are administered, such as from about 1 million to about 4 million dopaminergic neurons are transplanted. In one embodiment, the cells are administered to the subject's brain. The cells can be implanted within the parenchyma of the brain, in the space containing cerebrospinal fluids, such as the sub-arachnoid space or ventricles, or extraneurally. Thus, in one example, the cells are transplanted to regions of the subject which are not within the central nervous system or peripheral nervous system, such as the celiac ganglion or sciatic nerve. In another embodiment, the cells are transplanted into the central nervous system, which includes all structures within the dura mater. Injections of neuronal cells can generally be made with a sterilized syringe having an 18-21 gauge needle. Although the exact size needle will depend on the species being treated, the needle should not be bigger than 1 mm diameter in any species. Those of skill in the art are familiar with techniques for administering cells to the brain of a subject.

Generally a therapeutically effective amount of cells is administered to an individual. The cells can be administered in a pharmaceutical carrier. The pharmaceutically acceptable carriers of use are conventional. For example, *Remington's Pharmaceutical Sciences*, by E. W. Martin, Mack Publishing Co., Easton, Pa., 15th Edition (1975), describes compositions and formulations suitable for pharmaceutical delivery of the cells herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The individual can be any subject of interest. Suitable subjects include those subjects that would benefit from proliferation of cells derived from stem cells or precursor cells. In one embodiment, the individual is in need of proliferation of neuronal precursor cells and/or glial precursor cells. For example, the individual can have a neurodegenerative disorder or have had an ischemic event, such as a stroke. Specific, non-limiting examples of a neurodegenerative disorder are Alzheimer's disease, Pantothenate kinase associated neurodegeneration, Parkinson's disease, Huntington's disease (Dexter et al., *Brain* 114:1953-1975, 1991), HIV encephalopathy (Miszkziel et al., *Magnetic Res. Imag.* 15:1113-1119, 1997), and amyotrophic lateral sclerosis. Suitable individual also include those subjects that are aged, such as individuals who are at least about 65, at least about 70, at least about 75, at least about 80 or at least about 85 years of age. In additional examples, the individual can have a spinal cord injury, Batten's disease or spina bifida. In further examples, the individual can have hearing loss, such as a subject who is deaf, or can be in need of the proliferation of stem cells from the inner ear to prevent hearing loss.

Primate PSCs produced using the methods disclosed herein are capable of contributing to the germ line. Thus, somatic cells from a subject of interest can be used to produce ES cells which subsequently can be differentiated into oocytes or sperm. These oocytes or sperm can then be used for fertilization, allowing an infertile subject to produce children that are genetically related to the subject. In addition, ES cell-derived eggs are of use in research. For example, these egges can in turn be used to make SCNT-derived ES cells. This availability of these oocytes can reduce the use of donated human eggs for research.

TSCs can also be used to generate extra embryonic cells, such as trophectoderm, that are of use in cell culture. In one embodiment, the use of autologous cells (e.g., trophectoderm) as feeder cells can be helpful to generate stem cells that in turn have the capacity to differentiate into differentiated organ-specific cells. In other embodiments, the use of allogeneic feeder cells, obtained by using culturing totipotent stem cells in such a manner to allow the generation of such feeder layer component, is useful to avoid xeno-contamination and thus, allow for easier FDA approval of the differentiated cells cultured thereupon for therapeutic purposes.

Cells produced by the methods disclosed herein, such as TSC and PSC are also of use for testing agents of interest, such as to determine if an agent affects differentiation or cell proliferation. For example, TSCs or PSCs are contacted with the agent, and the ability of the cells to differentiate or proliferate is assessed in the presence and the absence of the agent. Thus, cells produced by the methods disclosed herein can also be used in to screen pharmaceutical agents to select for agents that affect specific human cell types, such as agents that affect neuronal cells. Cell produced by the methods disclosed herein can also be used to screen agent to select those that affect differentiation. The test compound can be any compound of interest, including chemical compounds, small molecules, polypeptides or other biological agents (for example antibodies or cytokines). In several examples, a panel of potential agents are screened, such as a panel of cytokines or growth factors is screened.

Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991), a peptide library (U.S. Pat. No. 5,264,563); a peptidomimetic library (Blondelle et al., *Trends Anal Chem.* 14:83-92, 1995); a nucleic acid library (O'Connell et al., *Proc. Natl Acad. Sci.*, USA 93:5883-5887, 1996; Tuerk and Gold, Science 249:505-510, 1990; Gold et al., *Ann. Rev. Biochem.* 64:763-797, 1995); an oligosaccharide library (York et al., *Carb. Res.* 285:99-128, 1996; Liang et al., *Science* 274:1520-1522, 1996; Ding et al., *Adv. Expt. Med. Biol.* 376:261-269, 1995); a lipoprotein library (de Kruif et al., *FEBS Lett.* 3 99:23 2-23 6, 1996); a glycoprotein or glycolipid library (Karaoglu et al., *J. Cell Biol.* 130.567-577, 1995); or a chemical library containing, for example, drugs or other pharmaceutical agents (Gordon et al., *J. Med. Chem.* 37.1385-1401, 1994; Ecker and Crooke, *BioTechnology* 13:351-360, 1995). Polynucleotides can be particularly useful as agents that can alter a function pluripotent or totipotent cells because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, TSCs, PSCs or MPSCs produced by the methods disclosed herein can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of the cells, for example, an agent that induces the cells to differentiate into a desired cell type, or that prevents spontaneous differentiation, for example, by maintaining a high level of expression of regulatory molecules.

The cells are contacted with test compounds sufficient for the compound to interact with the cell. When the compound binds a discrete receptor, the cells are contacted for a sufficient time for the agent to bind its receptor. In some embodiments, the cells are incubated with the test compound for an amount of time sufficient to affect phosphorylation of a substrate. In some embodiments, cells are treated in vitro with test compounds at 37° C. in a 5% $CO_2$ humidified atmosphere. Following treatment with test compounds, cells are washed with $Ca^{2+}$ and $Mg^{2+}$ free PBS and total protein is extracted as described (Haldar et al., *Cell Death Diff* 1:109-115, 1994; Haldar et al., *Nature* 342:195-198, 1989; Haldar et al., *Cancer Res.* 54:2095-2097, 1994). In additional embodiments, serial dilutions of test compound are used.

The following Examples are provided to illustrate various aspects of the invention; however the Examples are not to limit the scope of the invention in any manner.

EXAMPLES

Despite the remarkable progress achieved in the past decade in SCNT in mammals, success in primates has been long in coming. Disclosed herein is the production of rhesus monkeys by nuclear transfer using embryonic blastomeres as the source of donor nuclei (Meng et al., Biol Reprod 66(5): 1367-73, 1997; Mitalipov et al., Biol Reprod 66(5): 1367-73, 2002). Demonstrated herein is a high, similar to sperm-fertilized controls, in vitro blastocyst formation potential of NT embryos employing 8-16-cell stage blastomeres as nuclear donor cells. In contrast, the developmental potential of SCNT monkey embryos has been limited (Mitalipov et al., supra, 2002), seldom progressing beyond the 8-cell stage in vitro when fetal fibroblasts were employed as nuclear donor cells. Successful pregnancy initiation was reported following transfer of SCNT embryos in the cynomolgus monkey, however, spontaneous loss occurred within 60 days of gestation (Ng et al., Development 131(10): 2475-84, 2004). It was concluded that the failure of somatic but not embryonic cell nuclear transfer in the monkey was due to the incomplete reprogramming of the somatic cell nucleus (Mitalipov et al., supra, 2002). Studies demonstrating aberrant POU5F1 (Oct-4) expression in reconstructed embryos were consistent with this conclusion (Mitalipov et al., Biol Reprod 69(6): 1785-92 2003). A prospective study was reported comparing SCNT outcome in the monkey using a conventional protocol versus a one step method (OSM) used in the rat (Zhou et al., Science 302(5648): 1179, 2003; Zhou et al. Hum Reprod., 21(10) 2564-71, 2006). The OSM was clearly superior; however, the mechanisms responsible for the outcome were not investigated. It is disclosed herein that the ability of cytoplasts to induce donor nucleus remodeling was instrumental in efficient reprogramming and, hence, SCNT outcome (Mitalipov et al Hum Reprod. 2007 (8):2232-42). Each step in SCNT was analyzed, applying assessments of the individual cytoplast ability to induce nuclear remodeling measured by immunolabeling of lamin A/C. Modifications in nuclear transfer protocols that limited MPF degradation and premature cytoplast activation resulted in surprisingly enhanced nuclear remodeling and dramatic effects on SCNT development. The routine recovery of blastocysts from several somatic nuclear donor cells was accomplished providing the foundation for the production of SCNT monkeys and the derivation of embryonic stem cells (ESCs).

Derivation of embryonic stem cells (ESCs) genetically identical to a patient by somatic cell nuclear transfer (SCNT)

holds the potential to cure or alleviate the symptoms of many degenerative diseases while circumventing immunorejection concerns. However, the concept has only been achieved in the mouse while inefficient reprogramming and poor embryonic development characterizes the results obtained in primates. The modified SCNT approach was used to produce rhesus macaque SCNT blastocysts from adult skin fibroblasts and successfully isolated two ESC lines from these embryos. DNA analysis confirmed that nuclear DNA was identical to donor somatic cells and that mitochondrial DNA originated from oocytes. Both cell lines exhibited normal ESC morphology, expressed key stemness markers, were transcriptionally similar to control ESCs and differentiated into multiple cell types in vitro and in vivo. The results represent successful nuclear reprogramming of adult somatic cells into pluripotent ESCs and demonstrate proof-of-concept for therapeutic cloning in primates.

Example 1

Somatic Cell Nuclear Transfer Techniques, Ovarian stimulation, Recovery of Rhesus Macaque Oocytes, Fertilization by ICSI and Embryo Culture A schematic diagram of SCNT is presented in FIG. 1.

Controlled ovarian stimulation and oocyte retrieval for SCNT. Controlled ovarian stimulation and oocyte recovery has been described previously (Zelinski-Wooten, Hutchison et al. 1995) and is described in the Detailed Description. Briefly, cumulus-oocyte complexes were collected from anesthetized animals by laparoscopic follicular aspiration (28-29 hours post hCG) and placed in Hepes-buffered TALP (modified Tyrode solution with albumin, lactate and pyruvate) medium (Bavister and Yanagimachi 1977) containing 0.3% BSA (TH3) at 37° C. Oocytes, stripped of cumulus cells by mechanical pipetting after brief exposure (<1 min) to hyaluronidase (0.5 mg/ml), were placed in chemically defined, protein-free HECM-9 medium (Hamster Embryo Culture Medium) (McKiernan and Bavister 2000) at 37° C. in 6% $CO_2$, 5% $O_2$ and 89% N2 until further use.

Fertilization by ICSI and culture conditions for TSCs was performed as described previously (Wolf, Thormahlen et al. 2004). After ICSI, injected oocytes were placed in 4-well dishes (Nalge Nunc International Co., Naperville, Ill.) containing protein-free HECM-9 medium and cultured at 37° C. in 6% $CO_2$, 5% $O_2$ and 89% $N_2$. Cultures were maintained under paraffin oil. SCNT-derived TSCs at the 8-cell stage were transferred to fresh plates of HECM-9 medium supplemented with 5% fetal bovine serum (FBS; HyClone, Logan, Utah) and cultured to the blastocyst stage with the medium changed every other day.

Materials

1. Recombinant human follicular stimulating hormone (FSH), leutinizing horomone (LH) and chorionicgonadotropin (CG) (Ares Advanced Technologies Inc.; Norwell, Mass.) (or recombinant monkey gonadotropins when available)

2. Antide (GnRH antagonist, Ares Advanced Technologies Inc.)

3. Ketamine (Vedco, Inc., St. Joseph, Mo.)

4. TH3 medium: Hepes-buffered TALP medium, containing 0.3% BSA. The medium was prepared by adding the indicated amounts of each reagent (Sigma, St. Louis, Mo.) to 1 L of Milli-Q water.

| | |
|---|---|
| NaCl | 6.660 g |
| KCl | 0.239 g |
| $CaCL_2$—$2H_2O$ | 0.294 g |
| $MgCl_2$—$6H_2O$ | 0.102 g |
| $Na_2HPO_4$ | 0.048 g |
| Glucose | 0.900 g |
| Na Lactate | 1.87 ml |
| Phenol Red | 0.010 g |
| $NaHCO_3$ | 0.168 g |
| Gentamicin sulfate | 0.050 g |
| Hepes | 2.603 g |
| Na Pyruvate | 0.060 g |
| pH | 7.2-7.4 |
| Osmolarity | 282 ± 10 |

The medium was filtered using a 0.2, filter unit and stored for up to one month at +4° C. Then, BSA (Sigma) was added at 3 mg/ml prior to use and refiltered.

5. HECM-9 medium: HECM-9 base medium was prepared by adding the indicated amounts of each reagent (Sigma) to 1 L of Milli-Q water.

| | |
|---|---|
| PVA | 0.1 g |
| NaCl | 6.639 g |
| KCl | 0.224 g |
| $CaCl_2 \cdot 2H_2O$ | 0.279 g |
| $MgCl_2 \cdot 6H_2O$ | 0.102 |
| $NaHCO_3$ | 2.1 g |
| Lactic Acid, Na salt, 60% syrup | 632 μl |
| Gentamicin sulfate | 0.01 g |
| pH | 7.2-7.4 |
| Osmolarity | 277 ± 5 |

The medium was filtered using a 0.2, filter unit and stored for up to one week at +4° C.

6. 100× Amino Acid/Pantothenate stock: The stock was prepared by adding the indicated amounts of each reagent (Sigma) to 1 L of Milli-Q water.

| | |
|---|---|
| Taurine | 6.260 g |
| Asparagine | 0.130 g |
| Cysteine | 0.18 g |
| Histidine | 0.21 g |
| Lysine | 0.18 g |
| Proline | 0.12 g |
| Serine | 0.11 g |
| Aspartic Acid | 0.13 g |
| Glycine | 0.08 g |
| Glutamic Acid | 0.17 g |
| Glutamine | 2.92 g |
| Pantothenic Acid | 0.07 g |

This stock was filtered and distributed as 500 μl per 1.5 ml tubes and stored at −20° C. for up to 3 months.

7. HECM-9aa medium: AA/Pantothenate stock was added to HECM-9 base medium at a ratio of 1:100 prior to use. HECM-9aa was used to hold oocytes from the time of recovery until IVF, ICSI or NT, as well as to culture embryos until the 4-8-cell stage (or Day 2). For extended culture (to the blastocyst stage), embryos are transferred at the 4-8-cell stage (end of Day 2) to HECM-9aa medium supplemented with 5% FBS (HyClone, v/v). Embryos were transferred to fresh HECM-9aa+5% FBS every other day. Harvested oocytes were examined under the microscope and separated on MI and MII. MI oocytes were allowed to mature to the MII stage for additional 3-4 hours by culturing in HECM-9aa media.

Maturation was controlled by visual examination of cultures. Once the oocytes reached the MII stage, they were further used for micromanipulations.

8. Hyaluronidase (Sigma H-3506) stock: for 10× stock, 50 mg was reconstituted in 10 ml of Hepes-buffered TALP medium, separated into 0.5 ml aliquots and stored at −20° C.

9. Light paraffin oil (Zander IVF; Vero Beach, Fla.)

10. Cell strainers (70 μm Nylon; Falcon; BD Biosciences; Bedford, Mass.)

11. Portable incubator (Minitube; Madison, Miss.)

12. Ultrasonography equipment (OOWYCR, Philips)

13. Dissecting microscope (SZ-61, Olympus America, Inc.)

Methods

Protocols for COS in rhesus monkeys with recombinant human gonadotropins have been developed at the Oregon National Primate Research Center using the following steps:

1. Monitor cycling females for menstruation and 1-4 days following onset, administer twice daily i.m injections of 30 IU recombinant human FSH (at 8 AM and 4 PM) for 8 days.

2. Administer Antide at a dose of 0.5 mg/kg, s.c. once a day for 8 days to suppress pituitary function and prevent spontaneous LH surges.

3. On the last two days of stimulation (days 7 and 8), additionally administer twice daily injections of recombinant human LH (30 IU i.m.).

4. On day 8, anesthetize animals with ketamine (10 mg/kg body weight, i.m) and examine ovarian morphology by ultrasonography. Typically, a responsive ovary will be enlarged from 6 mm to an average diameter of 10 mm or greater and will contain at least 5 large follicles, 2-4 mm in diameter.

5. On the morning of day 9, inject monkeys meeting these criteria with recombinant hCG (1000 IU, i.m.) to induce oocyte maturation. Ovarian oocytes, which arrest at prophase I (GV), resume meiosis in response to hCG and arrest again at metaphase II (MII). Approximately 20% of gonadotropin-treated females are discontinued at this time due to lack of adequate response as judged by ultrasonography. The percentage of "non-responders" varies by season showing an increase during the summer months, reaching over 35% in June and July. During summer, despite housing in controlled, constant environments, many females also become anovulatory and it is impractical to attempt controlled ovarian stimulation (COS). Females can be recycled for COSs; however, the response to recombinant human gonadotropins is gradually decreased with increasing numbers of stimulations, apparently due to an immune reaction. Practically, up to 3 stimulations on average can be performed per female with the recovery of a reasonable number of high quality oocytes. The availability of monkey recombinant gonadotropins would allow the more efficient and extended use of females.

Laparoscopic Oocyte Recovery

Oocytes were collected by laporascopic follicular aspiration 27-33h after hCG injection via transabdominal needle aspiration of gravid ovarian follicles. Laparoscopy played a prominent role in the IVF laboratory, with most surgical procedures accomplished by the following steps:

1. Anesthetize monkeys with isoflurane gas vaporized in 100% oxygen. Comprehensive physiologic monitoring of animals should be conducted throughout the surgery, including ECG, peripheral oxygen saturation, and end-expired carbon dioxide. Orotracheal intubation and mechanical ventilation to maintain expired $CO_2$ at less than 50 mm Hg is mandatory.

2. Perform sterile skin preparation and draping after which the abdomen is insufflated with $CO_2$ at 15 mm Hg pressure.

Insert the viewing telescope via a small supraumbilical incision, with accessory ports placed in the paralumbar region.

3. Position the monkey in Trendeleburg, allowing the viscera to migrate in a cephalad direction exposing the reproductive organs.

4. Use a single small grasping forceps to stabilize the ovary for examination and needle aspiration. Rarely is a second accessory port and grasping forceps required for the experienced laparoscopist to perform this procedure.

5. After mobilization of the ovary, connect a 22 g hypodermic needle to a source of continuous vacuum (−120 mm Hg), and insert into individual follicles until all have been aspirated.

6. Reduce insufflation and close the incisions with interrupted absorbable suture in an intradermal pattern.

7. Place tubes containing follicular aspirates into a portable incubator (Minitube) at 37° C. and transport quickly to the lab. The time between aspiration and oocyte recovery should be minimized to avoid the detrimental effects of blood exposure, which usually contaminates the aspirates. The conventional approach of diluting aspirates with medium and searching for oocytes under dissecting a microscope is labor intensive often requiring 2-3 technicians. The recovery time can be minimized by sifting the aspirates through cell strainers.

8. Add 10× hyaluronidase stock solution directly to the tubes containing aspirates at 1:10 ratio and incubate at 37° C. for 30 sec.

9. Gently agitate the contents with a serological pipette to disaggregate cumulus and granulosa masses and pour the entire aspirate onto a cell strainer.

10. Oocytes are retained in the mesh, while blood, cumulus and granulosa cells are sifted through the filter.

11. Quickly backwash the strainer with TH3 medium and collect the medium containing oocytes in a Petri dish.

12. Rinse oocytes, which are now easily identified in TH3 medium.

13. Any remaining cumulus cells can be removed by manual clean up with a small bore pipette (approximately 125 μm in inner diameter).

14. Oocytes can be observed at higher magnification for determination of their developmental stage (GV, MI or MII) as well as quality (granularity, shape and color of the cytoplasm). On average, 40 oocytes are collected per stimulation, with over 70% matured or maturing (MII and MI stages).

15. After evaluation, transfer oocytes into chemically defined, protein-free HECM-9aa medium at 37° C. in 5% $CO_2$, until further use. Most MI stage oocytes should mature to the MII stage within 3-4 hours.

Modified Nuclear Transfer Procedures

Cell cultures of nuclear donor cells were established as described previously (Mitalipov, Yeoman et al. 2002). Briefly, tissue biopsy samples were washed in 0.5 mM EDTA in $Ca^{2+}$-free and $Mg^{2+}$-free Dulbecco PBS (Invitrogen, Carlsbad, Calif.) and minced into pieces before incubation in Dulbecco Modified Eagle's Medium (DMEM, Invitrogen) containing 1 mg/ml collagenase IV (Invitrogen) at 37° C. in 5% $CO_2$ for 20 min. Tissue pieces were then vortexed, washed and seeded into 75 $cm^3$ cell culture flasks (Corning, Acton, Mass.) containing DMEM supplemented with 100 IU/ml penicillin, 100 μg/ml streptomycin (Invitrogen), 10% FBS and cultured at 37° C. in 5% $CO_2$. Cells were synchronized in the $G_0/G_1$ phase of the cell cycle by culturing in medium with 0.5% FBS for 5 days after reaching confluency.

All micromanipulations were performed in TH3 medium. Recipient MII oocytes were transferred to the micromanipulation chamber with 30 μl of TH3 containing 5 μg/ml cytochalasin B, and incubated for 10-15 min before enucleation. The chamber was then mounted on an inverted microscope equipped with micromanipulators and Oosight™ Imaging System (CRI, Inc., Woburn, Mass.) for non-invasive, polarized light imaging and detection of the spindle based on birefringence. An individual oocyte was positioned using the holding pipette with the 1st polar body at approximately 2 o'clock. The metaphase spindle was visualized as a small string of bead shaped structures (chromosomal complexes) usually adjacent to the polar body. A beveled (22-25 µm outer diameter) or blunt Piezo-driven (10-15 µm outer diameter) enucleation pipette was inserted through the zona pellucida without piercing the oolemma and the spindle was slowly aspirated into the pipette and removed. Cultured donor cells were prepared as described above. A blunt transfer pipette (5-7 Mm outer diameter) was used to disrupt the membrane of a single donor cell by aspiration from a TH3 drop and the lysed cell with intact nucleus was subsequently injected into a cytoplast.

Alternatively, donor cell nuclear transfer was accomplished by electrofusion. Electrofusion procedures were similar to the conventional protocols described previously (Mitalipov, Yeoman et al. 2002; Mitalipov, Kuo et al. 2003) with the exception that calcium acetates were removed from the fusion buffer. A disaggregated donor cell was aspirated into a micropipette and transferred into the perivitelline space of the cytoplast. Cell fusion was induced by two 50 µsec DC pulses of 2.7 kV/cm (Electro Square Porator T-820, BTX, Inc., San Diego, Calif.) in 0.25 M D-sorbitol buffer containing 0.5 mM Hepes and 1 mg/ml fatty acid-free BSA. Successful fusion was confirmed visually 20-30 min after electroporation by the disappearance of the donor cell in the perivitelline space.

Reconstructed embryos were activated 2 hours after fusion by exposure by exposure to 5 mM ionomycin (CalBiochem, San Diego, Calif.) for 5 min in TALP/HEPES medium supplemented with 1 mg/ml BSA and then transferred for 5 min in TALP/HEPES medium supplemented with 30 mg/ml BSA and 2 mM 6-dimethylaminopurine followed by a 5 h incubation in HECM-9 medium containing 2 mM 6-dimethylaminopurine at 37° C. in 5% $CO_2$, 5% $O_2$ and 90% $N_2$. Activated SCNT embryos were placed in HECM-9 medium and cultured as described above.

Immunocytochemical Procedures of TSCs

Monkey oocytes and SCNT-derived totipotent cells were fixed in 4% paraformaldehyde for 20 min. After permeabilization with 0.2% Triton X-100 and 0.1% Tween-20, non-specific reactions were blocked with 10% normal goat serum (Jackson ImmunoResearch Laboratories, Inc., West Grove, Pa.). SCNT-derived totipotent cells were then incubated for 40 min in mouse monoclonal antibody against Oct-4 (POU5F1) or lamin A/C (1:200; Santa Cruz Biotechnology, Inc., Santa Cruz, Calif.). After extensive washing, SCNT-derived totipotent cells were exposed to affinity-purified goat anti-mouse, secondary antibody conjugated with indocarbocyanine (Cy3, 1:200; Jackson ImmunoResearch). SCNT-derived totipotent cells were then co-stained with 2 µg/ml of 4', 6-diamidino-2-phenylindole (DAPI) for 10 min, whole-mounted onto slides and examined under epifluorescence microscopy.

Genomic DNA Extraction and Amplification by PCR

Genomic DNA was isolated from individual blastocysts using QIAamp DNA Micro Kit (QIAGEN, Valencia, Calif.) according to the manufacturer's protocol. Somatic donor cell and SCNT-derived pluripotent cell gDNA was isolated using PUREGENE Cell and Tissue Kit (Gentra, Minneapolis, Minn.). A PCR-based method for the sexing of gDNA using size differences in the amplicons of the X- and Y-linked zinc finger protein genes (ZFX and ZFY was applied (Wilson and Erlandsson 1998). The primers used were:

```
For-5' ATTCCAGGCAGTACCAAACAG 3';  (SEQ ID NO: 103)

Rev-5' CCATCAGGGCCAATAATTATT 3'.  (SEQ ID NO; 104)
```

The primer set produced a 1149 bp fragment in both male and female samples, with an additional 771 bp fragment found only in male samples. The following primers were used to determine the presence of the neo cassette:

```
For-5' CTGAATGAACTGCAGGACGA 3'   (SEQ ID NO: 105)

Rev-5' AGCCAACGCTATGTCCTGAT 3'   (SEQ ID NO: 106)
```

PCR reactions were carried out in a 50 µl volume containing 250 ng of template gDNA, 0.2 uM of each primer, and 45 µl of Platinum PCR SuperMix High Fidelity (Invitrogen) containing a final concentration of 2.16 mM $MgSO_4$, 0.198 mM dNTPs. PCR conditions were as follows for both primer sets (denaturation/annealing/extension): 35 cycles 94/55/72° C. for 20/20/60 s. Amplicons were electrophoresed through 1.6% 0.5×TAE agarose gels stained with ethidium bromide and visualized on a UV transilluminator.

Derivation and Culture of PSCs from SCNT TSCs

Zonae pellucidae of selected expanded blastocysts were removed by brief exposure (45-60 sec) to 0.5% pronase in TH3 medium. For immunosurgical isolation of inner cell masses (ICMs) (Solter and Knowles 1975), zona-free blastocysts were exposed to rabbit anti-rhesus spleen serum (a gift from Dr. J. A. Thomson) for 30 min at 37° C. After extensive washing in TH3, embryos were incubated in guinea pig complement reconstituted with HECM-9 (1:2, v/v) for an additional 30 min at 37°. Partially lysed trophectodermal cells were mechanically dispersed by gentle pipetting with a small bore pipette (125 µm in inner diameter; Stripper pipette, Midatlantic Diagnostics Inc., Marlton, N.J.) followed by the rinsing of ICMs three times with TH3 medium. Isolated ICMs were plated onto Nunc 4-well dishes containing mitotically-inactivated feeder layers consisting of mouse embryonic fibroblasts (mEFs) and cultured in either DMEM medium with glucose and without sodium pyruvate (Invitrogen; Carlsbad, Calif.) supplemented with 1% nonessential amino acids (Invitrogen), 2 mM L-glutamine (Invitrogen), 0.1 mM β-mercaptoethanol and 20% FBS or DMEM/F12 medium (Invitrogen) with the same supplements but 15% FBS. Alternatively, whole zona-free blastocysts were plated on mEFs. Blastocysts and ICMs that attached to the feeder layer and initiated outgrowth were manually dissociated into small cell clumps with a microscalpel and replated onto new mEFs. After the first passage, colonies with ESC-like morphology were selected for further propagation, characterization and low temperature storage. Medium was changed daily and SCNT-derived pluripotent cell colonies were split every 5-7 days manually or by disaggregation in collagenase IV, (1 mg/ml, at 37° C. for 2-3 minutes; Invitrogen) and replating collected cells onto dishes with fresh feeder layers. Cultures were maintained at 37° C., 3% $CO_2$ and balance air or 3% $CO_2$, 5% $O_2$ and 92% $N_2$.

Embryoid Body Formation and In Vitro Differentiation of SCNT-Derived Pluripotent Cells For embryoid body (EB) formation, entire SCNT-derived pluripotent cell colonies were loosely detached from feeder cells and transferred into feeder-free, 6-well, Ultra Low adhesion plates (Costar, Corning Incorporated, Acton, Mass.) and cultured in suspension in ESC medium for 5-7 days. To induce further differentiation, EBs were transferred into collagen-coated, 6-well culture dishes (Becton Dickinson, Bedfort, Mass.) to allow attachment. To induce neuronal differentiation, medium was replaced with serum-free DMEM/F12 containing ITS supplement (insulin, transferrin and sodium selenite, Invitrogen) and fibronectin (5 g/ml; Invitrogen) (Kuo, Pau et al. 2003). Cultures were maintained for 7 days, with medium replenishment every 2 days. The resulting cultures were disaggregated with collagenase or trypsin treatment and replated onto polyornithine- and laminin-coated plates or glass coverslips in N2 medium consisting of DMEM/F12 supplemented with laminin (1 g/ml; Invitrogen), bFGF (10 ng/ml; R&D Systems, Minneapolis, Minn.), and N2 supplement (Invitrogen). Cultures were maintained for an additional 7 days with daily medium change. After 7 days, bFGF was omitted from the medium and cultures were maintained for an additional 7-12 days to induce differentiation into mature neuronal phenotypes. For pancreatic differentiation (C-peptide positive, endodermal lineage), initial steps were similar to neuronal differentiation. After expanding progenitor cells, bFGF was omitted and final differentiation was induced by supplementation of medium with 10 nM exendin-4 and 10 mM nicotinamide (StemCell Technologies Inc., Vancouver, Canada) (Lester, Kuo et al. 2004). Differentiation into cardiac cells or retinal pigment epithelium was initiated by EB formation in suspension as described above. EBs were then plated into collagen-coated dishes and cultures were maintained in ESC medium for 2-4 weeks.

Immunocytochemical Procedures of PSCs

Undifferentiated and differentiated SCNT-derived pluripotent cells were fixed in 4% paraformaldehyde for 20 min. After permeabilization with 0.2% Triton X100 and 0.1% Tween-20, non-specific reactions were blocked with 10% normal goat serum (Jackson ImmunoResearch Laboratories, Inc., West Grove, Pa.). Cells were then incubated for 40 min in primary antibodies, washed three times and exposed to secondary antibodies conjugated with fluorochromes (Jackson ImmunoResearch) before co-staining with 2 µg/ml 4',6-diamidino-2-phenylindole (DAPI) for 10 min, whole-mounting onto slides and examination under epifluorescence microscopy.

Primary antibodies were from Santa Cruz Biotechnology, Inc. (Santa Cruz, Calif.; OCT-4, SSEA-1, -3, -4, TRA-1-60, -1-81, THY-1, NANOG, FOXD3, bestrophin, CRALBP), Chemicon International, Inc. (Temecula, Calif.; C-peptide, neuron-specific nuclear protein (NeuN), microtubule-associated protein (MAP2C), β-III-tubulin (TujIII), glial fibrillary associated protein (GFAP), troponins I and T (cTnI and cTnT), alpha myosin heavy chain protein (α-MHC), slow tonic myosin heavy chain protein (sMHC), sarcoplasmic reticular $Ca^{2+}$-ATPase (SERCA2), atrial natriuretic peptide (ANP), tropomyosin, α-actinin, myosin light chain 2A and 2V (MLC-2V and MLC-2A), cardiac transcription factors GATA-4 and myocyte enhancer factor 2 (MEF-2)), ImmunoStar, Inc. (Hudson, Wis.; serotonin), R&D Systems, Inc. (Minneapolis, Minn.; nestin).

RT-PCR

Total RNA was extracted from ESCs and ESC-derived differentiated phenotypes using RNA purification kit (Invitrogen) according to the manufacturer's instructions. Total RNA was treated with DNAase I before cDNA preparation using SuperScript™ III First-Strand Synthesis System for RT-PCR (Invitrogen) according to the manufacturer's instructions. The first strand cDNA was further amplified by PCR using individual primer pairs for specific genes. The sequence, annealing temperature, and cycle number of each pair of primers is listed in supplemental Table 1. All PCR samples were analyzed by electrophoresis on 2% agarose gel containing 0.5 µg/ml ethidium bromide.

Microarray Analysis

Total RNA was isolated as indicated above. Labeling, hybridization and scanning was performed according to standard Affymetrix protocols (for more details see Affymetrix GeneChip Expression Analysis Technical Manual, rev.3. 2001). Microarray analysis was performed on a rhesus macaque Affymetrix GeneChip® with 52,865 probe-sets representing over 20,000 genes. The normalized microarray data was further analyzed using GeneChip Operating System (GCOS) 1.2. MAS-5 statistical analysis was performed to calculate the Signal Log Ratio (SLR) for each probe-set to determine the percentage of the transcriptome that significantly varied (p<0.002) between compared samples. Gene expression Fold Changes (FCs) between two samples were calculated from the SLR using the formula: $FC=(2\hat{}SLR)$. All normalized microarray data used in this research can be found in supplemental information in MicroarrayData1.xls and MicroaarrayData2.xls.

For the primary microarray comparison analysis, the $\log_{10}$ of the absolute detected signal for each present "P" probe set (p<0.05) was plotted in a scatter graph using Affymetrix GeneChip Operating Software (GCOS™) version 1.4. For the Correlation Value (CV) calculations the microarray data for each individual cell line comparison was filtered to only include probe sets present (p<0.05) in both cell lines. The present probe sets (PP) value details the number of probe sets, post filtering, with a present (p<0.05) signal in both compared cell lines. The Correlation Value (CV) for each cell line comparison was calculated using MAS-5™ (Affymetrix microarray suite 5) analysis to calculate the proportion of compared probe sets which demonstrated no significant change "NC" in gene expression. The cell lines examined included the adult skin fibroblast 19822 donor somatic cells (Donor cells) used to create CRES-1 and CRES-2 via SCNT, the IVF-embryo derived embryonic stem cell lines Oregon Rhesus Macaque Embryonic Stem (ORMES)-10 and -22 and the SCNT-embryo derived CRES (Cloned Rhesus Embryonic Stem)-1 and -2. Each cell line had three biological replicates and the letter after the cell line name details which replicate was utilized in the primary microarray comparison analysis. For the secondary gene specific analysis, comparison analysis was performed between each of the three control ORMES-10 biological replicates and each of the three somatic donor cell replicates, to give a total of nine somatic-ESC comparisons. The following selection criteria were used to identify rhesus somatic-specific genes: 1) genes that were considered to be present (P<0.05) in all three somatic donor cell replicates and 2) genes that demonstrated statistically significant decrease "D" in gene expression in the ORMES-10 replicates in all nine comparisons with the somatic donor cell replicates following GCOS comparisons with MAS-5 statistical analysis. A total of 4,998 somatic-specific probe sets were identified in this way. The following selection criteria were used to identify rhesus ESC-specific genes: 1) genes that were considered to be present (P<0.05) in all three ORMES-10 replicates and 2) genes that demonstrated a statistically significant increase "I" in gene expression in the ORMES-10 ESC replicates in all nine comparisons with the somatic donor cell replicates following GCOS comparisons with MAS-5 statistical analysis. A total of 6,178 ESC-specific probe set were identified in this way. The general approximation when working with large numbers of probe sets is to assume that each probe set represents hybridization to a single gene. However, multiple probe sets can exist for certain genes, so the actual number of genes included in the analysis is significantly lower than the number of probe sets analyzed. The somatic specific and ESC specific genes identified from this comparison analysis were then used to investigate if the CRES cell lines had successfully downregulated somatic specific genes and successfully upregulated ESC specific genes following comparison analysis with the three somatic donor cell replicates. For the tertiary stemness gene analysis, twelve stemness genes had the highest average fold change in gene expression when three undifferentiated biological replicates of ORMES-6 were compared to their in vitro differentiated counterparts and all twelve were significantly upregulated in five different rhesus monkey embryonic stem cell lines examined. Comparison analysis was performed between the ORMES and CRES cell line replicates and the donor somatic cell replicates and the average fold change (FC) increase in gene expression of the twelve stemness genes in the ORMES and CRES cell lines was calculated.

Cytogenetic Analysis

Mitotically active ESC lines (i.e., PSC lines) in log phase were incubated with 120 ng/mL ethidium bromide for 40 min at 37° C., 5% $CO_2$, followed by 120 ng/ml colcemid (Invitrogen) treatment for 20-40 min. Cells were then dislodged with 0.25% trypsin, and centrifuged at 200 g for 8 min. The cell pellet was gently resuspended in 0.075 M KCl solution and incubated for 20 min at 37° C. followed by fixation with methanol:glacial acetic:acid (3:1) solution. Fixed cells were dropped on wet slides, air dried and baked at 90° C. for 1 hour. G banding was performed using trypsin-EDTA and Leishman stain (GTL) by immersing slides in 1× trypsin-EDTA with 2 drops of 0.4M $Na_2HPO_4$ for 20 to 30 seconds. Slides were then rinsed in distilled water and stained with Leishman stain for 1.5 minutes, rinsed in distilled water again, and air dried. For GTL-banding analysis, 20 metaphases were fully karyotyped under an Olympus BX40 microscope equipped with 10× and 100× plan-apo objectives. Images were then captured and cells were karyotyped using a CytoVysion® digital imaging system (Applied Imaging, Pittsburgh, Pa.).

Mitochondrial DNA Analysis

For mitochondrial analysis, DNA was extracted from the relevant cell lines using commercial kits (Gentra, Minneapolis, Minn.). Samples required to identify mitochondrial inheritance in the CRES cell lines included both the CRES-1 and CRES-2 cell lines, cell lines derived from the oocyte donor females for CRES-1 and CRES-2 and somatic nuclear donor cell cultures used to create CRES-1 and -2. The rhesus monkey mitochondrial D-loop hypervariable region 2 (RhDHV2) sequence was amplified for each sample using primers RhDF2 (5' taa cat atc cga tca gag cc 3') and RhDR (5' tta aac acc ctc tac gcc g 3'). PCR for each sample was performed using Platinum PCR SUPERMIX™ (Invitrogen, Carlsbad, Calif.) containing 0.5 M of each primer (final volume 50 µl). Reaction conditions were initial denaturation at 94° C. for 2 min; 35 cycles of denaturation at 94° C. for 30 sec, annealing at 55° C. for 30 sec, extension at 72° C. for 90 sec and a final extension at 72° C. for 3 min, generating ~450 bp of sequence covering the RhDHV2 region. Products from these reactions were then sequenced to determine polymorphic variation in the RhDHV2 region by direct sequencing. The informative domain 1 (ID 1) sequence encompassing Macaca mulatta mitchondrion nucleotide positions (nps) 451-480 (GEN-BANK™ ACCESSION NO: NC_005943) was identified as containing single nucleotide polymorphisms (SNPs) informative for the mitochondrial inheritance of both CRES-1 and CRES-2. Each ID1 sequence was confirmed by three other sequencing reactions and all of the RhDHV2 chromatograms used were obtained with Sequencher v. 4.7 (GeneCodes, Ann Arbor, Mich.).

Example 2

Lamin A/C Expression and Nuclear Remodeling in Monkey Oocytes and Preimplantation Stage Embryos Lamin A/C, a nuclear lamina protein, has been considered as a marker of differentiated cells, however, its expression during mouse, pig and bovine preimplantation development is inconsistent (Schatten et al., Proc Natl Acad Sci USA 82(14): 4727-31, 1985; Prather et al., Biol Reprod 41(1): 123-32, 1989; Moreira et al., J Cell Sci 116(Pt 18): 3713-20, 2003; Sullivan et al., Biol Reprod 70(1): 146-53, 2004; Hall et al., Mol Reprod Dev 72(4): 471-82, 2005). The dynamics of lamin A/C appearance in monkey oocytes and in in vitro produced preimplantation stage embryos was examined, as detected by immunocytochemistry with a monoclonal antibody. A minimum of 6 oocytes/embryos produced from two independent experiments were examined per each developmental stage. Control experiments with primary or secondary antibody alone were negative. In germinal vesicle stage oocytes (GV), a high level of staining for lamin A/C was detected on the inner layer of the nuclear envelope. MI or MII arrested oocytes were negative for lamin A/C staining consistent with the absence of a nuclear membrane. Intense signal was associated with both pronuclei in zygotes produced by ICSI. However, lamin A/C reactivity was diminished and or dispersed in cleavage stage embryos up to the 8-cell stage. Strong nuclear staining reappeared at the 8-cell stage with intense lamin A/C signal observed in morulae before and after compaction. At the expanded or hatched blastocyst stages strong lamin A/C signal was present in trophectodermal cells but was relatively faint in the inner cell mass (ICM).

Example 3

Nuclear Remodeling in Monkey Embryos Produced by Conventional SCNT Protocols

Figure 2:
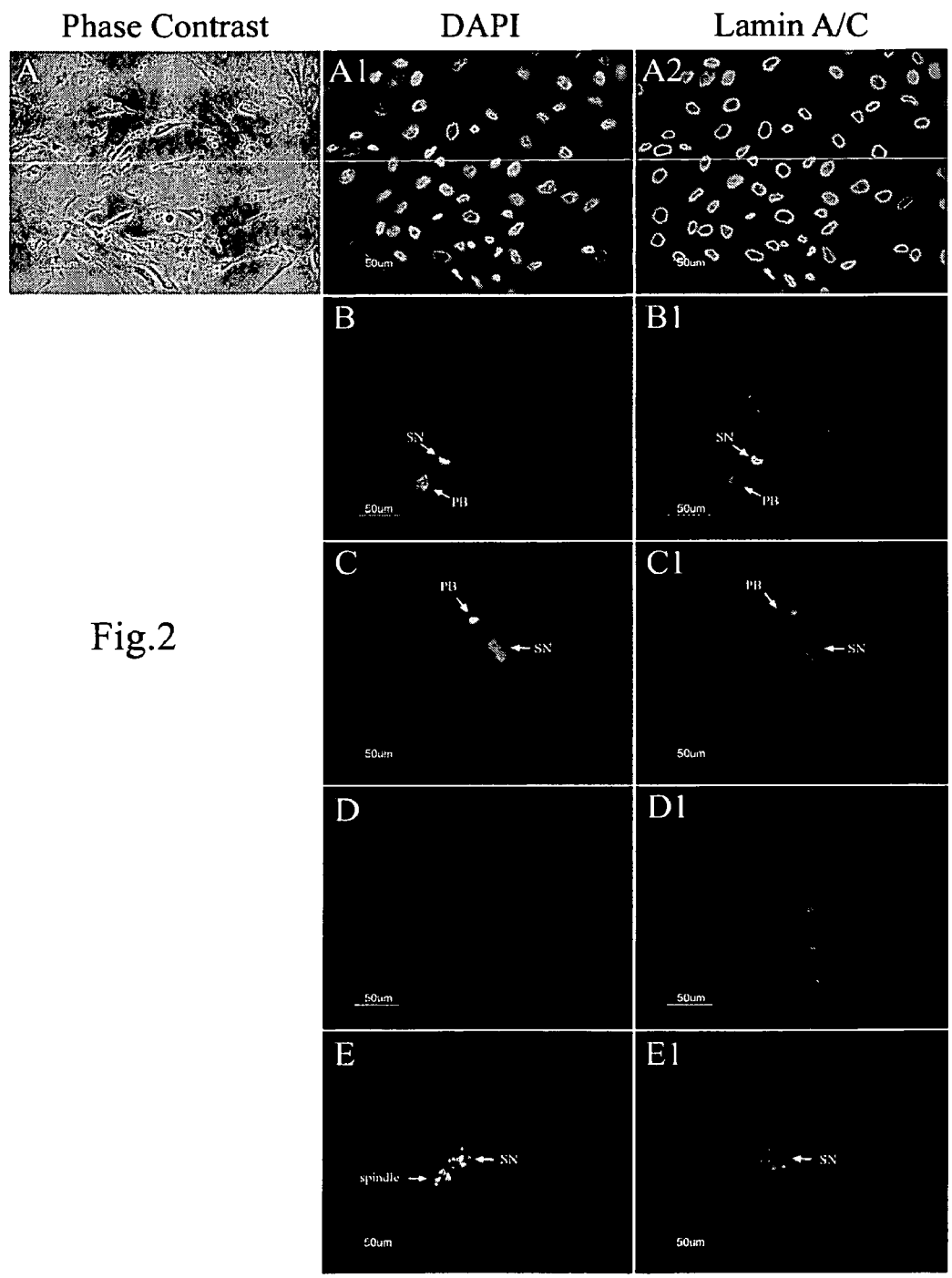
FIGS. 2A-2E are a set of digital images showing lamin A/C dynamics and nuclear remodeling in reconstructed monkey embryos produced following bisbenzimide and UV light exposure during spindle removal and nuclear donor cell introduction by electrofusion. DAPI staining was used throughout to localize cellular chromatin. A-A1-A2; Phase contrast image of donor fetal fibroblasts and strong lamin A/C staining of the nucleus. B-B1; A reconstructed embryo 1 hour after fusion showing minimal or no change in the donor nucleus. C-C1; A reconstructed embryo 4 hours after fusion exhibiting strong lamin A/C staining confined to the nuclear donor cell and indicative of the presence of an intact nuclear membrane. DAPI labeling shows incomplete chromatin condensation. D-D1; strong lamin A/C immunostaining persisted in cleaving, reconstructed embryos up to the 8-cell stage after which time embryos typically arrested. E-E1; a reconstructed embryo 4 h after fusion of a donor fibroblast with an intact (non-enucleated) MII oocyte. Note patchy nuclear membrane staining and significant chromatin condensation in the transferred nucleus consistent with efficient remodeling. The arrows localize the donor somatic cell nucleus (SN), spindle and the $1^{st}$ polar body (PB).

Conventional protocols for SCNT involving mechanical spindle extraction in the presence of the DNA stain, bisBenzimide, and UV exposure to confirm spindle removal (standard procedure in sheep, cattle and pigs (Fulka et al., Trends Biotechnol 22(6): 279-83, 2004)) with subsequent donor cell introduction by electrofusion have been largely unsuccessful in the monkey (Mitalipov et al., Biol Reprod 66(5): 1367-73, 2002; Similarly et al., Science 300(5617): 297 2003; Zhou et al., Human Reprod. 21: 2564-71, 2006). Failed SCNT embryo development was correlated with premature cytoplast activation as evidenced by incomplete nuclear remodeling detected with lamin A/C staining. As expected, donor fetal fibroblasts showed intense lamin A/C staining (FIG. 2A, see A1-A2). When introduced into non-activated cytoplasts by fusion, donor nuclei disappeared upon direct morphological evaluation. However, immunostaining for lamin A/C indicated the retention of intact nuclear lamina during 4 hours of observation (FIGS. 2B-B1 and 2C-C1) despite the fact that transferred nuclei underwent significant swelling (up to 3 times larger than the original). Moreover, co-staining with DAPI showed only minimal changes in donor cell chromatin after fusion, consistent with the absence of PCC. Following activation of fusion pairs induced by ionomycin/DMAP exposure, lamin A/C signal was also present in pronuclear stage embryos produced by SCNT. However, in contrast to control, ICSI-produced, embryos, intense lamin A/C signal was also maintained in early cleavage stage SCNT embryos albeit confined to the donor cell nucleus. When cultured in vitro, a high rate of developmental arrest at or beyond the 8-cell stage occurred in SCNT embryos, while over 60% of cleaved, fertilized control embryos progressed to the blastocyst stage (Table 1).

TABLE 1

Development of rhesus monkey SCNT embryos produced by conventional protocols

| Donor cells | Replications | N | PN and cleavage (%) | 8-cell[a] (%) | Morula[a] (%) | Compact morula[a] (%) | Blastocyst[a] (%) |
|---|---|---|---|---|---|---|---|
| OEC | 4 | 50 | 33 (66) | 8 (24) | 3 (9) | 1 (3) | 1 (3)[b] |
| Cumulus cells | 2 | 32 | 21 (66) | 8 (38) | 6 (28) | 1 (5) | 1 (5)[b] |
| Fetal fibroblasts | 5 | 77 | 58 (75) | 27 (46) | 12 (20) | 6 (10) | 0[b] |
| ICSI control | 14 | 80 | 72 (90) | 56 (78) | 55 (76) | 54 (75) | 46 (64)[c] |

PN—pronuclear stage zygotes;
OEC—oviductal epithelial cells;
[a]Percentages are calculated based on the number of cleaved embryos;
[b,c]Treatments with different superscripts within a column are significantly different ($P < 0.05$)

Failure to induce nuclear remodeling could reflect either inherently low MPF levels in MII oocytes recovered from ovarian stimulation protocols or loss of MPF resulting from premature oocyte activation during manipulation. In order to evaluate the first possibility, nuclear donor cells were fused with intact (non-enucleated) MII oocytes (n=13). Nine of 13 reconstructed embryos produced displayed patchy patterns of lamin A/C staining and chromatin condensation in the transferred nucleus consistent with timely remodeling (FIGS. 2, E-E1) and suggesting that at least not all MII oocytes were deficient in MPF. To test the hypothesis that failed nuclear remodeling reflects premature activation caused by the SCNT procedures and decline in MPF activity mediated by the proteasome system, proteasome catalytic activity was inhibited with MG-132 (Josefsberg et al., Biol Reprod 62(5): 1270-7, 2000; Zhou et al., *Science* 302(5648): 117 2003). In a pilot study, it was first determined that MG-132 at 5 µM was efficient in inhibiting first polar body extrusion during the MI to MII transition of monkey oocytes (Table 2).

dures. When sampled 1 hour after fusion, reconstructed embryos treated with MG-132 showed slight chromatin condensation and moderate lamin A/C staining, however, by 4 hours clear evidence of nuclear remodeling was obvious; weak or partial lamin A/C signal, robust chromosome condensation and spindle formation. These results support the assumption that conventional nuclear transfer steps induce a premature decline in MPF levels.

Premature activation could be induced by the electrofusion step (Mitalipov et al., Biol Reprod 65(1): 253-9, 2001). To evaluate this possibility, fusion pulses were applied to intact, control MII oocytes in fusion medium. Resumption of meiosis and second polar body extrusion was observed in all oocytes (5/5) within 1 hour indicating that the fusion procedure in monkeys can cause premature oocyte activation. This data, as a whole, demonstrates that premature cytoplast activation, secondary to conventional SCNT manipulations is responsible for failed nuclear remodeling and could account for the lack of developmental competence of monkey SCNT embryos.

Example 4

Nuclear Remodeling and Development in Monkey SCNT Embryos Produced by Modified Protocols In a comparative study of SCNT in monkeys, modified manipulation protocols involving spindle removal without

TABLE 2

Effect of various concentrations of MG-132 on inhibition of 1$^{st}$ polar body extrusion in monkey oocytes during the MI-MII transition and on subsequent in vitro development following fertilization by ICSI

| Oocyte stage | N | MG-132 concentration (µM) | Exposure time (hours) | # Matured during exposure | # Matured after exposure | # ICSI | # 8-cell | # Morula | # Blastocyst |
|---|---|---|---|---|---|---|---|---|---|
| MI | 5 | 5 | 4 | 0 | 4 | 4 | 1 | 0 | 0 |
| MI | 5 | 2 | 4 | 2 | 3 | 5 | 2 | 0 | 0 |
| MI | 5 | 0.5 | 4 | 3 | 1 | 4 | 3 | 3 | 3 |
| MI control | 17 | 0 | 0 | N/A | 14 | 14 | 12 | 10 | 9 |

Nevertheless, MG-132 exposure at the higher concentration preserved MPF activity in monkey cytoplasts and allowed an examination of the effect of nuclear transfer manipulations on premature activation and nuclear remodeling. Mature MII oocytes were exposed to 5 µM MG-132 immediately after retrieval and maintained in this inhibitor throughout enucleation and somatic donor cell fusion procedures. bisBenzimide/UV exposure and donor cell injection in one step (OSM) was superior to the conventional procedure described above (see also Zhou et al., supra 2006). A reduction in manipulation time was deemed important, perhaps minimizing any decline in MPF activity if and when premature activation occurred. Here, this assumption was challenged using two different methods for spindle extraction, namely the OSM under DIC optics as we described previously (Zhou et al., supra, 2006) and a two-step protocol. The two steps involved first use of spindle imaging system, OOSIGHT™ to directly visualize and extract the spindle (FIG. 2A) followed by donor nucleus introduction by direct injection employing a Piezo drill. To further protect the cytoplast from premature activation, intact oocyte incubations and manipulations were conducted in $Ca^{2+}$ and $Mg^{2+}$-free medium. Karyoplast staining with bisBenzimide confirmed successful enucleation in approximately 80% of manipulated oocytes under DIC optics and 100% with OOSIGHT™. Oocytes in which enucleation was not documented were discarded. While OSM required relatively long manipulation times secondary to achieving the optimal oocyte orientation for spindle identification, the use of OOSIGHT™ largely eliminated this limitation and spindle removal could routinely be accomplished in 1 minute.

When both these protocols were applied, SCNT embryos reconstructed with fetal fibroblasts showed loss of an organized lamin A/C signal and chromatin condensation within 2 hours of injection comparable to that observed in MG-132-treated cytoplasts. Concomitant with improved nuclear remodeling, 15% (10/67) of SCNT embryos created with OOSIGHT™ enucleation and direct injection reached the blastocyst stage in vitro compared to only 1% (3/235) ($P<0.05$) in the control SCNT group reconstructed using conventional enucleation with bisBenzimide/UV exposure and fusion. Moreover, similar to fertilized controls, lamin A/C signal in reconstructed embryos produced by the modified protocol was weak at the early cleavage stages with strong staining reappearing at the 8-cell stage. This lamin A/C re-expression coincides with the timing of embryonic genome activation in the monkey (Schramm and Bavister, Biol Reprod 60(3): 721-8 1999). At the blastocyst stage, reconstructed embryos revealed strong signal in the trophectoderm but reactivity to the lamin A/C antibody was diminished in the ICM. This was also analogous to ICSI-produced controls and consistent with appropriate reprogramming. MII oocytes collected during follicular aspiration or matured shortly (2-4 hours) during in vitro culture were equally efficient as donor cytoplasts for SCNT. Similar blastocyst development rates seen here with the two-step protocol using Oosight™ compared with the OSM described by us previously (Zhou et al., *Hum reproduction*, 2006) suggested that time differences in oocyte/cytoplast manipulation were not critical.

In the comparative study, only one fibroblast-like cell line and its subclone out of 4 lines tested was able to support SCNT embryo development (Zhou et al., supra, 2006). In order to eliminate the possibility that this donor cell was unique, the ability of other cell types to support SCNT and the in vitro development of reconstructed embryos to the blastocyst stage was examined. Fetal fibroblasts, adult male fibroblasts, female cumulus and oviductal epithelial cells and TERT immortalized fibroblasts (Kirchoff et al., Arch Virol 147(2): 321-33, 2002) supported timely blastocyst formation within eight days of culture (Table 3).

TABLE 3

The ability of different somatic nuclear donor cells to support the production of developmentally competent embryos in the rhesus monkey following modified SCNT protocols

| Donor cells | Replications | # Injected | # Cleaved (%) | # Blastocysts (%)[a] |
|---|---|---|---|---|
| ICSI control | 12 | 74 | 64 (87) | 31 (48)[b] |
| FF 15698 | 1 | 7 | 5 (71) | 1 (20)[b,c,d] |

TABLE 3-continued

The ability of different somatic nuclear donor cells to support the production of developmentally competent embryos in the rhesus monkey following modified SCNT protocols

| Donor cells | Replications | # Injected | # Cleaved (%) | # Blastocysts (%)[a] |
|---|---|---|---|---|
| FF 18019 | 2 | 18 | 13 (72) | 3 (23)[b,c,d] |
| Adult ear fibroblasts | 10 | 94 | 73 (78) | 21 (29)[c] |
| OEC | 2 | 15 | 15 (100) | 1 (7)[c,d] |
| Cumulus | 2 | 19 | 19 (100) | 3 (16)[c,d] |
| FF TERT | 7 | 73 | 49 (67) | 8 (16)[c,d] |
| HPRT1- | 17 | 156 | 138 (88) | 17 (12)[d] |

Figure 3:
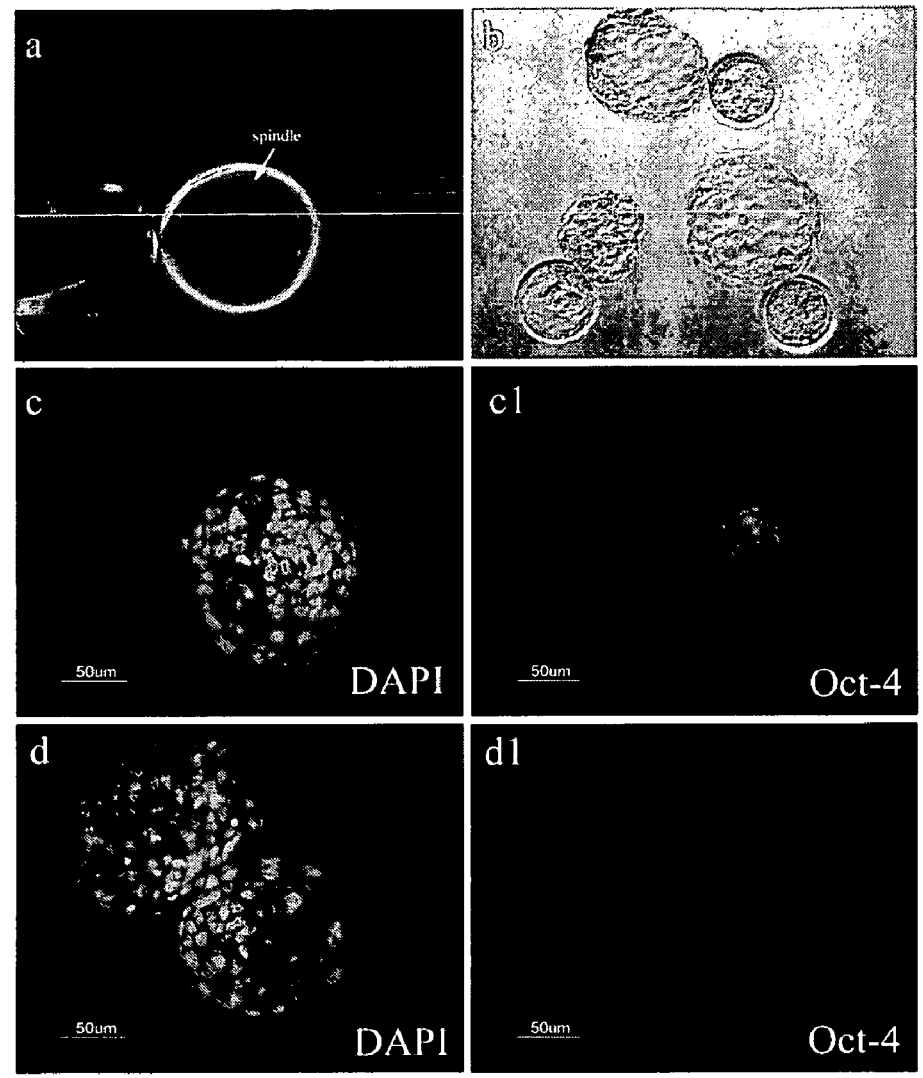
FIGS. 3A-3C are digital images.

Oct-4 (POU5F1) protein expression was examined by immunocytochemistry in individual SCNT blastocysts as a measure of successful nuclear reprogramming. A normal or control distribution pattern of Oct-4 expression was detected in 5 of 6 expanded SCNT blastocysts (FIG. 3A). The signal was localized to the ICM and down regulated in trophectodermal cells similar to that seen in ICSI-produced controls. It was demonstrated by PCR that male donor cell lines produced male embryos (FIG. 3B) eliminating the possibility that the reconstructed embryos were parthenotes and consistent with the results from karyotyping of individual SCNT blastocysts. When a gene targeted HPRT1- fibroblast cell line was employed as the nuclear donor cell source, the neo-containing insertion cassette was detected by PCR in both expanded SCNT blastocysts tested (FIG. 3C) indicating an origin from the donor nucleus genome.

Some donor cell types, particularly fibroblasts from aged adult monkeys, displayed larger cell size incompatible with direct injection into cytoplasts. Attempts to use larger diameter micropipettes for breaking the cell membrane and injecting such cells inevitably resulted in increased rates of cytoplast lysis. To address this issue, we revisited the donor cell electrofusion approach and modified the procedure by excluding $Ca^{2+}$ and $Mg^{2+}$ from the fusion buffer. Over 90% of adult male skin fibroblasts were successfully fused and blastocyst development was comparable to ICSI-fertilized controls (Table 4).

TABLE 4

Blastocyst development of monkey SCNT embryos produced by electrofusion

| Treatments | N | # cleaved | # Blastocysts forming by day 8 | # Blastocysts forming by day 12 |
|---|---|---|---|---|
| ICSI | 23 | 22 | 14 (64%) | 0 |
| SCNT control | 18 | 12 | 0 | 4 (33%) |
| SCNT plus caffeine | 19 | 13 | 4 (31%) | 0 |

However, the timing of blastocyst formation was significantly delayed in the fusion group with blastocysts cavitation observed at days 10-12 compared to the ICSI control or SCNT embryos produced by injection that typically formed blastocysts by day 8 (Table 4). It was reasoned that premature cytoplast activation during electrofusion could still occur and explain this outcome. To test another approach to avoid MPF degradation, SCNT embryos were incubated in 2.5 mM caffeine (protein phosphatase inhibitor) for 2 hours immediately after electrofusion. Caffeine treatment did not adversely affect cleavage and development as seen with MG-132. Moreover, SCNT embryos reached the blastocyst stage by day 8 (Table 4), further supporting the concept that high MPF levels and complete nuclear remodeling are essential for reprogramming and development following SCNT in primates.

Strategies designed to increase MPF and MAPK activities have been reported including the use of caffeine, a protein phosphatase inhibitor (Kawahara et al., supra, 2005; Lee and Campbell, supra, 2006) or the proteasome inhibitor, MG-132 (Zhou et al., supra, 2003). When used in SCNT protocols disclosed herein, these treatments increased the occurrence of remodeling events in the donor nucleus. Monkey oocytes are particularly vulnerable to premature activation and MPF degradation during in vitro manipulations, a likely characteristic of primates but with potential relevance to SCNT success in other mammals.

Reproductive cloning in nonhuman primates previously was concluded to be unachievable (Simerly et al., Dev Biol 276(2): 237-52, 2003). However, results of this study suggest that obstacles previously found in monkey SCNT are most likely due to incomplete reprogramming, and can be overcome by protocol alterations. Since conventional SCNT protocols have failed in monkeys, alternatives have been sought for a number of years. Modified protocols disclosed herein resulted in the production of reconstructed embryos that develop to the blastocyst stage in vitro using a variety of somatic cell types as the nuclear donor cell. Several changes in protocol appear fundamental to this success. The first involves spindle removal. BisBenzimide staining of oocytes followed by UV exposure is a standard enucleation procedure in many nuclear transfer protocols, for instance, resulting in live offspring in sheep, cattle and pigs (See, for example, Wells et al., Biol Reprod 57(2): 385-93, 1997; Cibelli et al., Science 280(5367): 1256-8, 1998; Wells et al., Biol Reprod 60(4): 996-1005, 1999; Polejaeva et al., Nature (London) 407(6800): 86-90, 2000). However, in the relatively transparent monkey oocyte, potential detrimental effects of bisBenzimide staining, UV illumination or a combination of both on the developmental potential of the reconstructed embryo were apparent. Secondly, spindle removal and/or introduction of the donor cell nucleus by electrofusion with concurrent activation of the recipient cytoplast was also implicated as a mechanism to account for premature cytoplast activation and SCNT failure. Electroporation in $Ca^{2+}$-containing fusion medium has resulted in increased intracellular calcium levels which, in turn, trigger a rapid decline in histone H1 kinase (Mitalipov et al., Biol Reprod 60(4): 821-7, 1999) and, possibly, MPF activity.

The electrofusion step (see FIG. 1) was substituted with direct intracytoplasmic injection of donor nuclei (Wakayama et al., Nature 394(6691): 369-74, 1998) or electrofusion in $Ca^{2+}$ and $Mg^{2+}$ free buffer. In addition, to further minimize the possibility of premature cytoplast activation, all manipulations were performed in $Ca^{2+}$- and $Mg^{2+}$-free medium. Under these modified conditions, lamin A/C profiles in reconstructed embryos were similar to those detected in sperm-fertilized control embryos. The achievement of reproducible blastocyst in vitro development rates from multiple donor cell types is a breakthrough that allows, for the first time, characterization of SCNT blastocysts in primates.

Example 5

Methods for Examples 6-8

Summary: A primary culture of fibroblasts was established from a skin biopsy of an adult rhesus macaque male (Male #1) and prepared for SCNT as previously described (Mitalipov et al., Biol Reprod 66, 1367-73, 2002). Mature metaphase II oocytes were rendered spindle-free using the Oosight™ Imaging System (CRI, Inc., Woburn, Mass.) and a donor somatic cell nucleus was introduced into a cytoplast through electrofusion. Reconstructed embryos were activated 2 hours after fusion by exposure to 5 μM ionomycin (CalBiochem, La Jolla, Calif.) for 5 min followed by a 5 hours incubation in 2 mM 6-dimethylaminopurine (DMAP), placed in HECM-9 medium and cultured at 37° C. in 6% $CO_2$, 5% $O_2$ and 89% $N_2$ until the expanded blastocyst stage. The ICMs of selected SCNT blastocysts were plated onto mEF feeder layers and cultured in ESC culture medium for 5-7 days. ICMs that attached to the feeder layer and initiated outgrowth were manually dissociated into small clumps with a microscalpel and replated onto fresh mEFs. After the first passage, colonies with ESC-like morphology were selected for further propagation, characterization, low temperature storage and in vitro and in vivo differentiation as previously described (Mitalipov et al., Stem Cells 24, 2177-86, 2006)

Somatic cell nuclear transfer: A primary culture of fibroblasts was established from an adult rhesus macaque male (Male #1) as previously described (Mitalipov et al, supra, 2006). Briefly, a small skin biopsy was surgically derived, washed in $Ca^{2+}$- and $Mg^{2+}$-free Dulbecco PBS (Invitrogen) and minced into pieces before incubation in Dulbecco Modified Eagle's Medium (DMEM, Invitrogen) containing 1 mg/ml collagenase IV (Invitrogen) at 37° C. in 5% $CO_2$ for 40 min. Tissue pieces were then vortexed, washed, seeded into 75 $cm^3$ cell culture flasks (Corning) containing DMEM supplemented with 100 IU/ml penicillin, 100 μg/ml streptomycin (Invitrogen), 10% FBS (DMEM/FBS culture media) and cultured at 37° C. in 5% $CO_2$ until reaching confluency. Fibroblasts were then disaggregated with trypsin treatment and frozen down in aliquots of $1 \times 10^6$ cells in medium containing 10% dimethyl sulphoxide (DMSO).

Fibroblasts were subsequently thawed, plated onto 4-well dishes (Nunc) and cultured under standard conditions until reaching 50-90% confluency. Cells were then synchronized in the $G_0/G_1$ phase of the cell cycle by culturing in DMEM medium with 0.5% FBS for 4 days prior to SCNT. Controlled ovarian stimulation and oocyte recovery has been described previously (Zelinski-Wooten et al., Hum Reprod 10, 1658-66, 1995). Cumulus-oocyte complexes were collected from anesthetized animals by laparoscopic follicular aspiration (28-29 h post hCG) and placed in TALP/HEPES medium (Bayister et al., Biol Reprod 16, 228-37, 1977) (modified Tyrode solution with albumin, lactate and pyruvate) containing 0.3% BSA (TH3) at 37° C. Oocytes were stripped of cumulus cells by mechanical pipetting after brief exposure (<1 min) to hyaluronidase (0.5 mg/ml) and placed in chemically defined, protein-free HECM-9 medium (Hamster Embryo Culture Medium)[37] at 37° C. in 6% $CO_2$, 5% $O_2$ and 89% $N_2$ until further use.

Recipient MII oocytes were transferred to 30 μl manipulation droplets of TH3 with 5 μg/ml cytochalasin B on a glass bottom manipulation dish (available from willcowells on the internet) covered with paraffin oil (Zander IVF) and incubated at 37° C. for 10-15 min before spindle removal. The chamber was then mounted on an inverted microscope (Olympus) equipped with the Oosight™ Imaging System (CRI, Inc.), glass stage warmer (Tokai Hit, available on the internet) and Narishige micromanipulators. The spindle was located and extracted by aspiration into an enucleation pipette (20-25μ outer diameter). Metaphase spindle removal was confirmed by its presence in the enucleation pipette. The OOSIGHT™ Imaging System allows non-invasive, polarized light imaging and detection of the spindle based on birefringence. Using this innovative approach, the oocyte spindle was quickly located and removed real-time with 100% efficiency. After oocyte spindle removal a disaggregated donor somatic cell was aspirated into a micropipette and placed into the perivitelline space of the cytoplast on the side opposite the 1$^{st}$ polar body. Cell fusion was induced by two 50 μsec DC pulses of 2.7 kV/cm (Electro Square Porator T-820, BTX, Inc.,) in 0.25 M D-sorbitol buffer containing 0.1 mM calcium acetate, 0.5 mM magnesium acetate, 0.5 mM Hepes and 1 mg/ml fatty acid-free BSA. Successful fusion was confirmed visually 30 min after electroporation by the disappearance of the donor cell in the perivitelline space. All nuclear transfer micromanipulation and fusion procedures were conducted on microscope stage warmers (Tokai Hit) maintaining 37° C. Reconstructed embryos were activated by exposure to 5 μM ionomycin for 5 min in TALP/HEPES medium supplemented with 1 mg/ml fatty acid-free bovine serum albumin (BSA) and then transferred for 5 min in TALP/HEPES medium supplemented with 30 mg/ml fatty acid-free BSA and 2 mM 6-dimethylaminopurine (DMAP) followed by a 5 hour incubation in HECM-9 medium containing 2 mM DMAP at 37° C. in 6% $CO_2$. Activated oocytes were placed in 4-well dishes containing HECM-9 medium supplemented with 10% FBS and 12 μM 2-mercaptoethanol (BME) and cultured at 37° C. in 6% $CO_2$, 5% $O_2$ and 89% $N_2$ for a maximum of 10 days with medium change every other day.

ESC derivation and culture: Zonae pellucidae of selected expanded SCNT blastocysts were removed by brief exposure (45-60 seconds) to 0.5% pronase in TH3 medium. A small proportion of embryos were either transferred directly to mouse embryonic fibroblasts (mEFs) as whole blastocysts or following mechanical dissection of the ICM. Remaining blastocysts were subjected to immunosurgical isolation of the ICMs as previous described (Mitalipov, supra, 2006). Briefly, zona-free blastocysts were exposed to rabbit anti-rhesus spleen serum for 30 min at 37° C. After extensive washing in TH3, embryos were incubated in guinea pig complement reconstituted with HECM-9 (1:2, v/v) for an additional 30 min at 37°. Partially lysed trophectodermal cells were mechanically dispersed by gentle pipetting with a small bore pipette (125 μm in inner diameter; Stripper pipette, Midatlantic Diagnostics Inc.,) followed by the rinsing of ICMs three times with TH3 medium. Isolated ICMs were plated onto Nunc 4-well dishes containing mitotically-inactivated feeder layers consisting of mouse embryonic fibroblasts (mEFs) and cultured in DMEM/F12 medium with glucose and without sodium pyruvate supplemented with 1% nonessential amino acids, 2 mM L-glutamine, 0.1 mM β-mercaptoethanol and 15% FBS at 37° C., 3% $CO_2$, 5% $O_2$ and 92% $N_2$. ICMs that attached to the feeder layer and initiated outgrowth were manually dissociated into small cell clumps with a microscalpel and replated onto new mEFs. After the first passage, colonies with ESC-like morphology were selected for further propagation, characterization and low temperature storage as previously described[17]. Medium was changed daily and ESC colonies were split every 5-7 days by manual dissociation and replating collected clumps onto dishes with fresh mEFs.

Example 6

SCNT Blastocyst Generation and Esc Derivation Efficiency

ESCs can differentiate into multiple cell types, representatives of which could be used in replacement therapy for aging or diseased cells and tissues. However, ESCs derived from in vitro fertilized (IVF) embryos are genetically divergent from the patient (allogenic) and thus any resultant transplanted cell would be rejected without the continual application of immunosuppressive drugs. One way to completely resolve the transplant rejection issue would be to generate ESCs that are genetically identical to the patient. This requires generation of blastocysts so that ESCs can be produced.

The primary culture of skin fibroblasts, used as the source of nuclear donor cells for SCNT, was established from a nine year old adult rhesus macaque male (Male #1). Mature metaphase II rhesus monkey oocytes were rendered spindle-free with the OOSIGHT™ spindle imaging system that uses polarized light to visualize the oocyte meiotic spindle. Analysis of the removed karyoplasts, for the presence of the meiotic spindles, consistently confirmed a 100% efficiency of spindle removal using this approach. The donor fibroblast nuclei were introduced into cytoplasts by electrofusion, incubated for two hours to allow nuclear remodelling to occur and subsequently activated and cultured to the blastocyst stage as described above. A 16% (35/213) blastocyst formation rate was observed with this nuclear donor cell line (Table 5).

TABLE 5

Rhesus monkey embryo development

| Procedure | Spindle visualization | N | Cleaved # (Mean % ± SEM) | 8-cell # (Mean %* ± SEM) | Morula # (Mean %* ± SEM) | CM # (Mean %* ± SEM) | Blastocyst # (Mean %* ± SEM) |
|---|---|---|---|---|---|---|---|
| ICSI** (control) | N/A | 40 | 38 (95% ± 5.4%) | 32 (84% ± 16%) | 29 (76% ± 14.7%) | 29 (76% ± 14.7%) | 19 (50% ± 13.3%) |
| SCNT† | Hoechst-UV | 165 | 120 (73% ± 8%) | 106 (88% ± 7%) | 32 (27% ± 9%) | 2 (2% ± 2%) | 1 (1% ± 1%) |
| SCNT | Oosight ™ | 304 | 213 (70% ± 4.8%) | 204 (96% ± 4.6%) | 199 (93% ± 5.3%) | 161 (76% ± 6.9%) | 35†† (16% ± 3.6%) |

N refers to the number of oocytes used fro SCNT and CM refers to the compact morula stage.
*The mean % for the 8-cell to blastocyst stages was calculated based on the number of cleaved embryos.
**ICSI refers to intra-cytoplasmic sperm injection
†This data was derived from our previous SCNT study[2]. It should be noted that a variety of different donor cells were used in these studies, none of which resulted in a significant blastocyst formation rate.
††Of these 35 SCNT blastocysts, 10 failed to expand, 5 collapsed and failed to re-cavitate and 20 were used for ESC isolation.

Figure 4:
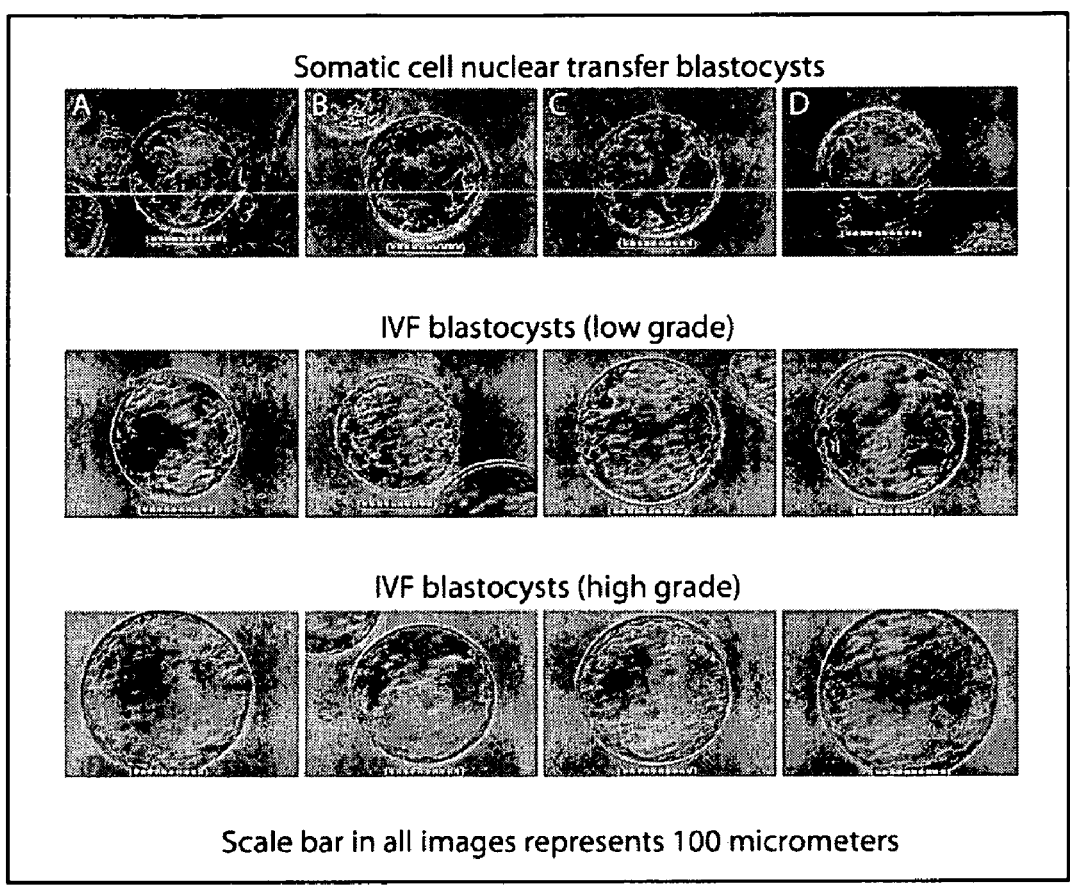
FIG. 4 is a set of digital images showing rhesus monkey embryo morphology. The first row demonstrates the morphology of rhesus monkey SCNT expanded and hatching blastocysts; the second row, low grade IVF-produced expanded blastocysts; and the third row, high grade IVF-produced expanded blastocysts.

SCNT blastocysts demonstrated a similar morphology to low grade IVF-produced blastocysts (FIG. 4). Twenty expanded or hatching SCNT blastocysts were used for ESC derivation via mechanical inner cell mass (ICM) isolation (n=2), immunosurgery (n=15) or direct culture of intact blastocysts (n=3) on mouse embryonic fibroblast (mEF) feeder layers. Two ESC lines (Cloned Rhesus Embryonic Stem; CRES-1 and -2) were derived, both following immunosurgery (10% derivation efficiency from blastocysts). Overall, 304 oocytes collected from 14 rhesus monkey females were used to generate two ESC lines, a 0.7% derivation efficiency from oocytes.

Example 7

Genetic Analysis and Pluripotency Assessment in CRES Cell Lines

As the number of mitochondria, each with 16.6 kb of mitochondrial DNA (Birky et al, *Proc Natl Acad Sci USA*. 92, 11331-8, 1995) (mtDNA), in the cytoplast dwarfs any mitochondrial contribution from the donor somatic cells, embryos derived by SCNT should predominantly, if not exclusively, possess mitochondria inherited from the oocyte. Therefore, ESCs derived from SCNT embryos should contain mtDNA identical to the female providing the recipient cytoplasts and nuclear DNA genetically identical to the male providing the nuclear donor cells. In order to investigate if the CRES-1 and CRES-2 cell lines contained the same nuclear DNA as the donor (Male #1) fibroblasts, microsatellite typing was performed using 39 short tandem repeat (STR) loci (Penedo et al., *Immunogenetics* 57, 198-209, 2005) and analysis of 56 single nucleotide polymorphisms (SNPs) (Ferguson et al., *Stem Cells* 24, 2177-86, 2006), 30 of which were informative for inheritance. Both the STR analysis, which included 25 common STR loci (Table 6) and 14 major histocompatibility complex (MHC) linked STRs (Table 7), and the SNP analysis (Table 8) demonstrated a complete match of both CRES lines to each other and to the nuclear DNA isolated from skin fibroblasts and peripheral blood leucocytes of Male #1.

TABLE 6

Short tandem repeat (STR) analysis of CRES cell lines

| STR loci | Female #1 oocyte donor for CRES-1 | Female #2 oocyte donor for CRES-2 | Male #1 somatic nuclear donor for CRES-1 and -2 | CRES-1 | CRES-2 | Female #3 oocyte donor for ORMES-22 | Male #2 sperm donor for ORMES-22 | ORMES-22 |
|---|---|---|---|---|---|---|---|---|
| Sex (AME) | XX | XX | XY | XY | XY | XX | XY | XX |
| D1S548 | 190/206 | 190/198 | 190/190 | 190/190 | 190/190 | 190/190 | 190/190 | 190/190 |
| D2S1333 | 301/301 | 293/301 | 289/301 | 289/301 | 289/301 | 273/293 | 285/289 | 273/285 |
| D3S1768 | 221/221 | 205/213 | 193/217 | 193/217 | 193/217 | 205/213 | 205/205 | 205/205 |
| D4S2365 | 283/283 | 275/287 | 283/283 | 283/283 | 283/283 | 283/283 | 283/283 | 283/283 |
| D4S413 | 131/131 | 133/145 | 131/139 | 131/139 | 131/139 | 131/145 | 125/141 | 131/141 |
| D5S1457 | 136/136 | 132/136 | 132/136 | 132/136 | 132/136 | 132/136 | 132/140 | 136/140 |
| D6S501 | 176/180 | 176/180 | 176/180 | 176/180 | 176/180 | 188/192 | 180/180 | 180/188 |
| D7S513 | 191/205 | 205/209 | 189/191 | 189/191 | 189/191 | 189/217 | 193/199 | 199/217 |
| D7S794 | 108/124 | 124/128 | 128/128 | 128/128 | 128/128 | 108/108 | 108/128 | 108/128 |
| D8S1106 | 144/144 | 148/160 | 144/148 | 144/148 | 144/148 | 148/168 | 160/168 | 168/168 |
| D9S921 | 183/195 | 183/191 | 179/179 | 179/179 | 179/179 | 183/195 | 175/195 | 183/195 |
| D10S1412 | 157/166 | 160/160 | 157/157 | 157/157 | 157/157 | 157/157 | 160/160 | 157/160 |
| D11S2002 | 256/256 | 256/256 | 260/264 | 260/264 | 260/264 | 252/252 | 256/260 | 252/256 |
| D11S925 | 308/338 | 310/316 | 308/310 | 308/310 | 308/310 | 308/308 | 338/338 | 308/338 |
| D12S364 | 282/290 | 282/288 | 281/290 | 281/290 | 281/290 | 282/290 | 268/296 | 268/290 |
| D12S67 | 121/129 | 192/204 | 117/125 | 117/125 | 117/125 | 117/133 | 109/117 | 109/133 |
| D13S765 | 228/240 | 212/220 | 228/256 | 228/256 | 228/256 | 216/236 | 228/228 | 228/236 |
| D15S823 | 333/349 | 329/353 | 329/361 | 329/361 | 329/361 | 357/385 | 345/353 | 345/385 |
| D16S403 | 164/168 | 156/158 | 158/164 | 158/164 | 158/164 | 152/164 | 152/152 | 152/164 |
| D17S1300 | 232/280 | 244/280 | 272/276 | 272/276 | 272/276 | 248/252 | 228/284 | 252/284 |
| D18S537 | 178/178 | 178/178 | 174/178 | 174/178 | 174/178 | 174/178 | 162/174 | 162/178 |
| D18S72 | 306/308 | 306/322 | 306/308 | 306/308 | 306/308 | 308/308 | 306/308 | 308/308 |
| D22S685 | 315/319 | 291/303 | 315/327 | 315/327 | 315/327 | 311/311 | 327/327 | 311/327 |
| MFGT21 | 113/115 | 117/119 | 115/115 | 115/115 | 115/115 | 111/113 | 115/125 | 113/125 |
| MFGT22 | 104/104 | 104/104 | 100/104 | 100/104 | 100/104 | 100/104 | 104/110 | 104/104 |

TABLE 7

Histocompatibility analysis of CRES cell lines and Male #1 based on MHC-linked STR analysis

| MHC loci | Male #1 nuclear donor for CRES-1 and -2 | CRES-1 | CRES-2 | Female #1 oocyte donor for CRES-1 | Female #2 oocyte donor for CRES-2 | Female #3 oocyte donor for ORMES-22 | Male #2 sperm donor for ORMES-22 | ORMES-22 |
|---|---|---|---|---|---|---|---|---|
| D6S291 | 206/208 | 206/208 | 206/208 | 206/208 | 208/214 | 206/216 | 210/216 | 210/216 |
| G51152 | 195/218 | 195/218 | 195/219 | 195/209 | 215/219 | 210/210 | 219/0 | 210/0 |
| 9P06 | 175/175 | 175/175 | 175/175 | 175/175 | 183/185 | 175/187 | 189/189 | 175/189 |
| DRA | 112/134 | 112/134 | 112/134 | 132/136 | 112/128 | 110/134 | 112/134 | 112/134 |
| MICA | 200/200 | 200/200 | 200/200 | 200/200 | 203/203 | 200/200 | 194/194 | 194/200 |
| 246K06 | 275/283 | 275/283 | 275/283 | 279/279 | 275/285 | 283/283 | 277/285 | 283/285 |
| 162B17A | 242/246 | 242/246 | 242/246 | 240/240 | 238/242 | 238/242 | 240/244 | 238/244 |

TABLE 7-continued

Histocompatibility analysis of CRES cell lines and Male #1 based on MHC-linked STR analysis

| MHC loci | Male #1 nuclear donor for CRES-1 and -2 | CRES-1 | CRES-2 | Female #1 oocyte donor for CRES-1 | Female #2 oocyte donor for CRES-2 | Female #3 oocyte donor for ORMES-22 | Male #2 sperm donor for ORMES-22 | ORMES-22 |
|---|---|---|---|---|---|---|---|---|
| 162B17B | 295/309 | 295/309 | 295/309 | 295/295 | 281/303 | 289/309 | 293/315 | 293/309 |
| 151L13 | 301/305 | 301/305 | 301/305 | 299/299 | 305/309 | 309/309 | 303/309 | 309/309 |
| MOGCA | 127/127 | 127/127 | 127/127 | 121/125 | 121/123 | 123/127 | 121/123 | 123/127 |
| 268P23 | 154/154 | 154/154 | 154/154 | 148/152 | 148/150 | 150/154 | 148/150 | 150/154 |
| 222I18 | 173/173 | 173/173 | 173/173 | 167/173 | 167/168 | 167/173 | 167/175 | 173/175 |
| D6S276 | 227/233 | 227/233 | 227/233 | 225/225 | 215/217 | 225/233 | 215/225 | 225/233 |
| D6S1691 | 197/199 | 197/199 | 197/199 | 197/205 | 203/203 | 197/216 | 197/203 | 197/203 |

TABLE 8

Single nucleotide polymorphism (SNP) analysis of CRES cell lines

| SNP | Male #1 Nuclear donor for CRES-1 and CRES-2 | CRES-1 | CRES-2 | Female #1 oocyte donor female for CRES-1 | Female #2 oocyte donor female for CRES-2 |
|---|---|---|---|---|---|
| ADRBK2_109 | A/A | A/A | A/A | A/A | A/G |
| AGRP_471 | C/C | C/C | C/C | C/C | C/T |
| CD74_213 | C/C | C/C | C/C | C/C | C/T |
| HTATSF1_636 | C/C | C/C | C/C | C/C | C/T |
| IFNG_312 | A/A | A/A | A/A | A/A | A/G |
| MAOA_116 | C/C | C/C | C/C | C/C | C/G |
| MPDZ_323 | A/G | A/G | A/G | A/A | A/A |
| CCL8_516 | A/G | A/G | A/G | G/G | A/A |
| CD4_558 | C/T | C/T | C/T | C/T | T/T |
| CXCL12_173 | C/C | C/C | C/C | T/T | C/C |
| IL2RA_124 | C/T | C/T | C/T | T/T | C/C |
| INHBB_131 | C/T | C/T | C/T | C/C | C/C |
| LRP8_647 | C/T | C/T | C/T | T/T | T/T |
| PYY_151 | C/T | C/T | C/T | T/T | C/T |
| SASH1_527 | A/G | A/G | A/G | G/G | A/G |
| SIRT1_277 | G/T | G/T | G/T | G/G | G/G |
| SLC6A4_132 | G/G | G/G | G/G | C/C | G/G |
| STAR_522 | G/G | G/G | G/G | G/G | G/T |
| TLR4_735 | C/T | C/T | C/T | T/T | T/T |
| XCL1_320 | C/C | C/C | C/C | C/T | T/T |
| CCR7_397 | G/T | G/T | G/T | G/G | G/T |
| CCRL1_54 | A/C | A/C | A/C | A/A | A/A |
| CD69_294 | C/C | C/C | C/C | C/T | C/T |
| CFTR_796 | G/G | G/G | G/G | A/G | A/G |
| CX3CR1_593 | A/A | A/A | A/A | G/G | G/G |
| IL1_755 | A/A | A/A | A/A | A/A | A/T |
| IL6ST_177 | G/G | G/G | G/G | A/G | G/G |
| CCR9_315 | C/C | C/C | C/C | C/T | C/T |
| SASH1_578 | A/A | A/A | A/A | A/A | C/C |
| FSHR_784 | C/C | C/C | C/C | C/G | C/G |

In contrast, DNA obtained from the oocyte donor females for CRES-1 (Female #1) and CRES-2 (Female #2) demonstrated no significant similarity to CRES-1 or CRES-2 (Tables 6-8). The genomic constitution of an IVF-derived rhesus monkey ESC line (ORMES-22[17]) and the ORMES-22 oocyte donor female (Female #3) and sperm donor male (Male #2) were also included to demonstrate STR allele inheritance (Tables 6-7).

Figure 5:
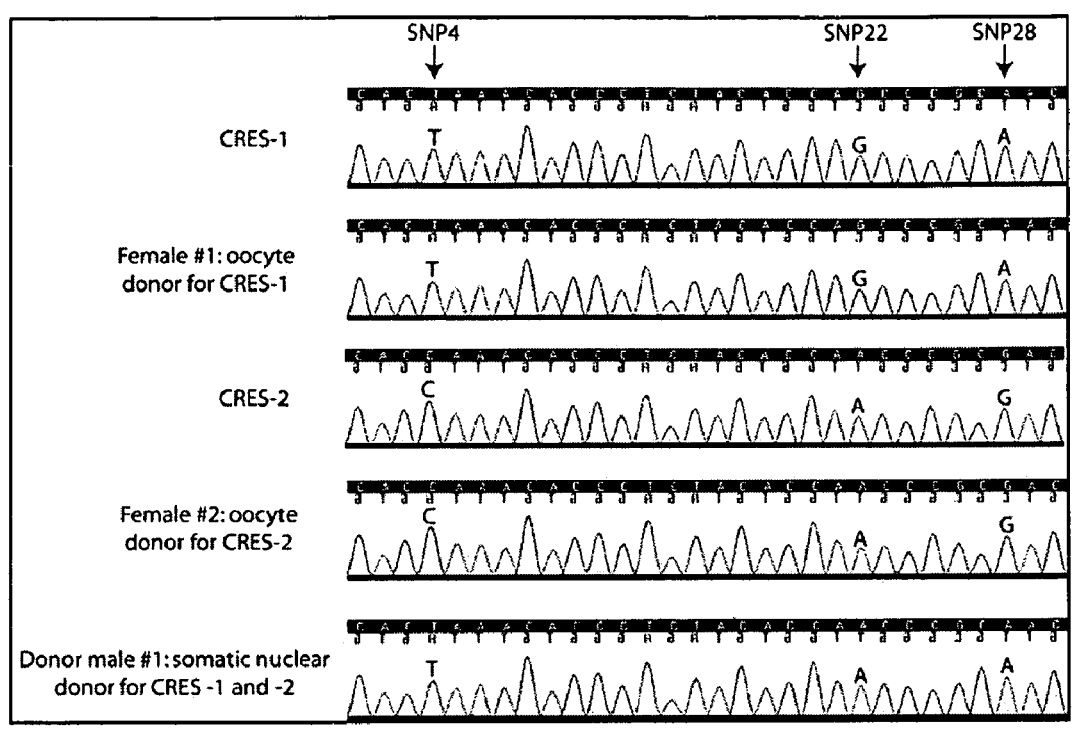
FIG. 5 is chromatograms of the rhesus macaque mitochondrial D-loop hypervariable region 2 informative domain 1 (RhDHV2-ID1). The informative domain 1 (ID1) sequence encompassed Macaca mulatta mtDNA nucleotide positions 451-480 (GENBANK® Accession No. NC_005943). Sequence analysis revealed that SNP22 (A/G) was informative for the mitochondrial inheritance for CRES-1 while SNP4 (C/T) and SNP28 (A/G) were informative for the mitochondrial inheritance for CRES-2. Results were confirmed by three independent sequences.

In order to investigate if the CRES-1 and CRES-2 cell lines contained the same mtDNA as their respective oocyte donor females, mtDNA sequence analysis was performed, investigating an informative domain 1 (ID1) in the rhesus monkey mitochondrial D-loop hypervariable region 2 (RhDHV2). This RhDHV2 sequence contained multiple informative SNPs including at ID1 nucleotide positions 4, 22 and 28 (FIG. 5). Analysis of SNP22 (an A/G polymorphism) demonstrated that CRES-1 mtDNA was derived from the oocyte donor Female #1 and not from the nuclear donor for CRES-1. Similarly, analysis of SNP4 (a C/T polymorphism) and SNP28 (an A/G polymorphism) confirmed that the CRES-2 mtDNA was derived from the CRES-2 oocyte donor Female #2 and not from the nuclear donor. Thus, microsatellite, SNP and mtDNA analyses verified that CRES-1 and CRES-2 contained nuclear DNA genetically identical to the nuclear donor fibroblasts and mtDNA inherited from oocytes, a hallmark of SCNT-produced ESCs and offspring.

Figure 6:
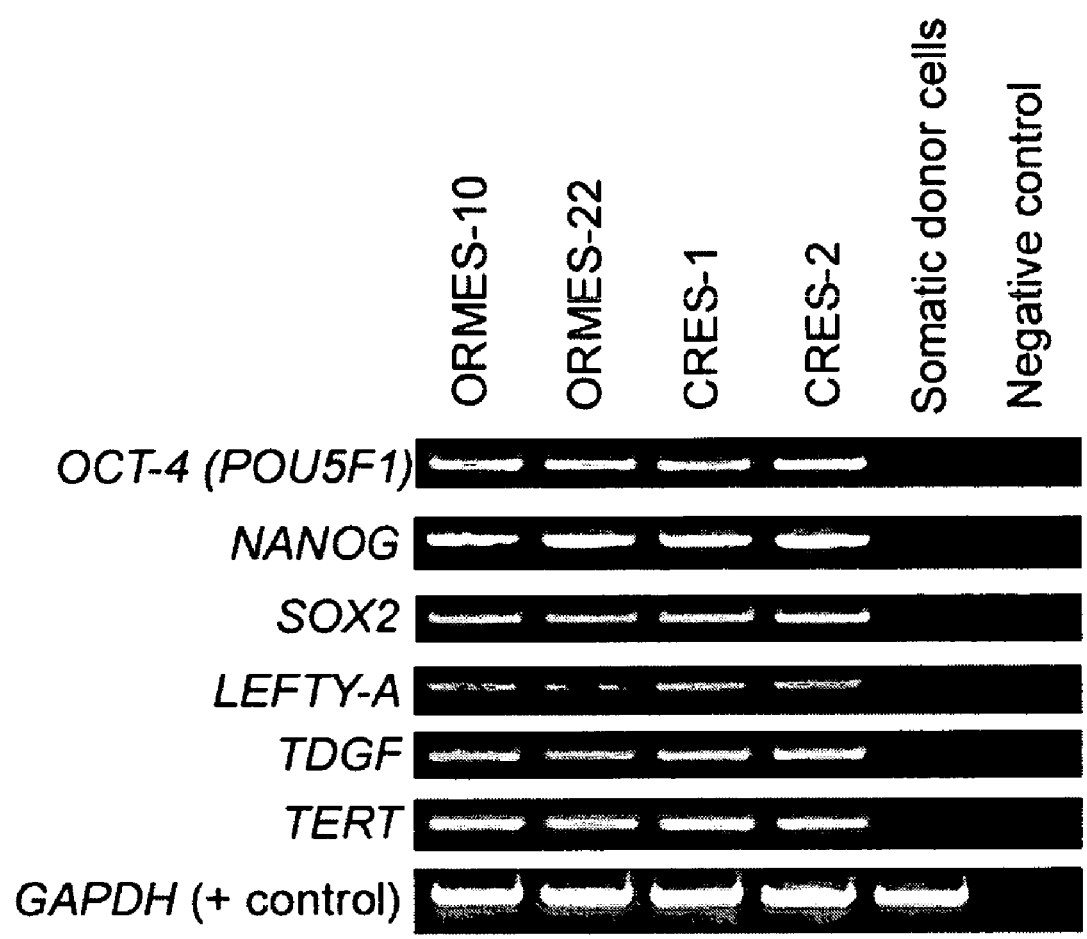
FIG. 6 is a digital image of an RT-PCR analysis of ESC-specific gene expression in CRES cells. OCT-4, NANOG, SOX-2, LEFTY-A, TDGF and TERT represent genes strongly expressed in primate ESCs, but not in somatic cells. GAPDH served as a housekeeping control.
Figure 7:
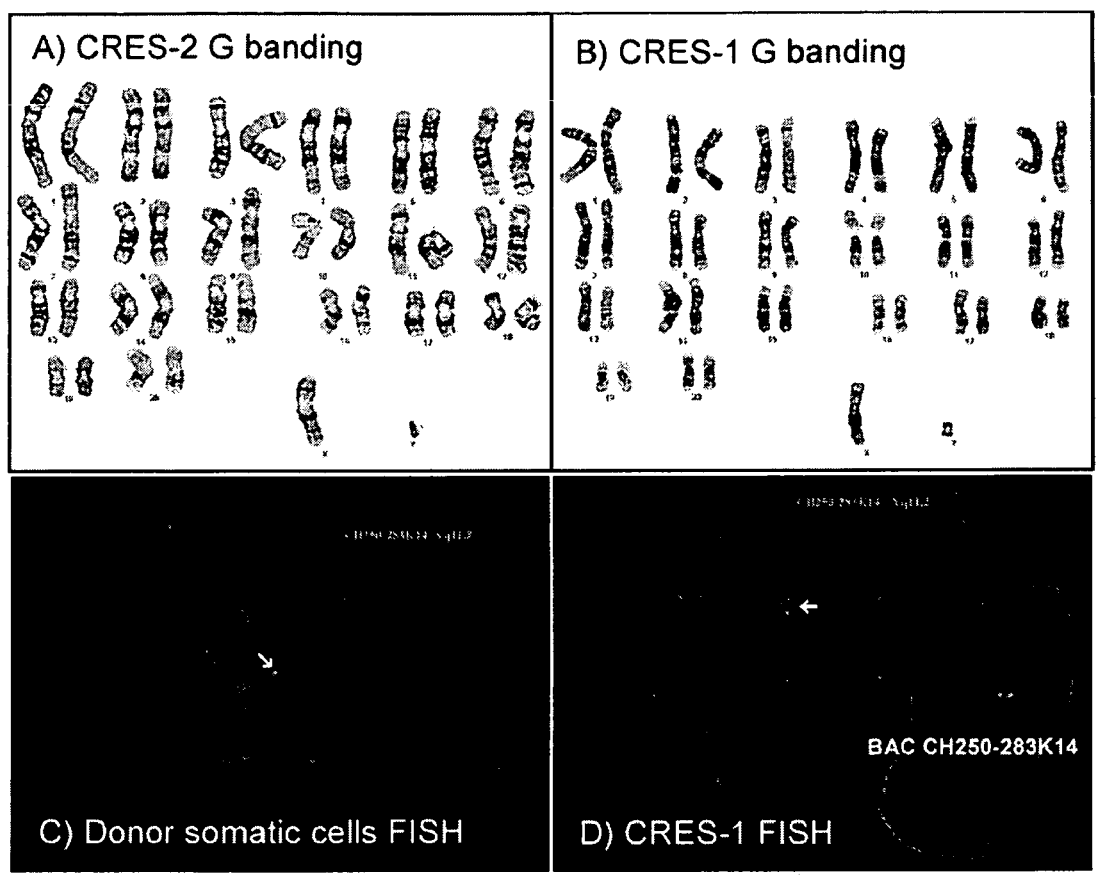
FIGS. 7A-7D are a set of digital images of the cytogenetic analysis of CRES cells.

Both CRES lines demonstrated typical ESC morphology, maintained an undifferentiated morphology following repeated manual passaging (>20 passages per line to date) and expressed key primate stemness markers including OCT4 (POU5F1), SSEA-4, TRA1-60 and TRA1-81 (as assayed by immunohistochemical analysis). Moreover, transcripts of other stemness genes including NANOG, SOX-2, LEFTY-A, TDGF and TERT were detected by RT-PCR analysis in both IVF-derived ESC controls (ORMES-10 and ORMES-22) and CRES cell lines (FIG. 6). Conventional cytogenetic G-banding analysis of the nuclear donor fibroblasts used for SCNT and the CRES-2 cell line (FIG. 7) demonstrated a normal male rhesus macaque chromosome (42, XY) complement in all cells analyzed. However, analysis of the CRES-1 cell line indicated the presence of three metaphase cells representing a hypodiploid clone characterized by loss of the Y chromosome and seventeen cells representing a diploid clone characterized by an isochromosome comprised of two copies of the long arm of the Y chromosome (41,X[3]/42,X,i(Y)q10)[17]) (FIG. 7B). Subsequent fluorescent in situ hybridization (FISH) analysis confirmed the G-banding findings; metaphase cells revealed the presence of a signal for BAC CH250-283K14 on both arms of the Y chromosome (FIG. 7D) indicating the presence of the i(Y)(q10) observed in the G-banding study. Additional studies were positive for loss of the Y chromosome in 12% of the CRES-1 cells analyzed.

Example 7

Transcriptional Profiling of CRES Cell Lines

Figure 8:
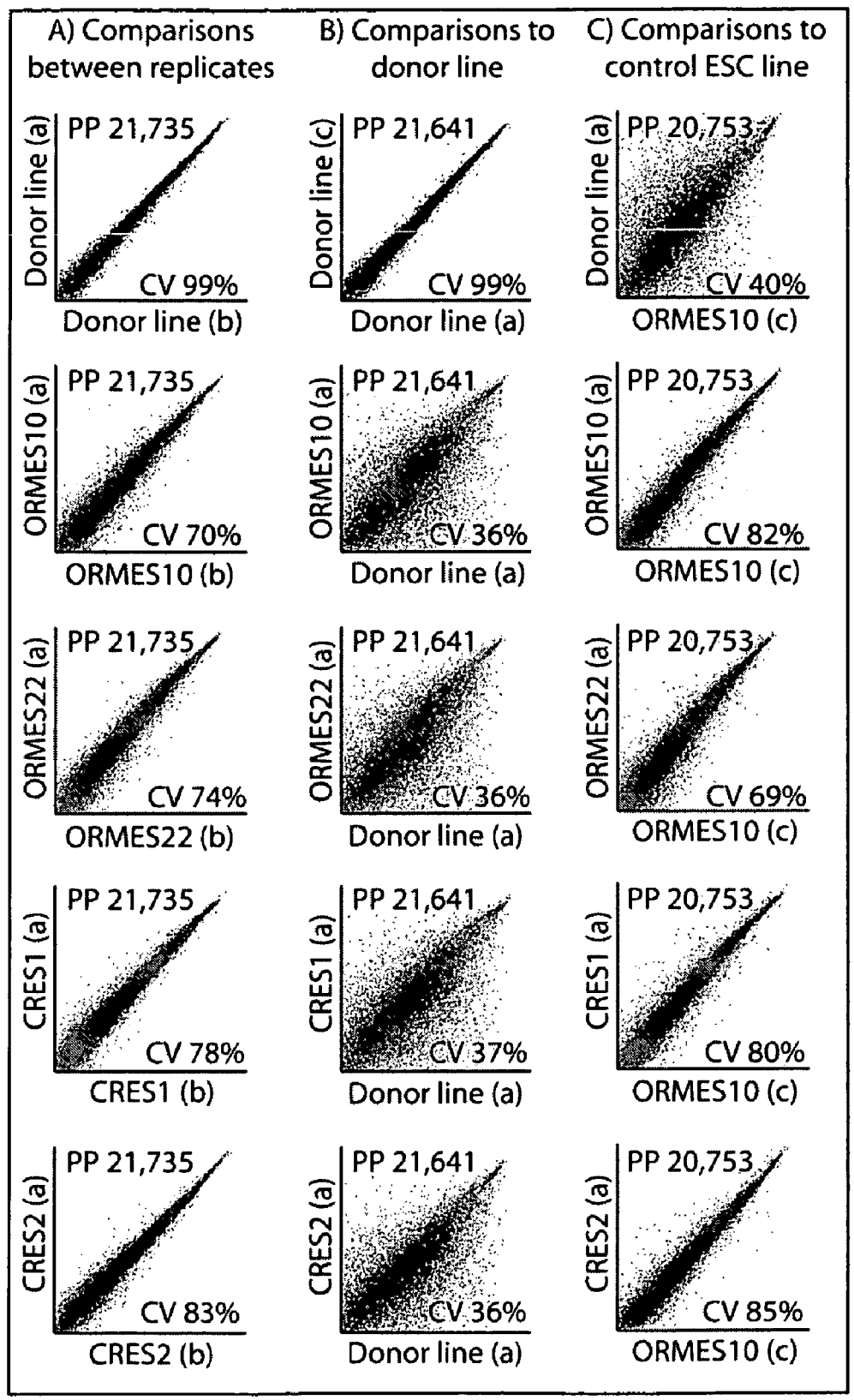
FIGS. 8A-8C are a set of plots of microarray analysis of rhesus monkey ESCs. Column A demonstrates selected comparisons between biological replicates of the same cell line, column B demonstrates selected comparisons between the cell lines and the somatic donor cell line and column C demonstrates selected comparisons between the cell lines and a control IVF-derived ESC line (ORMES-10).

Global transcription profiles of three biological replicates of each: Male #1 skin fibroblasts (nuclear donor for both CRES lines), both CRES-1 and -2 cell lines and two control ESC lines derived from fertilized embryos (ORMES-10 and -22) (Byrne et al., *Biol Reprod* 30, 30, 2006) were examined by Affymetrix microarray analysis. For the primary microarray comparison (accessible on the internet, see the Gene Expression Omnibus(GEO) website maintained through NCBI), three types of analyses were performed: A) replicates of each cell line were compared against each other; B) each cell line was compared against the somatic donor cell line; and C) each cell line was compared to a control IVF-derived ESC line. For each comparison, the detected signal for each present "P" probe set (p<0.05) was plotted in a scatter graph, the number of present probe sets (PP) used was recorded and the correlation value (CV) was calculated. All comparisons of control ORMES biological replicates with each other demonstrated a CV of greater than 60% and all unrelated sample comparisons (i.e. between ESC and somatic cell biological replicates) demonstrated a CV of significantly less than 60%, therefore a CV of 60% or greater was considered indicative of a significant transcriptional correlation. When the replicates of the somatic donor cells were compared, 99% transcriptional correlation was observed (FIG. 8, column A) suggesting that minimal artificial variation was introduced via the protocols used. While it was not possible to determine with certainty the degree of technical versus biological variation between replicates, it should be noted that all samples were processed identically and at the same time, and the level of technical variation between the donor somatic cell samples was 1% or less suggesting that the majority of the 20-30% transcriptional variation observed between ESC replicates was biological in origin. If so, ESCs show significant transcriptional plasticity not observed in somatic cells (FIG. 8, column A). Comparisons of the CRES cell lines to the somatic donor cells and control IVF-derived ESCs demonstrated that both CRES lines had fully reprogrammed into an ESC transcriptional state, with no significant transcriptional correlation between the CRES lines and the donor somatic cells (FIG. 8, column B) but a significant correlation between CRES cells and the control ESCs (FIG. 8, column C).

To identify ESC-specific genes, comparison analysis was performed between each of the three control ORMES-10 replicates and each of the three somatic donor cell replicates, to give a total of nine ESC-somatic comparisons. This set of ESC-comparisons identified 4,998 somatic cell-specific probe sets/genes and 6,178 ESC-specific probe sets/genes. Over 90% of the somatic cell-specific genes were significantly down regulated in the CRES cell line replicates and over 85% of the ESC-specific genes demonstrated significantly greater expression in the CRES cell line replicates (Table 9) when compared with the somatic donor cells.

TABLE 9

Analysis of ESC-specific gene expression in rhesus monkey stem cell lines

| Cell line | Biological replicate | # ESC genes* upregulated compared to donor line replicate A** | # ESC genes* upregulated compared to donor line replicate B** | # ESC genes* upregulated compared to donor line replicate C** |
|---|---|---|---|---|
| Nuclear donor cells | a | N/A | 21 (0.3%) | 47 (0.8%) |
| Nuclear donor cells | b | 30 (0.5%) | N/A | 77 (1.2%) |
| Nuclear donor cells | c | 18 (0.3%) | 13 (0.2%) | N/A |
| ORMES-22 | a | 5482 (89%) | 5388 (87%) | 5389 (87%) |
| ORMES-22 | b | 5558 (90%) | 5607 (91%) | 5644 (91%) |
| ORMES-22 | c | 5766 (93%) | 5672 (92%) | 5723 (93%) |
| CRES-1 | a | 5974 (97%) | 6001 (97%) | 5984 (97%) |
| CRES-1 | b | 5896 (95%) | 5919 (96%) | 5926 (96%) |
| CRES-1 | c | 5748 (93%) | 5845 (95%) | 5784 (94%) |
| CRES-2 | a | 5931 (96%) | 5843 (95%) | 5850 (95%) |
| CRES-2 | b | 5658 (92%) | 5552 (90%) | 5483 (89%) |
| CRES-2 | c | 5863 (95%) | 5933 (96%) | 5889 (95%) |

Transcriptional analysis of the control ORMES-22 replicates also demonstrated that over 90% of the somatic-specific genes had significantly less expression (Table 10) and over 85% of the ESC-specific genes had significantly greater expression (Table 11) when compared with the somatic donor cells.

TABLE 10

Analysis of somatic specific gene expression in rhesus monkey ESCs

| Cell line | Biological replicate | # somatic genes* down regulated compared to donor line replicate A** | # somatic genes* down regulated compared to donor line replicate B** | # somatic genes* down regulated compared to donor line replicate C** |
|---|---|---|---|---|
| Nuclear donor cells | a | N/A | 23 (0.5%) | 8 (0.2%) |
| Nuclear donor cells | b | 33 (0.7%) | N/A | 67 (1.3%) |
| Nuclear donor cells | c | 52 (1.0%) | 89 (1.8%) | N/A |
| ORMES-22 | a | 4822 (97%) | 4748 (95%) | 4756 (95%) |
| ORMES-22 | b | 4733 (95%) | 4728 (95%) | 4756 (95%) |
| ORMES-22 | c | 4741 (95%) | 4676 (94%) | 4721 (95%) |
| CRES-1 | a | 4822 (97%) | 4851 (97%) | 4824 (97%) |
| CRES-1 | b | 4807 (96%) | 4809 (96%) | 4827 (97%) |
| CRES-1 | c | 4671 (94%) | 4723 (95%) | 4727 (95%) |
| CRES-2 | a | 4856 (97%) | 4822 (97%) | 4820 (96%) |
| CRES-2 | b | 4752 (95%) | 4670 (93%) | 4668 (93%) |
| CRES-2 | c | 4800 (96%) | 4837 (97%) | 4812 (96%) |

TABLE 11

Analysis of ESC-specific gene expression in rhesus monkey stem cell lines

| Cell line | Biological replicate | # ESC genes* upregulated compared to donor line replicate A** | # ESC genes* upregulated compared to donor line replicate B** | # ESC genes* upregulated compared to donor line replicate C** |
|---|---|---|---|---|
| Nuclear donor cells | a | N/A | 21 (0.3%) | 47 (0.8%) |
| Nuclear donor cells | B | 30 (0.5%) | N/A | 77 (1.2%) |
| Nuclear donor cells | C | 18 (0.3%) | 13 (0.2%) | N/A |
| ORMES-22 | A | 5482 (89%) | 5388 (87%) | 5389 (87%) |
| ORMES-22 | B | 5558 (90%) | 5607 (91%) | 5644 (91%) |
| ORMES-22 | C | 5766 (93%) | 5672 (92%) | 5723 (93%) |
| CRES-1 | A | 5974 (97%) | 6001 (97%) | 5984 (97%) |
| CRES-1 | B | 5896 (95%) | 5919 (96%) | 5926 (96%) |
| CRES-1 | C | 5748 (93%) | 5845 (95%) | 5784 (94%) |
| CRES-2 | A | 5931 (96%) | 5843 (95%) | 5850 (95%) |
| CRES-2 | B | 5658 (92%) | 5552 (90%) | 5483 (89%) |
| CRES-2 | C | 5863 (95%) | 5933 (96%) | 5889 (95%) |

The final microarray analysis involved examining the level of expression of twelve putative rhesus monkey stemness genes identified in previous transcriptional profiling (Byrne et al., *Biol Reprod* 30, 30, 2006). These putative stemness genes had the highest average fold change in gene expression when undifferentiated ESC biological replicates were compared to their in vitro differentiated counterparts and all twelve were significantly upregulated in the five different ESC lines examined (Byrne et al., supra, 2006. All twelve stemness genes were significantly upregulated in all of the ORMES-10, ORMES-22, CRES-1 and CRES-2 replicates (accessible on the internet, see the Gene Expression Omnibus (GEO) website maintained through NCBI) and the average fold change in gene expression for both CRES-1 and CRES-2 was comparable to that for ORMES-10 and ORMES-22 when compared to somatic donor cell replicates (Table 12).

TABLE 12

Expression analysis of putative rhesus monkey stemness genes

| Affymetrix Probe Set ID | Stemness Gene* | Nuclear donor cells FC** | ORMES-10 FC** | ORMES-22 FC** | CRES-1 FC** | CRES-2 FC** |
|---|---|---|---|---|---|---|
| MmugDNA.26523.1.S1_s_at | NFE2L3 | 1 | 429 | 389 | 532 | 378 |
| MmuSTS.2285.1.S1_at | POU5F1 | 0 | 315 | 288 | 320 | 281 |
| MmugDNA.9427.1.S1_at | NR5A2 | 1 | 282 | 310 | 278 | 325 |
| MmugDNA.32128.1.S1_at | NANOG | 1 | 246 | 180 | 256 | 190 |
| MmuSTS.1436.1.S1_at | LCK | 1 | 179 | 206 | 218 | 94 |
| MmugDNA.11728.1.S1_at | VTCN1 | 1 | 245 | 139 | 153 | 125 |
| MmugDNA.42677.1.S1_at | DPPA4 | 4 | 154 | 117 | 178 | 78 |
| MmugDNA.28461.1.S1_at | SLC12A1 | 1 | 71 | 128 | 185 | 169 |
| MmugDNA.6836.1.S1_at | C14orf115 | 1 | 81 | 87 | 85 | 64 |
| MmuSTS.3122.1.S1_at | MYRIP | 0 | 71 | 51 | 75 | 53 |
| MmugDNA.15193.1.S1_at | ADH4 | 0 | 68 | 13 | 52 | 58 |
| MmuSTS.2310.1.S1_at | PRDM14 | 1 | 28 | 44 | 46 | 40 |

As a control, the relative fold change in expression for these putative stemness genes between the donor somatic cell replicates was insignificant (Table 12). Following analysis of global transcriptional profiles, the overall conclusion was that both CRES-1 and CRES-2 cells were transcriptionally similar to control ESC lines derived from IVF-produced blastocysts.

Example 8

Differentiation Potential of CRES Cell Lines

Figure 9:
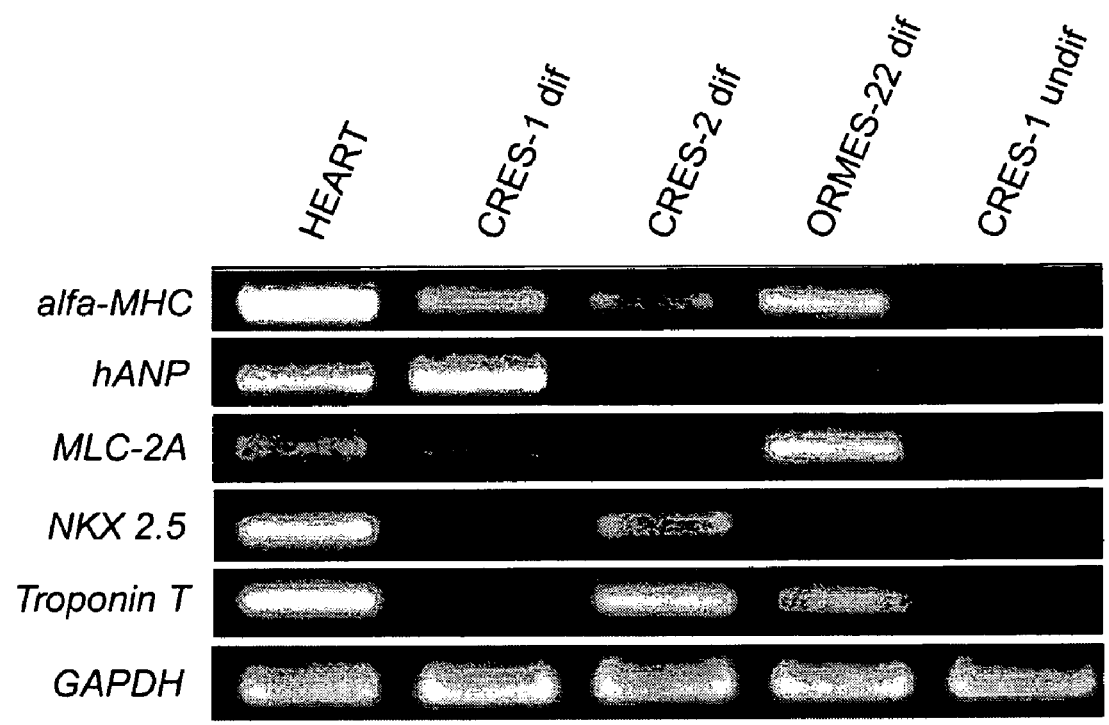
FIG. 9 is a digital image of an analysis of cardiomyocyte-specific gene expression in differentiated rhesus monkey ESCs. Both the control IVF-derived ESC line (ORMES-22) and the SCNT-derived ESC lines (CRES-1 and CRES-2) were differentiated into contracting cardiomyocytes as described in the Examples section. Transcripts of cardiac specific genes were detected in the control heart tissue and differentiated ESCs but not in undifferentiated CRES-1 cells.

To further define pluripotency, both CRES lines were exposed to conditions for cardiomyocyte differentiation in vitro (Mitalipove et al., Stem Cells 24, 2177-86, 2006). CRES-1 and CRES-2 efficiently produced contracting aggregates expressing markers of cardiac muscle tissue (FIG. 9). Directed neural differentiation resulted in efficient formation of various neuronal phenotypes, with elongated cellular morphology expressing neural markers, including microtubule-associated protein 2 (MAP2), β-III-tubulin and tyrosine hydroxylase (TH). When injected into severe combined immune deficiency (SCID) mice, both CRES lines formed teratomas and subsequent histological analysis identified representatives of all three germ layers confirming their pluripotent status. Immunohistochemical studies confirmed these results.

The results presented herein demonstrate for the first time that therapeutic cloning is possible in primates, provided an adequate source of SCNT blastocysts is available. A significant increase in SCNT blastocyst formation rate (from 1% to 16%) was achieved using the methods described herein when the oocyte spindle-removal step was performed without using Hoechst 33342 or UV light (Table 5). It is possible that the impaired blastocyst formation rate following conventional SCNT in primates may result from one or more of the following factors: Hoechst 33342 and/or UV damage to the relatively transparent primate oocyte, Hoechst 33342/UV induced oocyte activation and/or MPF degradation, reaction of the residual Hoechst 33342 in cytoplasts with the introduced donor cell DNA thereby impairing reprogramming and/or Hoechst 33342 contact with mitochondrial DNA, thus reducing cytoplast mitochondrial function.

In addition, "blind" enucleation techniques involving "squishing" (Simerly et al., Dev Biol 276, 237-52, 2004) or "one step manipulation" (OSM) (Zhou et al., Hum Reprod 21, 2564-71, 2006) were inefficient, because they failed to enucleate all oocytes. However, the OOSIGHT™ spindle imaging system supported rapid and highly efficient real time enucleation of primate oocytes. Introduction of the donor nucleus was accomplished by either direct injection or electrofusion; the latter was dictated here by the relatively large, donor cells employed. The SCNT blastocyst development rate was 16% of cleaved reconstructed embryos.

With an adequate supply of SCNT blastocysts, the final challenge in therapeutic cloning is ESC isolation. Several ICM isolation methods were examined, immunosurgical dispersal of the trophectoderm was effective. The derivation efficiency in the present study is within the range reported in the mouse, where the ESC derivation efficiency from SCNT embryos was 0.2%-3.4% per oocyte and 4%-10% per blastocyst (see, for example, Rideout et al., Cell 109, 17-27, 2002). Regarding the origin of the CRES lines, in addition to the 100% spindle removal efficiency, karyotype, microsatellite and SNP analyses confirmed that both CRES lines originated from SCNT embryos and not from parthenotes.

CRES lines demonstrated typical ESC morphology, self renewal capacity and expression of stemness markers. These cell lines were also transcriptionally similar to ESCs derived from IVF-produced blastocysts and pluripotent as evidenced by the generation of representatives of all three germ layers following in vivo teratoma formation. Our results confirm the possibility that pluripotent ESCs can be produced via SCNT. The CRES-1 cell line revealed a translocation of unknown origin characterized by an isochromosome comprised of two copies of the long arm of chromosome Y while CRES-2 exhibited a normal male karyotype.

The primary rationale for therapeutic cloning is transplantation of histocompatible ESC-derived phenotypes back into the patient. The MHC profile of both CRES lines perfectly matched the donor male in all MHC loci examined via microsatellite analysis, suggesting that transplantation of differentiated derivatives back into the donor animal would not lead to rejection.

In summary, pluripotent ESCs have been generated from rhesus monkey cloned embryos. These ESCs that were generated: 1) have a similar morphology to control ESC lines derived from IVF-produced embryos; 2) express markers characteristic of ESCs; 3) are transcriptionally similar to control ESC lines; and 4) possess the potential to differentiate into multiple cell types.

Example 9

Improving Efficiency

As described below, further optimizations in SCNT and ES cell derivation protocols significantly improve efficiency of this approach resulting in high blastocysts formation and ES cell isolation rates similar to that reported for fertilized embryos. A cohort of oocytes, retrieved from one female after a single controlled ovarian stimulation was used for SCNT with adult female monkey skin cells to produce two ES lines. Evaluation of ES cell-specific marker expression, confirmed the ability of the cells to differentiate in vitro and in vivo into various cell types including germ cells confirmed that these cells are indeed pluripotent. Moreover, detailed analysis including imprinted gene expression, methylation, telomere length and X inactivation demonstrated remarkable extent of epigenetic reprogramming of somatic cells to ES cells. The results are disclosed below.

The first modification was implemented to avoid deleterious effects of Hoechst staining and UV exposure during enucleation steps on the cytoplast integrity. This involved visualization of the metaphase spindle during enucleation with the OOSIGHT™ imaging system. This modification alone resulted in a significant increase in the blastocyst formation rate after SCNT, and subsequent isolation of two ESC lines from these embryos (see above). Premature activation could also be induced by electrofusion pulses in $Ca^{2+}$-containing fusion buffer, as described above. Thus, a $Ca^{2+}$-free fusion buffer was employed to avoid MPF decline during the electrofusion procedure. In vitro development of SCNT embryos was examined. In three separate experiments, 59 monkey metaphase II (MII) oocytes collected from three females were enucleated and fused with skin fibroblasts isolated from an adult female rhesus monkey (Female #1) (Table 13).

TABLE 13

In vitro development of monkey SCNT embryos

| Animals | # Oocytes | # Cleaved | # Compact Morulae | # Blastocysts |
|---|---|---|---|---|
| Oocyte donor #1 | 19 | 19 (100%) | 7 (37%) | 7 (37%) |
| Oocyte donor #2 | 30 | 30 (100%) | 19 (63%) | 14 (47%) |
| Oocyte donor #3 | 10 | 9* (90%) | 6 (67%)** | 4 (44%)** |
| TOTAL | 59 | 58 (98) | 32 (55%)** | 25 (43%)** |

After artificial activation and in vitro culture, twenty-five expanded SCNT blastocysts were recovered (a 43% blastocyst rate). Next, eighteen blastocysts produced in this experiment were used for ES cell isolation and two alternative approaches were tested: conventional inner cell mass (ICM) isolation involving immunosurgical dispersal of trophectodermal cells (see above) and whole (intact) blastocyst culture (Table 14).

TABLE 14

ES cell isolation from SCNT blastocysts

| Animals | ES cell isolation approach | # Blastocysts used | # ES cell lines isolated |
|---|---|---|---|
| Oocyte donor #1 | Conventional* | 1 | 0 |
| Oocyte donor #2 | Conventional* | 7 | 0 |
| | Whole embryo** | 6 | 2 (33%) |
| Oocyte donor #3 | Conventional* | 3 | 0 |
| | Whole embryo** | 1 | 0 |
| TOTAL | Conventional* | 11 | 0 |
| | Whole embryo** | 7 | 2 (29%) |

Isolated ICMs (n=11) and intact blastocysts (n=7) were plated onto feeder layers consisting of mouse embryonic fibroblasts (mEFs) according to the methods described above. Subsequent passaging resulted in two ES cell lines (designated as CRES-3 and -4) both derived from whole blastocysts (a 29% derivation rate). These results represent a significant increase in SCNT blastocyst development (from 16% to 43%) and ES cell isolation (from 10% to 29%) rates over the previous efficiency rate, resulting in a significant reduction in the number of oocytes required to produce a single ES cell line. Moreover, isolation of two ES cell lines using oocytes retrieved from one female demonstrates both the technical and financial feasibility of deriving patient-matched ES cells for the treatment of degenerative diseases.

Example 10

Origin and Pluripotency Analysis of Novel CRES Cells

CRES-3 and -4 grew as flat colonies typical for monkey ES cells and immunocytochemical analysis confirmed expression of key primate pluripotency markers including OCT4, TRA1-60, TRA1-81 and SSEA-4. Detailed genetic analysis of nuclear DNA employing 40 microsatellite (STR) markers indicated a complete homology of both CRES-3 and -4 to each other and to nuclear donor fibroblasts with no significant similarity to the oocyte donor genomic DNA (Table 15).

TABLE 15

Microsatellite analysis of CRES-3 and -4

| Microsatellite markers | CRES-3 | CRES-4 | SOMATIC NUCLEAR DONOR Female #1 | OOCYTE DONOR #3 |
|---|---|---|---|---|
| SEX | XX | XX | XX | XX |
| D1S548 | 190/206 | 190/206 | 190/206 | 190/194 |
| D2S1333 | 301/301 | 301/301 | 301/301 | 289/293 |
| D3S1768 | 221/221 | 221/221 | 221/221 | 201/225 |
| D4S2365 | 283/283 | 283/283 | 283/283 | 283/283 |
| D4S413 | 131/131 | 131/131 | 131/131 | 131/145 |
| D5S1457 | 136/136 | 136/136 | 136/136 | 132/132 |
| D6S501 | 176/180 | 176/180 | 176/180 | 180/180 |
| D7S513 | 191/205 | 191/205 | 191/205 | 191/205 |
| D7S794 | 108/124 | 108/124 | 108/124 | 108/128 |
| D8S1106 | 144/152 | 144/152 | 144/144 | 140/168 |
| D9S921 | 183/195 | 183/195 | 183/195 | 179/191 |
| D10S1412 | 157/166 | 157/166 | 157/166 | 157/157 |
| D11S2002 | 256/256 | 256/256 | 256/256 | 244/264 |
| D11S925 | 308/338 | 308/338 | 308/338 | 308/308 |
| D12S364 | 282/290 | 282/290 | 282/290 | 284/290 |
| D12S67 | 121/129 | 121/129 | 121/129 | 117/188 |
| D13S765 | 228/240 | 228/240 | 228/240 | 220/232 |
| D15S823 | 333/349 | 333/349 | 333/349 | 353/361 |
| D16S403 | 164/168 | 164/168 | 164/168 | 156/164 |
| D17S1300 | 232/280 | 232/280 | 232/280 | 236/240 |
| D18S537 | 178/178 | 178/178 | 178/178 | 162/174 |
| D18S72 | 306/308 | 306/308 | 306/308 | 306/308 |
| D22S685 | 315/319 | 315/319 | 315/319 | 327/331 |

TABLE 15-continued

Microsatellite analysis of CRES-3 and -4

| Microsatellite markers | CRES-3 | CRES-4 | SOMATIC NUCLEAR DONOR Female #1 | OOCYTE DONOR #3 |
|---|---|---|---|---|
| DXS2506 | 262/262 | 262/262 | 262/262 | 262/282 |
| MFGT21 | 113/115 | 113/115 | 113/115 | 115/117 |
| MFGT22 | 104/104 | 104/104 | 104/104 | 104/104 |
| D6S291 | 206/208 | 206/208 | 206/208 | 208/216 |
| G51152 | 195/209 | 195/209 | 195/209 | 208/209 |
| 9P06 | 175/175 | 175/175 | 175/175 | 185/191 |
| DRA | 132/136 | 132/136 | 132/136 | 114/136 |
| MICA | 200/200 | 200/200 | 200/200 | 203/203 |
| 246K06 | 279/279 | 279/279 | 279/279 | 270/283 |
| 162B17A | 240/240 | 240/240 | 240/240 | 238/244 |
| 162B17B | 295/295 | 295/295 | 295/295 | 289/325 |
| 151L13 | 299/299 | 299/299 | 299/299 | 303/305 |
| MOGCA | 121/125 | 121/125 | 121/125 | 121/127 |
| 268P23 | 148/152 | 148/152 | 148/152 | 148/154 |
| 222I18 | 167/173 | 167/173 | 167/173 | 167/173 |
| D6S276 | 225/225 | 225/225 | 225/225 | 215/225 |
| D6S1691 | 197/205 | 197/205 | 197/205 | 197/210 |

Figure 10:
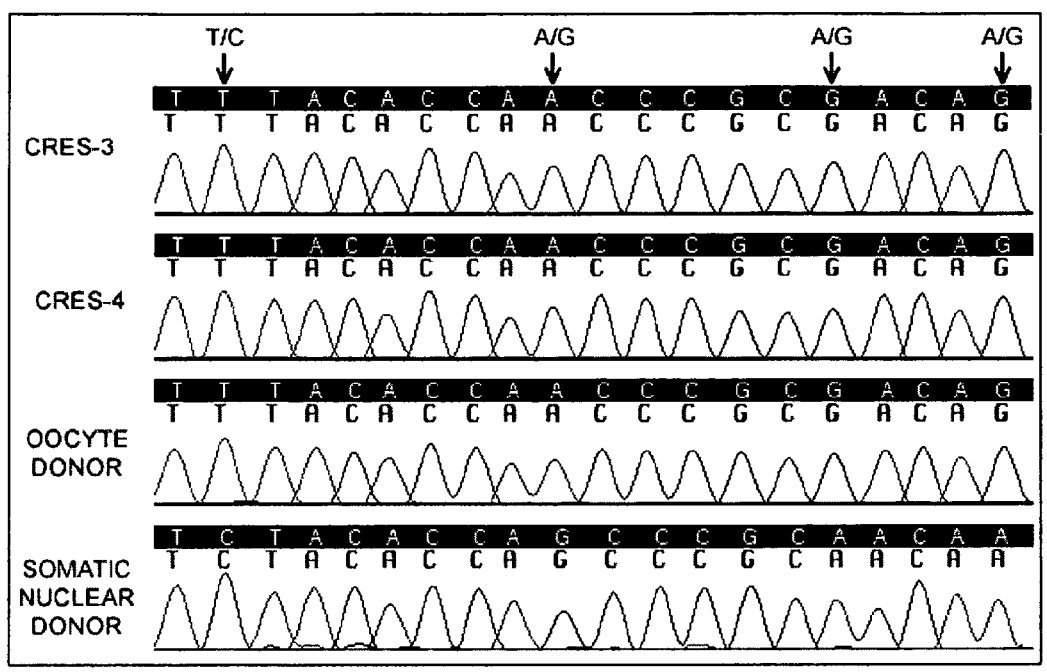
FIG. 10 is chromatograms of a mitochondrial (mt)DNA sequences analysis. A fragment of rhesus macaque mtDNA sequence showing four SNPs at positions T/C and AG. Sequence of CRES-3 and -4 mtDNA were identical to the oocyte donor female but different than the nuclear (skin) donor female.

On the other hand, mitochondrial (mt) DNA sequence analysis indicated that both CRES-3 and -4 inherited their mitochondria from an oocyte donor female #2 (FIG. 10). No contribution of nuclear donor somatic cells was detected in mtDNA population of CRES-3 and -4. Incidentally, the nuclear donor female #1 for CRES-3 and -4 was the oocyte (mtDNA) donor for CRES-1 as described above. Cytogenetic analysis by G-banding revealed that both CRES-3 and -4 contain normal female rhesus macaque karyotype (42, XX) with no detectable chromosomal anomalies.

Figure 11:
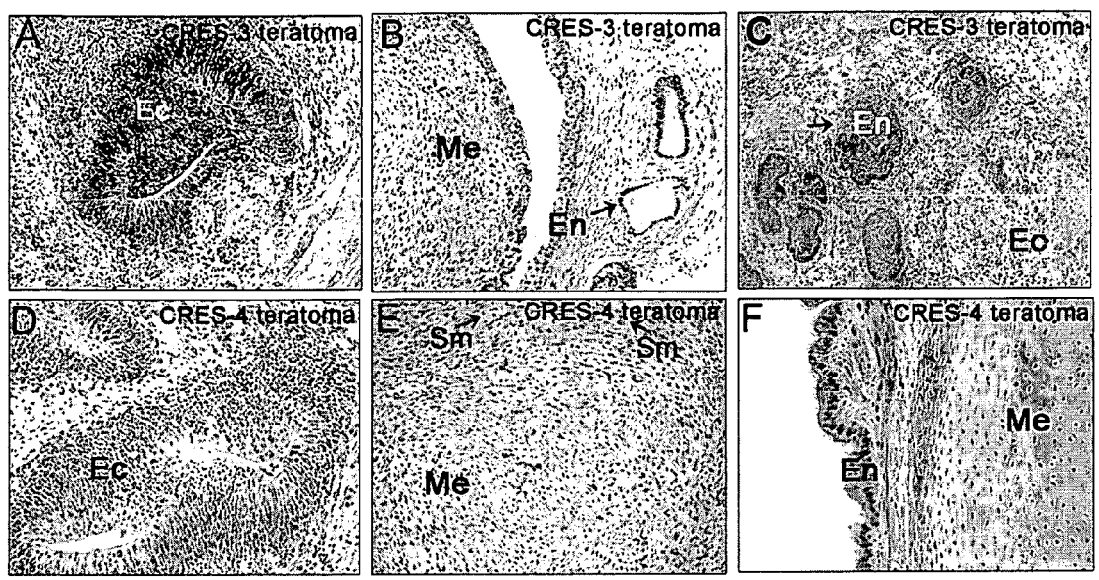
FIGS. 11A-11F are digital images of a histological analysis of teratoma tumors generated after injection of CRES-3 and -4 into SCID mice.

The key feature of pluripotent cells is their ability to differentiate into all cell types that compose a whole organism. To examine the extent of reprogramming and pluripotency, differentiation of novel SCNT-derived CRES-3 and -4 cells was induced in feeder-free suspension culture into embryoid bodies (EBs) followed by adhesion culture for several weeks. Differentiated cells exhibited a variety of different phenotypes and expression analysis confirmed the presence of cells and tissues from the three germ layers. Following appropriate differentiation, the expression of cardiospecific and neuronal markers could be demonstrated. Furthermore, both cell lines produced teratomas when injected into SCID mice. Histological analysis of the dissected tumors identified tissue representing the three germ layers (FIG. 11).

Figure 12:
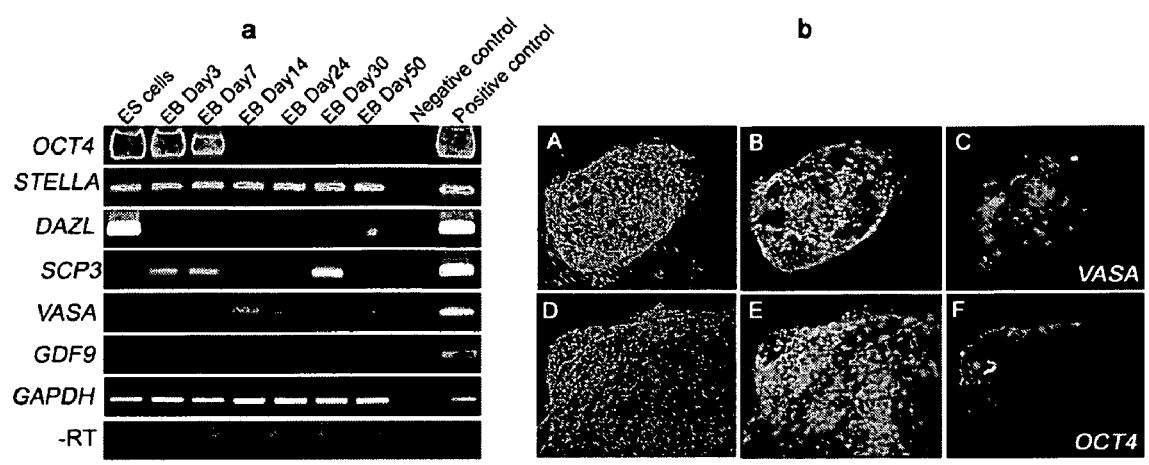
FIGS. 12a-12b are digital images showing expression of germ cell-specific markers during in vitro differentiation of CRES-3.

The ability to contribute to the germ line is important to evaluate the full potential of primate ES cells. Differentiation of CRES-3 and CRES-4 was induced by suspension culture into embryoid bodies (EBs) and expression of germ cell-specific markers were examined over an extended period. As expected, OCT4 was highly expressed in undifferentiated ES cells but gradually declined after differentiation (FIG. 12a). Low level of expression was detected again by day 50 of differentiation possibly indicating development of early postmigratory germ cells. Similar pattern was seen for DAZL, with expression in undifferentiated cells that was downregulated upon differentiation and reappeared at the later stages. Another marker, STELLA was expressed in undifferentiated as well as at all stages of differentiation of CRES cells. In contrast, transcripts of SCP3, VASA and GDF9 were not detected in undifferentiated ES cells but expressed at the later stages of differentiation suggesting that expression of these markers is restricted to germ cells, as is the case with other human ES cells (Clark et al, Stem Cells 22 (2), 169, 2004).

To corroborate these results, CRES cells were differentiated in feeder-free adhesion culture and the expression of germ cell markers was examined by immunocytochemistry. After differentiation for 4 weeks, cultures were represented by various cell types including spontaneously contracting cardiomyocytes. Spontaneous formation of cell aggregates was observed that detached from the large colonies (FIG. 12b, panel B). These aggregates were predominantly VASA positive, when immunolabeled with monoclonal antibody. Similar aggregates were also described during differentiation of mouse ES cells into oocytes (Hubner et al., Science 300 (5623), 1251, 2003) and it is likely that these cells share characteristics with early postmigratory germ cells. These differentiated cultures were immunolabel with OCT4 antibody and in contrast to mRNA expression islands of OCT4-positive cells were observed after 4 weeks of differentiation (FIG. 12b). Expression of OCT4 at this stage clearly indicates that these cells are not undifferentiated ES cells but rather are likely early postmigratory germ cells. Thus, monkey SCNT-derived ES cells are capable of differentiating into germ cells upon in vitro differentiation.

Example 11

Imprinted Gene Expression and Methylation in CRES Cell Lines

Genomic imprinting or preferential expression of one parental allele is regulated by epigenetic mechanisms including DNA methylation. Imprinted genes are known to be particularly susceptible to epigenetic alterations during in vitro embryo manipulations and ES cell culture[11-13]. Importantly, many defects often observed in cloned animals are associated with abnormal expression of imprinted genes due to improper reprogramming after SCNT (Mann et al., Biol Reprod 69 (3), 902, 2003). Disruption or inappropriate expression of imprinted genes is associated with cancer and tumour development, thus, it is important to address concerns over imprinting integrity in primate ES cells derived by SCNT prior to transplantation trials.

Figure 13:
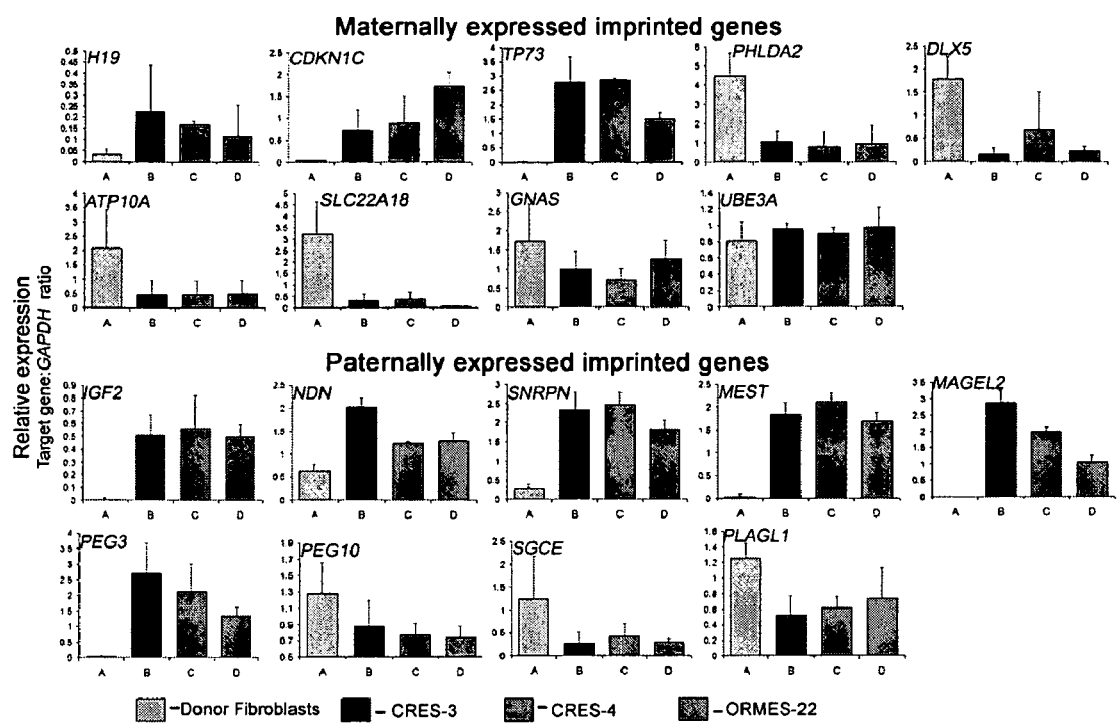
FIG. 13 are bar graphs showing the expression levels of selected maternally and paternally imprinted genes in CRES-3 and -4. The X axis represents: a—nuclear donor fibroblast, b—CRES-3, c—CRES-4 and IVF-derived ORMES-22. The Y-axis shows the relative expression levels of each imprinted gene as determined by comparison to the expression level of housekeeping control GAPDH (imprinted gene:GAPDH ratio). The mean expression level was calculated using a standard curve method followed by normalization with housekeeping GAPDH. Data represent the means±S.E.M. (n=6).

Expression levels of nine maternally and ten paternally expressed genes known to be imprinted in humans (see the Geneprint website, available on the internet) were examined in SCNT-derived CRES-3 and -4 and compared to the nuclear donor fibroblasts and ES cells derived from fertilized embryos (ORMES-22) (FIG. 13). Maternally expressed PHLDA2, DLX5, ATP10A and SLC22A18 were significantly upregulated in skin fibroblasts when compared to CRES and ORMES-22 cells. In contrast, several other maternally expressed imprinted genes including H19, CDKN1C and TP73 were upregulated in ES cells but expression was undetectable in fibroblasts (FIG. 13). Interestingly, the majority of analyzed paternally expressed genes including IGF2, NDN, SNRPN, MEST, MAGEL2, and PEG3 were upregulated in ES cells compared to somatic donor fibroblasts. Similar analysis was conducted with SCNT-derived CRES-1 and -2 and the results were comparable to CRES-3 and -4. Moreover, qPCR results were in agreement with expression levels of these imprinted genes determined previously by microarray analysis (available at the NCBI website on the internet).

Imprinted gene expression is intimately associated with maintenance of epigenetic marks including DNA methylation at so-called imprinting centers (ICs). Parent-of-origin-dependent DNA methylation of CpG dinucleotides, imposed during gametogenesis within ICs, facilitates discrimination between maternal and paternal alleles, resulting in monoallelic expression. These differentially methylated regions (DMRs) are thought to be resistant during genome-wide demethylation and remethylation waves observed during preimplantation embryo development (Reik et al., Science 293 (5532), 1089, 2001). However, abnormal DNA methylation after SCNT has been implicated in developmental failures and defects in embryos and offspring including primates (Dean et al., Biol Reprod 76 (1), 36, 2007). To examine if primate ES cells derived by SCNT retained differentially methylated patterns at imprinted loci, the methylation status of IGF2/H19 and SNRPN ICs was analyzed by methylation-sensitive Southern blot and bisulfite genomic sequencing as previously reported (see, for example, Mitalipov et al, Stem Cells 25 (3), 581; 2007). The presence of both methylated and unmethylated alleles was observed at both loci in nuclear donor fibroblasts, ORMES-22 and CRES cell lines, demonstrating the maintenance of normal methylation patterns in SCNT-derived primate ES cells.

These results show imprinted gene expression and methylation in CRES cells is similar to their IVF-derived counterparts indicating proper reprogramming after SCNT.

Example 12

Telomere Length and X-Inactivation

Figure 14:
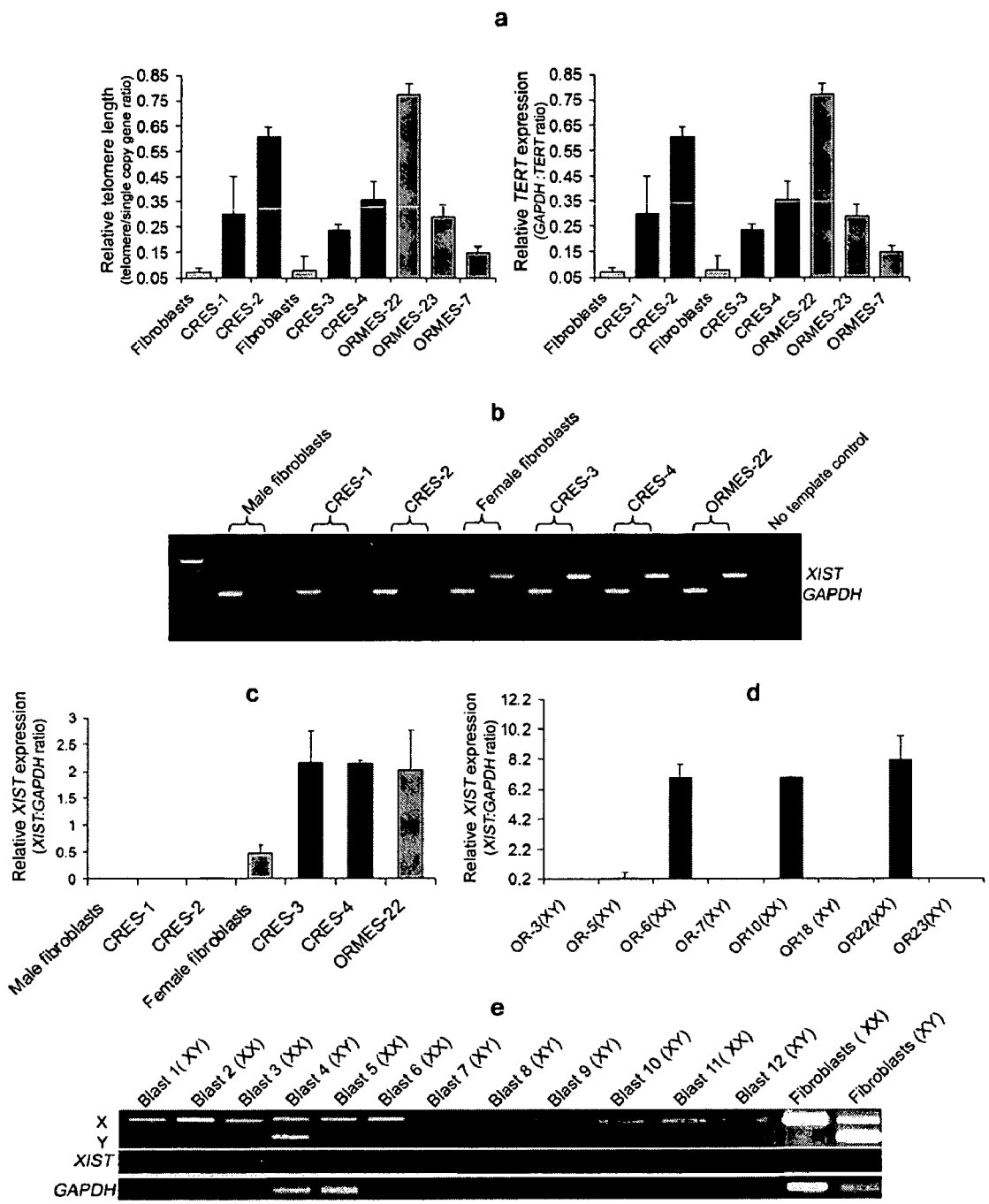
FIGS. 14a-14e are bar graphs and digital images of an analysis of telomere length and X-inactivation in CRES cells, a: relative telomere length and TERT expression in nuclear donor skin fibroblasts, CRES cell lines and IVF-derived ORMES-22, -23 and -7 determined by q-PCR. b, c and d: XIST expression by RT-PCR and q-PCR in undifferentiated private male and female ES cells. The data represents the mean±SEM (n=4), e: XIST expression in IVF-produced monkey blastocysts.

Telomeres are DNA-protein complexes at the ends of eukaryotic chromosomes essential for chromosomal integrity and normal cell growth. Telomere DNA is composed of TTAGGG tandem repeats that are progressively incised with each cell division at the rate of 50-150 base pairs per cell division in human cells leading to the replicative senescence (Maser and DePinho, Science 297 (5581), 565, 2002). Maintenance or elongation of telomeres in germ cells, early embryonic and ES cells is sustained by ribonucleoprotein complex telomerase. Shortened telomeres were implicated in premature aging and early death of some cloned offspring (Shiels et al., Cloning 1 (2), 119, 1999) indicating possible reprogramming errors after SCNT. To address this question the telomere length and telomerase (TERT) expression was examined in monkey SCNT-derived CRES cell lines using qPCR approach (Cawthon, Nucleic Acids Res 30 (10), e47, 2002). The results clearly demonstrated a significant elongation of telomere length in all CRES cell lines compared to the nuclear donor fibroblasts (FIG. 14a). Telomere length in SCNT-derived ES cells was comparable to IVF-derived controls, although a considerable variation was observed between ES cell lines. Furthermore, high levels of TERT expression detected in CRES and IVF-derived ES cells but not in skin fibroblasts supports this observation (FIG. 14). These data indicate an efficient reprogramming and restoration of replicative capacity of donor somatic cells to embryonic levels after primate SCNT. Dosage compensation in female mammals is achieved by epigenetic silencing gene expression from one X chromosome, a process known as X-inactivation (Lyon, Curr Biol 9 (7), R235, 1999). In the mouse, both X chromosomes are presumed to be active during preimplantation embryo development and undifferentiated mouse ES cells do not display an inactive X. Random X-inactivation occurs upon differentiation of mouse ES cells and mediated by xist gene activity that is expressed in cis front the chromosome to be inactivated (Borsani et al., Nature 351 (6324), 325, 1991). Timing and developmental regulation of X-inactivation in primates is unclear. However, in contrast to the mouse, the majority of examined undifferentiated human ES cell lines show X-inactivation, suggesting that in primates silencing one of X chromosomes occurs earlier. The X-inactivation status was assessed in female CRES-3 and -4 cells by measuring the level of XIST expression. All of the tested female samples including donor fibroblasts and undifferentiated CRES-3, -4 and IVF-derived ORMES-21 displayed strong XIST expression (FIGS. 14b, 14c). In contrast, XIST transcripts were not detected in male nuclear donor fibroblasts and CRES-1 and 2. Furthermore, an additional eight IVF-derived monkey ES cell lines (ORMES series; Hubner et al., Science 300 (5623), 1251, 2003)) were examined and all tested XX cell lines demonstrated high levels of XIST expression indicating X-inactivation (FIG. 14d).

To investigate the status of X-inactivation in monkey blastocysts, an embryonic stage from which ES cells are derived, XIST expression was examined in twelve IVF-produced embryos. Simultaneously, a PCR-based sexing of individual blastocysts was conducted using size differences in the genomic DNA amplicons of the X- and Y-linked zinc finger protein genes (ZFX and ZFY) as previously described (Borsani et al, Biol Chem 379 (10), 1287, 1998). The results demonstrated that XIST is not detectable in male and female monkey blastocysts (FIG. 14e). This suggests that similar to the mouse, both X chromosomes are active in primate preimplantation embryos. However, undifferentiated monkey ES cells already underwent X-inactivation. These data also indicate that epigenetic marks regulating X-inactivation are faithfully recapitulated in female primate ES cells after SCNT.

Thus, the above SCNT procedure was modified by eliminating $Ca^{2++}$ ions from the fusion media, yielding a near three-fold increase in the blastocyst formation rate (from 16% to 43%). Another modification to the ES derivation procedures involved plating intact (whole) blastocysts as opposed to isolated ICMs onto feeder layer. In the work described above only 10% of monkey SCNT embryos resulted in ES cell lines when the majority of blastocysts were immunosurgically dissected for ICMs isolation. Without being bound by theory, exposure of SCNT blastocyst to the antibody followed by treatment with complement to selectively destroy trophectodermal (TE) cells may also affect the viability of ICM cells. Using whole SCNT blastocysts in this study significantly increased ES cell derivation rates to 29%, an efficiency similar to that from IVF-derived embryos. Given the SCNT blastocyst formation rate of 43% and ES cell isolation efficiency of 29%, as few as ten or less primate oocytes could be sufficient to derive one cell line.

Comprehensive studies confirmed the somatic origin and pluripotency of CRES-3 and -4. One of the two derived ES cell lines described herein, CRES-1 was aneuploid. However, both CRES-3 and -4 exhibited a normal female rhesus macaque chromosome (42, XX) complement suggesting that cytogenetic aberrations are not common in primate SCNT-derived ES cells.

In addition to the routine pluripotency tests by in vitro and in vivo differentiation to various somatic cell types, it was demonstrated that primate ES cells derived from reprogrammed somatic cells are capable of contributing to the germ line. Thus, a patient's somatic cells can be used to reprogram to ES cells, which subsequently can be differentiated into oocytes or sperm. Using the techniques disclosed herein could thus result in infertile patients having children that are genetically their own. Conversely, human ES cell-derived eggs could have many research uses, such as for the production of ES cells, thus reducing the need to use fertilized human eggs for research. In addition the in vitro derivation of germ cells can be used to study early germ cell development, imprinting, follicle formation and early embryonic growth.

Thus, pluripotent cells derived by SCNT are identical to ES cells derived from fertilized embryos in terms of transcriptional activity and potential to give rise to all cell types that compose an organism including germ cells. A detailed examination of epigenetic characteristics that define ES cells was also conducted, as described herein. The analysis of imprinted genes indicated that expression levels of several paternally and maternally imprinted genes in CRES cell lines were remarkably similar to controls. High levels of TERT expression and significant elongation of telomere length in SCNT-derived ES cell lines compared to nuclear donor fibroblasts indicate efficient reprogramming of proliferative potential to early embryonic state. It was also demonstrated that undifferentiated female CRES cells, similar to their IVF-derived counterparts underwent X-inactivation. These observations are consistent with conclusion that oocyte-induced reprogramming of primate somatic cells results in complete erasure of somatic memory and resetting of new ES cell-specific epigenetic state.

Example 13

Methods Summary for Examples 9-12

SCNT Procedures: Details of methods for monkey SCNT, embryo culture, ES cell isolation and characterization are described above. Briefly, mature metaphase II oocytes were enucleated using the OOSIGHT™ Imaging System (CRI, Inc., Woburn, Mass.) and a donor somatic cell nucleus was introduced into a cytoplast through electrofusion in $Ca^{2++}$-free buffer. Reconstructed embryos were activated 2 hours after fusion as previously described and cultured to blastocysts. Whole blastocysts or isolated ICMs were plated onto feeder layers and attached to the feeder layer ICM outgrowth were manually dissociated into small clumps with a microscalpel and replated onto fresh dishes. Colonies with ES cell-like morphology were selected for further propagation, characterization, and in vitro and in vivo differentiation as described above.

Telomere length measurements: Relative telomere length was measured using a real-time quantitative PCR method as previously described (Cawthon, *Nucleic Acids Res* 30 (10), e47, 2002) using primers Tel1 and Tel2 for telomeres and 36B4 for acidic ribosomal phosphoprotein P0 (RPLPO) used as a single-copy gene reference (see Table 16).

TABLE 16

| Primers, probes and PCR conditions | | | | |
|---|---|---|---|---|
| Primers for RT-PCR | | | | |
| Gene | 5' PRIMER | 3' PRIMER | Product size | TM |
| GAPDH | GTGGTCTCCTCCGACT TCAACA (SEQ ID NO: 1) | GTCTCTCTCTTCCTCTT GTGCTCT (SEQ ID NO: 2) | 217 | 61 |
| Alpha-MHC | GTCATTGCTGAAACCG AGAATG (SEQ ID NO: 3) | GCAAAGTACTGGATGAC ACGCT (SEQ ID NO: 4) | 413 | 61 |
| hANP | GAACCAGAGGGGAGAG ACAGAG (SEQ ID NO: 5) | CCCTCAGCTTGCTTTTT AGGAG (SEQ ID NO: 6) | 406 | 61 |
| NKX2.5 | TGGCTACAGCTGCACT GCCG (SEQ ID NO: 7) | GGATCCATGCAGCGTGG AC (SEQ ID NO: 8) | 167 | 57 |
| Mlc2a | ACAGAGTTTATTGAGG TGCCCC (SEQ ID NO: 9) | AAGGTGAAGTGTCCCAG AGG (SEQ ID NO: 10) | 381 | 61 |
| cTnT | GGCAGCGGAAGAGGAT GCTGAA (SEQ ID NO: 11) | GAGGCACCAAGTTGGGC ATGAACGA (SEQ ID NO: 12) | 150 | 64 |
| FOXA2 | ACCCGTTCTCCATCAA CAACCTCA (SEQ ID NO: 13) | AAGTGTGACCCTCTGTT TGGGACA (SEQ ID NO: 14) | 459 | 59 |
| NEFM | TGG GAA ATG GCT CGT CAT TT (SEQ ID NO: 15) | CTT CAT GGA AGC GGC CAC TT (SEQ ID NO: 16) | 336 | 53 |
| NESTIN | GCC CTG ACC ACT CCA GTT TA (SEQ ID NO: 17) | GGA GTC CTG GAT TTC CTT CC (SEQ TD NO: 18) | 200 | 53 |
| PDX | ACC AAA GCT CAC GCG TGG AAA (SEQ ID NO: 19) | TGA TGT GTC TCT CGG TCA AGT T (SEQ ID NO: 20) | 199 | 56 |
| GDF9 | CATGGCACGTCCCAAC AAATTCCT (SEQ ID NO: 21) | AAGGATGCTCCAGCTGG TCTTTCA (SEQ ID NO: 22) | 743 | 58 |
| SCP3 | ATTCCAGGAAATCTGG GAAGCCGT (SEQ ID NO: 23) | TCCAGCATATTCTGCAC TTCACCC (SEQ ID NO: 24) | 202 | 59 |

TABLE 16-continued

Primers, probes and PCR conditions

| | | | | |
|---|---|---|---|---|
| STEELAR | GTTACTGGGCGGAGTT CGTA (SEQ ID NO: 25) | TGAAGTGGCTTGGTGTC TTG (SEQ ID NO: 26) | 174 | 60 |
| DAZL | ATGTTAGGATGGATGA AACTGAGATTA (SEQ ID NO: 27) | CCATGGAAATTTATCTG TGATTCTACT (SEQ ID NO: 28) | 178 | 51 |
| VASA | AAGAGAGGCTATCGAG ATGGA (SEQ ID NO: 29) | CGTTCACTTCCACTGCC ACTTCTG (SEQ ID NO: 30) | 238 | 54 |
| XIST | TAATGTGCCAGATACC ATGCTGGG (SEQ ID NO: 31) | ACTTAACCTCACCAGTA AAGTCTTGAT (SEQ ID NO: 32) | 327 | 55 |

Primers for qRT-PCR (SYBR Green)

| Gene | Primer Sequence |
|---|---|
| Tel1 | GGT TTT TGA GGG TGA GGG TGA GGG TGA GGG TGA GGG T (SEQ ID NO: 33) |
| Tel2 | TCC CGA CTA TCC CTA TCC CTA TCC CTA TCC CTA TCC CTA (SEQ ID NO: 34) |
| 36B4u | CAG CAA GTG GGA AGG TGT AAT CC (SEQ ID NO: 35) |
| 36B4d | CCC ATT CTA TCA TCA ACG GGT ACA A (SEQ ID NO: 36) |

Primers and probes for q-PCR

| GENE | 5' PRIMER | 3' PRIMER | PROBE |
|---|---|---|---|
| PLAG1 | AGTACAACACCAT GCTGGGCTAT (SEQ ID NO: 37) | TGCTGGCCGCATGG A (SEQ ID NO: 38) | AGAGGCACCTGGCC (SEQ ID NO: 39) |
| SGCE | ACCCAAAACCTGG CGAGAT (SEQ ID NO: 40) | TCCAGGTCGGTCTGG GTAAC (SEQ ID NO: 41) | AGTAATGATCCCATAAC ATT (SEQ ID NO: 42) |
| SNRPN | AAGCAACCAGAGC GTGAAGAA (SEQ ID NO: 43) | TCCCCACGCAGCAA CAC (SEQ ID NO: 44) | AGCGGGTTTTGGGTCT (SEQ ID NO: 45) |
| H19 | CCTCCCCGACTCTG TTTCC (SEQ ID NO: 46) | CACAACTCCAACCA GTGCAAA (SEQ ID NO: 47) | CCGTCCCTTCTGAATT (SEQ ID NO: 48) |
| IGF2 | GTCGGCCCAGCCA GAGT (SEQ ID NO: 49) | CGGCTACCATCATCT CCATTG (SEQ ID NO: 50) | AGGAAGGAGTTTGGCC (SEQ ID NO: 51) |
| NECDIN | TGTCTCCGAGGACT AGCCAAGT (SEQ ID NO: 52) | GCCCTGGTGAGGAT CAGAAA (SEQ ID NO: 53) | TGGAGGCAGATGAAT (SEQ ID NO: 54) |
| UBE3A | GAAGGAGAACAAG GAGTTGATGAAG (SEQ ID NO: 55) | CCTCCACAACCAGCT GAAAAA (SEQ ID NO: 56) | AGGTGTTTCCAAAGAA (SEQ ID NO: 57) |
| PEG10 | CCCTTCGAGAGCA AGTGGAA (SEQ ID NO: 58) | GCGGAGCTCGATGT CATCAT (SEQ ID NO: 59) | CCACCCCTGAGGATG (SEQ ID NO: 60) |
| ATP10A | GCCCGGCCAACGT GTAC (SEQ ID NO: 61) | ACCGCCGGCACGAA GT (SEQ ID NO: 62) | TTGTCTTCATCGCGCTG C (SEQ ID NO: 63) |
| CDKN1C | CATCTACGATGGA GCGTCTTGTC (SEQ ID NO: 64) | GCTGGTGCGCACAA GTACTG (SEQ ID NO: 65) | CCGTGGGACCTTC (SEQ ID NO: 66) |

TABLE 16-continued

Primers, probes and PCR conditions

| Gene | Forward | Reverse | Probe |
|---|---|---|---|
| DLX5 | ACCAACCAGCCAG AGAAAGAAG (SEQ ID NO: 67) | TTGGTTTGCCATTCA CCATTC (SEQ ID NO: 68) | CACCTCGGGCTCGG (SEQ ID NO: 69) |
| GNAS | TGGCCAGCAGCAG CTACA (SEQ ID NO: 70) | TCCTGCAGGCGGTTG GT (SEQ ID NO: 71) | TCATCCGGGAGGACAA (SEQ ID NO: 72) |
| MAGEL2 | CAGGGCCCCTTCGA AAGA (SEQ ID NO: 73) | CTGCCTTGGGAGCA CAGAA (SEQ ID NO: 74) | CGCATGATCTTTGCTGC (SEQ ID NO: 75) |
| MEST | CCTGCCCTTCACTC ATGGAA (SEQ ID NO: 76) | GGTAGAAGATACGC AGTCCCTTGT (SEQ ID NO: 77) | TCTTCAGGCAAGTTTTT (SEQ ID NO: 78) |
| PEG3 | CAAGCACCAGTCG AGGTCTAAA (SEQ ID NO: 79) | CGCCGGTGGGTTGAT TT (SEQ ID NO: 80) | ACTATGCCTGAAGCCAA (SEQ ID NO: 81) |
| PHLDA2 | GAGCGCACCGGCA AGTAC (SEQ ID NO: 82) | CAGCGGAAGTCGAT CTCCTT (SEQ ID NO: 83) | TGTACTTCACCATCGTC A (SEQ ID NO: 84) |
| SLC22A18 | CCCGGCCTGGTGTT CAG (SEQ ID NO: 85) | GGCCTTGGTCAGCAT GCT (SEQ ID NO: 86) | TCTGCACACTCAATG (SEQ ID NO: 87) |
| ZIM2 | CCTCACTCAGTCCG TTCTTTCA (SEQ ID NO: 88) | GGCTCCATGTCTCTG CTTCTG (SEQ ID NO: 89) | TGGTGACCGGGACTG (SEQ ID NO: 90) |
| TP73 | CCAGCACGGCCAA GTCA (SEQ ID NO: 91) | CTTGGCGATCTGGCA GTAGAG (SEQ ID NO: 92) | CTGGACGTACTCCC (SEQ ID NO: 93) |
| GAPDH | GGTGGTCTCCTCCG ACTTCA (SEQ ID NO: 94) | ACCAGGAAATGAGC TTGACAAAG (SEQ ID NO: 95) | CCCACTCTTCCACCTTC GACGCTG (SEQ ID NO: 96) |
| OCT4 | CCCACTGGTGCCGT GAA (SEQ ID NO: 97) | TTGGCAAATTGCTCG AGTTCT (SEQ ID NO: 98) | GGACTCCTCCGGGTTTT GCTCCAG (SEQ ID NO: 99) |
| XIST | CCATGCTGGGTGCT AGAGCTA (SEQ ID NO: 100) | CCATTGACATTTGTA TCATGCTTTAGT (SEQ ID NO: 101) | AGGTGCATATTAAAGTG C (SEQ ID NO: 102) |

Amplification was performed using ABIPrism 7500 sequence detection system (Applied Biosystems) under following conditions: for Tel1 and Tel2 primers -30 cycles at 95° C. for 15 seconds and 54° C. for 2 minutes; for 36B4 primers -30 cycles at 95° C. for 15 seconds and 58° C. for 1 minute. To determine the cycle threshold (Ct) value, 2 separate PCR runs were performed for each sample and primer pair. For each run a standard curve was generated using a reference genomic DNA isolated from IVF-derived ES cells diluted to 0.06 to 40 ng per well (5 fold dilution). Calculation of the relative telomere/single copy gene ratio (T/S value) and statistical analysis with SDS v. 1.1 software (Applied Biosystems) was used to determine standard curve and Ct values. A point on the standard curve at a concentration corresponding to the average DNA concentration of the samples was used as a calibrator. The mean T/S value of skin fibroblasts and ESCs were compared and plotted against each sample.

X-inactivation: Qualitative and quantitative RT-PCR analysis was performed using primers and probes presented in Table 16. Amplification parameters for RT-PCR were as follows: 1 cycle at 94° C. for 2 minutes; 35 cycles at 94° C. for 30 seconds, 55° C. for 30 seconds, and 72° C. for 30 sec; and 1 cycle at 72° C. for 10 minutes.

Statistical analysis: For quantitative analysis of maternally and paternally expressed imprinted genes, xist expression, and telomere length measurements, statistical analysis with SDS v. 1.1 software (Applied Biosystems) was used.

It will be apparent that the precise details of the methods or compositions described may be varied or modified without departing from the spirit of the described invention. We claim all such modifications and variations that fall within the scope and spirit of the claims below.

We claim:

1. A method for producing a pluripotent primate stem cell comprising the steps of:
   (a) enucleating a recipient primate host oocyte cell from a first primate using a real-time non-UV-based spindle polarized light imaging system in the absence of staining and in a manner that does not lower levels of maturation promoting factor (MPF) to form an enucleated oocyte;
   (b) introducing a nucleus of a donor primate somatic cell from a second primate into the enucleated oocyte in Ca2 free medium under conditions that reduce or eliminate calcium oscillations, wherein the first primate and the second primate are from the same primate species, to produce a reconstituted primate embryo;
   (c) activating the reconstituted embryo;
   (d) culturing the reconstituted embryo to the blastocyst stage;
   (e) isolating the inner cell mass cells from the blastocyst; and
   (f) culturing the inner cell mass cells on a fibroblast feeder layer so that the cells divide,
thereby producing a primate stem cell that is pluripotent, wherein the pluripotent stem cell (i) is capable of four or more cell divisions; (ii) maintains a normal karyotype while in culture; (iii) is capable of differentiating into ectoderm, mesoderm, and endoderm layers; and (iv) comprises mitochondrial DNA derived from the oocyte of the first primate recipient and nuclear genetic material from the donor primate somatic cell of the second primate.

2. The method of claim 1, further comprising one or more of
   detecting chromosome condensation, detecting nuclear envelope breakdown, and detecting disappearance of laminin A/C.

3. The method of claim 1, wherein the pluripotent stem cells are produced with an efficiency greater than about 10%.

4. The method of claim 1, wherein said isolating the inner cell mass culturing does not comprise immunosurgery.

5. The method of claim 1 wherein a Major Histocompatibility (MHC) loci of the donor primate somatic cell matches at least one MHC loci of an individual in need of stem cell therapy.

6. The method of claim 1, wherein the donor primate somatic cell is a human somatic cell.

7. The method of claim 1, wherein the first primate recipient and the second primate donor are a human.

8. The method of claim 1, wherein the pluripotent primate stem cell is immortalized.

9. The method of claim 1, wherein the somatic cell is a skin cell, a fibroblast, a nucleated hematopoietic cell, a muscle cell, a hair follicle cell, or an adipose cell.

10. The method of claim 1, wherein the pluripotent primate stem cell expresses an imprinted gene.

11. The method of claim 10, wherein the imprinted gene is H19, CDKNIC, PHLDA2, DLX5, ATP10A, SLC22A18, TP73, IGF2, NDN, SNRPN, MEST, MAGEL2 or PEG3.

12. The method of claim 1, wherein telomeres of the pluripotent primate stem cell are elongated in comparison to telomeres of a fibroblast from the second primate donor.

13. The method of claim 1, wherein the pluripotent primate stem cell expresses an increased amount of telomerase as compared to a fibroblast from the second primate donor.

14. The method of claim 1, wherein the pluripotent primate stem cell includes two X chromosomes.

15. The method of claim 1, wherein the pluripotent primate stem cell has undergone X inactivation.

16. The method of claim 1, wherein the pluripotent primate stem cell expresses XIST.

17. The method of claim 1, wherein the pluripotent primate stem cell includes an X and a Y chromosome.

* * * * *

UNITED STATES PATENT AND TRADEMARK OFFICE
CERTIFICATE OF CORRECTION

PATENT NO. : 7,972,849 B2
APPLICATION NO. : 12/122557
DATED : July 5, 2011
INVENTOR(S) : Mitalipov et al.

It is certified that error appears in the above-identified patent and that said Letters Patent is hereby corrected as shown below:

In the Abstract:
    Column 84, line 2, "stems cells" should read -- stem cells --

Other Publications:
    IDS 3/13/10, p. 2 of 5, "Galactosyltranserase" should read -- Galactosyltransferase --
    IDS 3/13/10, p. 4 of 5, "blastocycts" should read -- blastocysts --
    IDS 3/13/10, p. 4 of 5, "(2000),." should read -- (2000). --

In the Figures:
    FIG. 9, "alfa" should read -- alpha --
    FIG. 11, "smooth muscles cells" should read -- smooth muscle cells --
    FIG. 11, "densly" should read -- densely --
    FIG. 11, "columnar epithelum" should read -- columnar epithelium --

In the Specification:
    Column 2, line 2, "(2002)." should read -- (2002)). --
    Column 2, line 26, "producing a primate" should read -- producing primate --
    Column 2, line 35, "produce a primate" should read -- produce primate --
    Column 2, line 37, "maintains" should read -- maintain --
    Column 2, line 40, "comprises" should read -- comprise --
    Column 3, line 38, "ZFY." should read -- ZFY). --
    Column 4, line 10, "q10)[17]" should read -- (q10)[17] --
    Column 4, line 39, "Sequence" should read -- Sequences --
    Column 4, line 50, "represents" should read -- represent --
    Column 5, line 4, "and IVF-derived" should read -- and d-IVF-derived --
    Column 5, line 13, "cells," should read -- cells. --
    Column 5, line 18, "private" should read -- primate --
    Column 5, line 19, "(n=4)," should read -- (n=4). --
    Column 5, line 53, "that the" should read -- the --

Signed and Sealed this
Twenty-fourth Day of July, 2012

David J. Kappos
*Director of the United States Patent and Trademark Office*

CERTIFICATE OF CORRECTION (continued)
U.S. Pat. No. 7,972,849 B2

Column 6, line 40, "authologons" should read -- autologons --
Column 6, line 56, "Freshney)" should read -- Freshney --
Column 6, line 63, "1991) Short" should read -- 1991); Short --
Column 6, line 64, "1999), Embryonic" should read -- 1999); Embryonic --
Column 6, line 66, "Essential of" should read -- Essentials of --
Column 7, line 46, "sense" should read -- senses --
Column 7, line 64, "to sufficient" should read -- sufficient to --
Column 8, line 2, "poplation" should read -- population --
Column 9, line 40, "collagenoous" should read -- collagenous --
Column 9, line 41, "laimina" should read -- lamina --
Column 9, line 54, "condensing" should read -- condensins --
Column 11, line 26, "C14orfl 15" should read -- C14orfl15 --
Column 12, line 59, "its" should read -- their --
Column 13, line 10, "cell" should read -- cells --
Column 13, line 13, "maintains" should read -- maintain --
Column 13, line 29, "its" should read -- their --
Column 14, line 1, "transplantable, cells" should read -- transplantable cells --
Column 14, line 4, "that that" should read -- that --
Column 14, lines 54-55, "TSCs exhibits" should read -- TSCs exhibit --
Column 15, line 4, "cells is" should read -- cell is --
Column 16, lines 7-8, "visuzalization" should read -- visualization --
Column 16, line 14, "allow" should read -- allows --
Column 16, line 37, "antoher" should read -- another --
Column 16, line 60, "Freshney)" should read -- Freshney --
Column 17, line 1, "1991) Short" should read -- 1991); Short --
Column 17, line 2, "1999), Embryonic" should read -- 1999); Embryonic --
Column 17, lines 3-4, "Essential of" should read -- Essentials of --
Column 17, lines 55-60, "mM" should read -- µM --
Column 18, lines 21-22, "a... techniques" should read -- techniques --
Column 18, line 57, "B-" should read -- β- --
Column 18, line 65, "reaches" should read -- reach --
Column 19, line 4, "are be removed" should read -- are removed --
Column 19, line 8, "abut" should read -- about --
Column 19, line 46, "N2" should read -- $N_2$ --
Column 20, lines 42-43, "primate that is the" should read -- primate is the --
Column 20, line 59, "PSCS" should read -- PSCs --
Column 21, line 65, "extaneurally" should read -- extraneurally --
Column 22, line 44, "individual" should read -- individuals --
Column 22, line 61, "egges" should read -- eggs --
Column 23, line 3, "using culturing" should read -- using or culturing --
Column 23, line 15, "used in to screen" should read -- used to screen --
Column 23, line 17, "cell" should read -- cells --
Column 23, line 18, "agent" should read -- agents --
Column 23, line 46, "a function" should read -- a function of --
Column 24, line 12, "$Ca^2+$ and $mg^2+$" should read -- $Ca^{2+}$ and $Mg^{2+}$ --

CERTIFICATE OF CORRECTION (continued)

Column 24, lines 27-29, "Meng et al., Biol Reprod 66(5): 1367-73, 1997; Mitaliprov et al., Biol Reprod 66(5): 1367-73, 2002" should read -- Mitaliprov et al., Biol Reprod 66(5): 1367-73, 2002 --

Column 25, line 42, "N2" should read -- $N_2$ --
Column 25, line 57, "horomone" should read -- hormone --
Column 26, line 4, "CaCL$_2$" should read -- $CaCl_2$ --
Column 26, line 16, "0.2," should read -- 0.2μ --
Column 26, line 34, "0.2," should read -- 0.2μ --
Column 27, line 54, "laporascopic" should read -- laparoscopic --
Column 28, line 22, "dissecting a" should read -- a dissecting --
Column 29, line 16, "Mm" should read -- μm --
Column 29, line 35, "by exposure by exposure" should read -- by exposure --
Column 29, line 35, "mM" should read -- μM --
Column 30, line 2, "ZFY was" should read -- ZFY) was --
Column 32, line 63, "set" should read -- sets --
Column 33, line 28, "acetic:acid" should read -- acetic acid --
Column 33, line 63, "mitchondrion" should read -- mitochondrion --
Column 34, lines 31-32, "and or" should read -- and/or --
Column 35, Table 2, "Oocytestage" should read -- oocyte stage --
Column 40, line 52, "Medium)[37]" should read -- Medium) --
Column 40, line 64, "20-25μ" should read -- 20-25μm --
Column 41, line 34, "previous" should read -- previously --
Column 42, line 7, "described[17]." should read -- described. --
Column 42, Table 2, "fro" should read -- for --
Column 45, line 57, "(ORMES-22[17])" should read ORMES-22) --
Column 46, line 47, "i(Y)q10)" should read -- i(Y)(q10) --
Column 48, line 60, "2006." should read -- 2006). --
Column 49, line 19, "2006)" should read -- 2006). --
Column 49, line 35, "Mitalipove" should read -- Mitalipov --
Column 51, Table 13, "58 (98)" should read -- 58 (98%) --
Column 54, line 14, "immunolabel" should read -- immunolabeled --
Column 54, line 23, "Example 11" should read -- Example 12 --
Column 54, line 32, "culture[11-13]." should read -- culture. --
Column 55, line 60, "front the" should read -- from the --
Column 56, line 3, "ORMES-21" should read -- ORMES-22 --
Column 56, line 8, "2003))" should read -- 2003) --
Column 58, line 18, "(RPLPO)" should read -- (RPLP0) --
Column 58, Table 16, "SEQ TD NO:" should read -- SEQ ID NO: --
Column 95, line 10, "Ca2" should read -- $Ca^{2+}$ --
Column 96, line 2, "mass culturing does" should read -- mass does --